(12) United States Patent  
Fisher et al.

(10) Patent No.: US 11,988,957 B2  
(45) Date of Patent: May 21, 2024

(54) FLOW CELLS

(71) Applicants: ILLUMINA, INC., San Diego, CA (US); ILLUMINA CAMBRIDGE LIMITED, Cambridge (GB)

(72) Inventors: Jeffrey S. Fisher, San Diego, CA (US); Brian D. Mather, San Diego, CA (US); Maria Candelaria Rogert Bacigalupo, Encinitas, CA (US); Justin Fullerton, San Diego, CA (US); Ludovic Vincent, San Diego, CA (US); Lewis J. Kraft, San Diego, CA (US); Sahngki Hong, San Diego, CA (US); Boyan Boyanov, San Diego, CA (US); M. Shane Bowen, Encinitas, CA (US); Sang Park, San Diego, CA (US); Wayne N. George, Ilford (GB); Andrew A. Brown, Cambridge (GB)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 0 days.

(21) Appl. No.: 18/317,865

(22) Filed: May 15, 2023

(65) Prior Publication Data

US 2023/0332224 A1 Oct. 19, 2023

Related U.S. Application Data

(60) Continuation of application No. 17/840,569, filed on Jun. 14, 2022, now Pat. No. 11,680,292, which is a
(Continued)

(51) Int. Cl.
*G03F 7/00* (2006.01)
*C08F 220/56* (2006.01)
(Continued)

(52) U.S. Cl.
CPC .......... *G03F 7/0002* (2013.01); *C08F 220/56* (2013.01); *C08G 77/04* (2013.01);
(Continued)

(58) Field of Classification Search
CPC .......... G03F 7/165; C12Q 1/68; C12Q 1/6869
See application file for complete search history.

(56) References Cited

U.S. PATENT DOCUMENTS 6,133,436 A 10/2000 Koster et al.
6,858,394 B1 2/2005 Chee et al.
(Continued)

FOREIGN PATENT DOCUMENTS

TW 202130416 A 8/2021
WO 0061720 A2 10/2000
(Continued)

OTHER PUBLICATIONS

Cummins, C., et al., "Self-Assembled Nanofeatures in Complex Three-Dimensional Topographies via Nanoimprint and Block Copolymer Lithography Methods", ACS Omega, 2, pp. 4417-4423, Aug. 10, 2017.
(Continued)

*Primary Examiner* — Amanda C. Walke
(74) *Attorney, Agent, or Firm* — Dierker & Kavanaugh, P.C.

(57) ABSTRACT

An example of a flow cell includes a substrate; a first primer set attached to a first region on the substrate, the first primer set including an un-cleavable first primer and a cleavable second primer; and a second primer set attached to a second region on the substrate, the second primer set including a cleavable first primer and an un-cleavable second primer.

15 Claims, 31 Drawing Sheets

Specification includes a Sequence Listing.

Related U.S. Application Data continuation of application No. 17/139,834, filed on Dec. 31, 2020, now Pat. No. 11,384,392, which is a division of application No. 16/626,452, filed as application No. PCT/US2019/036105 on Jun. 7, 2019, now Pat. No. 11,124,829.

(60) Provisional application No. 62/743,373, filed on Oct. 9, 2018, provisional application No. 62/692,511, filed on Jun. 29, 2018.

(51) Int. Cl.
    *C08G 77/04*     (2006.01)
    *C12Q 1/6869*     (2018.01)
    *G03F 7/075*     (2006.01)
    *G03F 7/16*     (2006.01)
    *G03F 7/004*     (2006.01)

(52) U.S. Cl.
    CPC ......... *C12Q 1/6869* (2013.01); *G03F 7/0757* (2013.01); *G03F 7/165* (2013.01); *G03F 7/0046* (2013.01)

(56) References Cited

U.S. PATENT DOCUMENTS

| | | | |
|---|---|---|---|
| RE41,005 E | 11/2009 | Koster et al. | |
| 7,790,350 B2 | 9/2010 | Breyta et al. | |
| 7,842,649 B2 | 11/2010 | Seul et al. | |
| 8,993,088 B2 | 3/2015 | Millward et al. | |
| 9,087,699 B2* | 7/2015 | Millward | H01L 29/0657 |
| 9,299,381 B2* | 3/2016 | Nealey | B82Y 40/00 |
| 9,557,640 B2* | 1/2017 | Willson | G03F 7/20 |
| 9,586,346 B2 | 3/2017 | Nicolau et al. | |
| 9,982,294 B2 | 5/2018 | Fabani et al. | |
| 9,993,794 B2 | 6/2018 | Turner et al. | |
| 10,329,610 B2 | 6/2019 | Nashtaali et al. | |
| 10,338,056 B2 | 7/2019 | Hyde et al. | |
| 10,669,570 B2 | 6/2020 | Chang et al. | |
| 2010/0101956 A1 | 4/2010 | Choi et al. | |
| 2010/0248237 A1 | 9/2010 | Froehlich et al. | |
| 2012/0015358 A1 | 1/2012 | Scarr et al. | |
| 2012/0202017 A1 | 8/2012 | Nealey et al. | |
| 2014/0194324 A1 | 7/2014 | Gormley et al. | |
| 2015/0111256 A1 | 4/2015 | Church et al. | |
| 2015/0240300 A1 | 8/2015 | Ansari et al. | |
| 2016/0139012 A1 | 5/2016 | D'Silva et al. | |
| 2016/0318016 A1 | 11/2016 | Hou et al. | |
| 2017/0051340 A1 | 2/2017 | Gunderson et al. | |
| 2017/0299548 A1* | 10/2017 | Yoshida | G01N 33/48721 |
| 2017/0342406 A1 | 11/2017 | Rigatti et al. | |
| 2018/0030213 A1* | 2/2018 | Johnson | C08G 83/008 |
| 2018/0030529 A1 | 2/2018 | Nashtaali et al. | |
| 2018/0037950 A1 | 2/2018 | Gunderson et al. | |
| 2018/0179575 A1 | 6/2018 | George et al. | |
| 2018/0371535 A1 | 12/2018 | Bowen et al. | |
| 2020/0224020 A1 | 7/2020 | George et al. | |
| 2020/0308640 A1 | 10/2020 | Almogy et al. | |
| 2020/0332357 A1 | 10/2020 | Hansen et al. | |
| 2022/0154177 A1 | 5/2022 | Artioli et al. | |

FOREIGN PATENT DOCUMENTS

| | | |
|---|---|---|
| WO | 2012170936 A2 | 12/2012 |
| WO | 2014108810 A2 | 7/2014 |
| WO | 2014133905 A1 | 9/2014 |
| WO | 2015002813 A1 | 1/2015 |
| WO | 2015031849 A1 | 3/2015 |
| WO | 2016075204 A1 | 5/2016 |
| WO | 2017007753 A1 | 1/2017 |
| WO | 2017015018 A1 | 1/2017 |
| WO | 2017201198 A1 | 11/2017 |
| WO | 2018118092 A1 | 6/2018 |
| WO | 2018119063 A1 | 6/2018 |
| WO | 2018119101 A1 | 6/2018 |
| WO | 2021126503 A1 | 6/2021 |

OTHER PUBLICATIONS

ISA, "International Search Report and Written Opinion, PCT/US2019/036105", 17 pages, Sep. 24, 2019.

\* cited by examiner

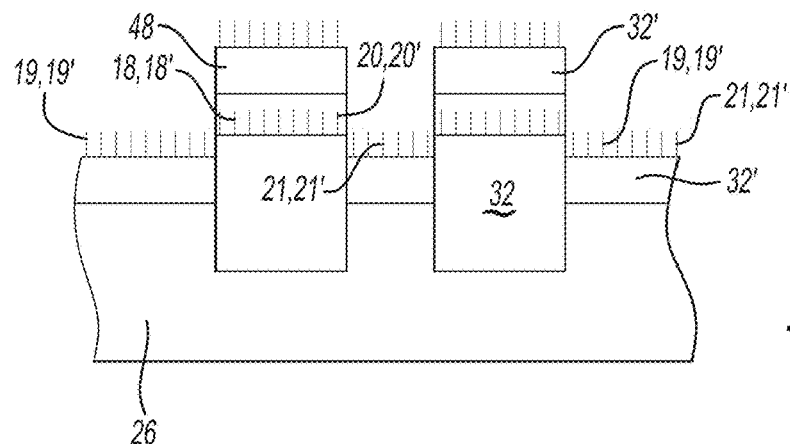
*Fig-8F*
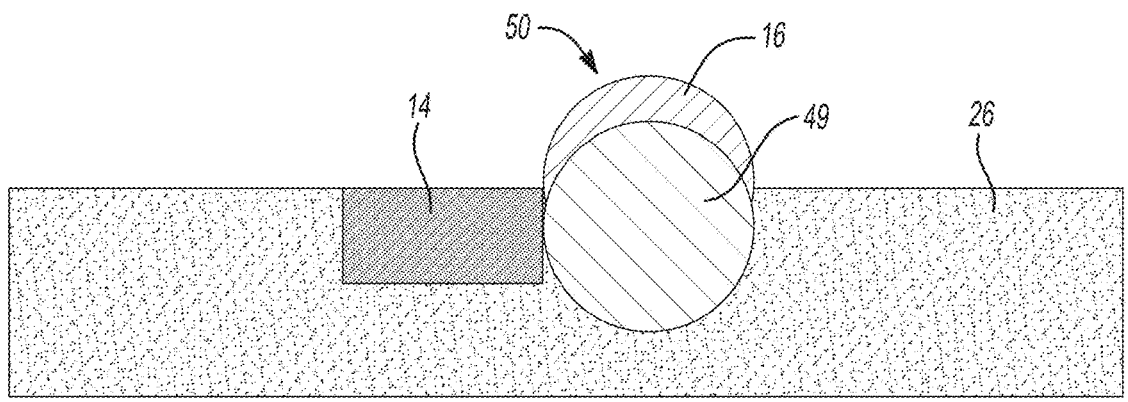
*Fig-9*
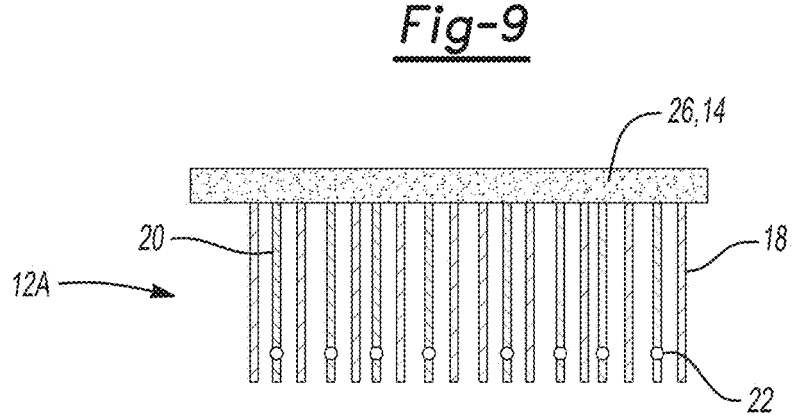
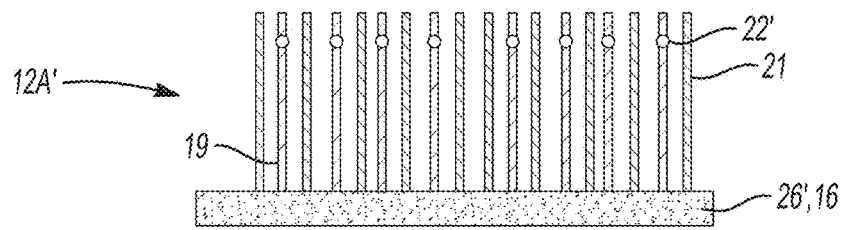
*Fig-10*

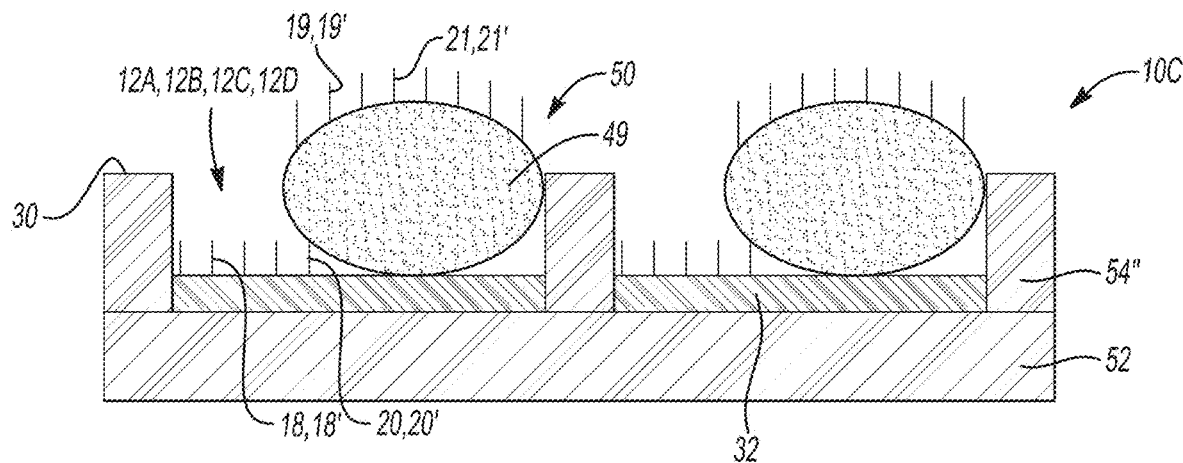
*Fig-18*
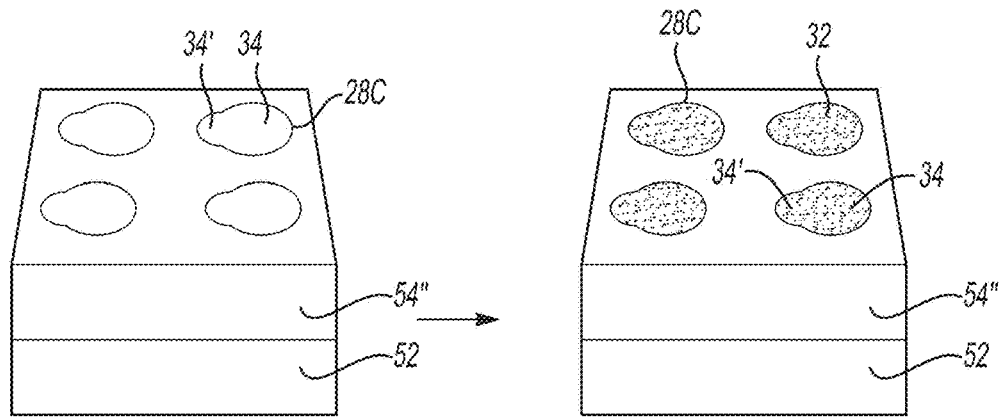
*Fig-19A*  *Fig-19B*
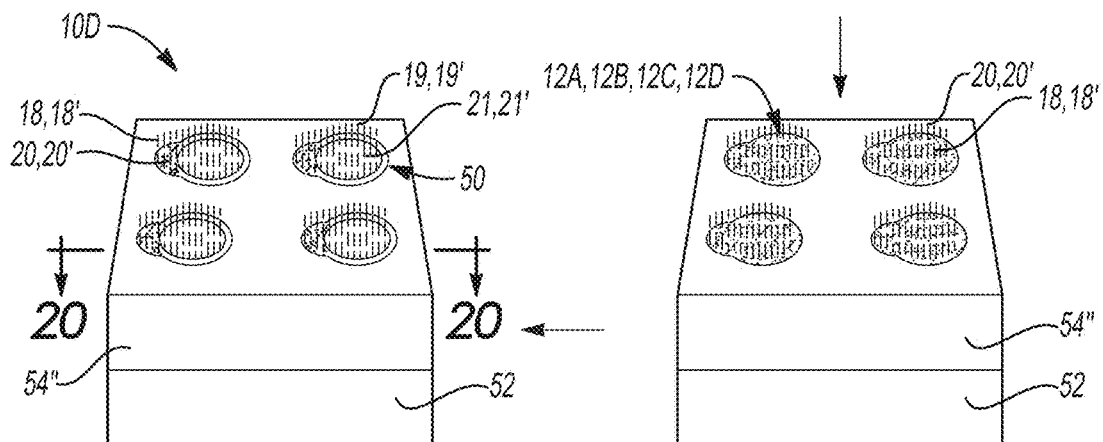
*Fig-19D*  *Fig-19C*

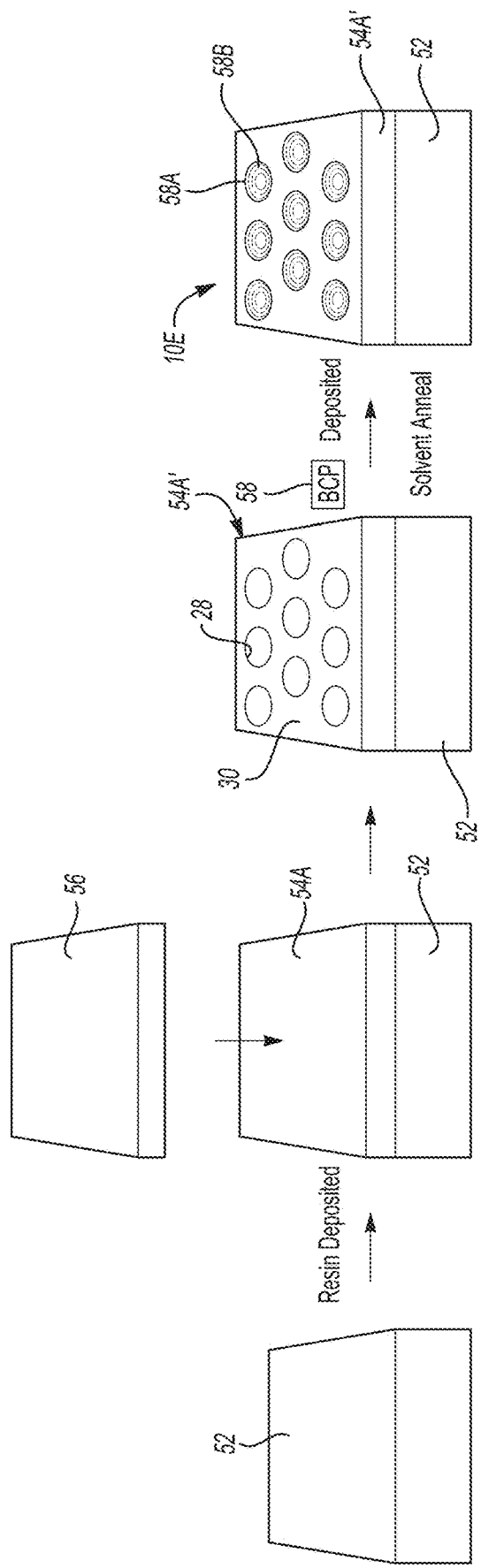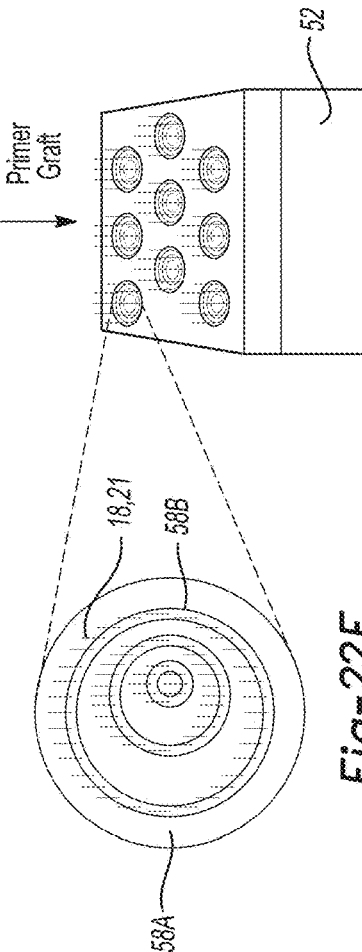

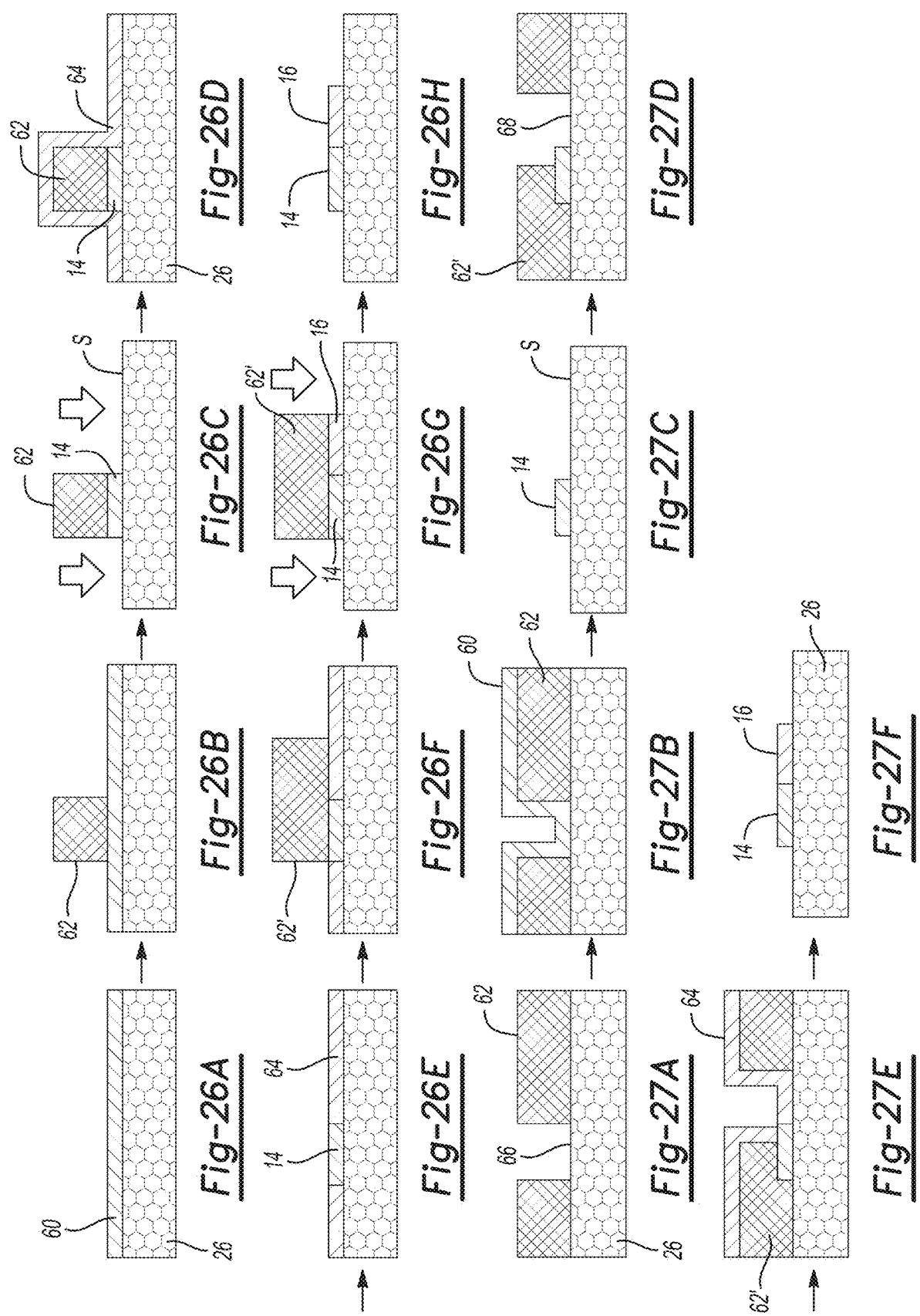

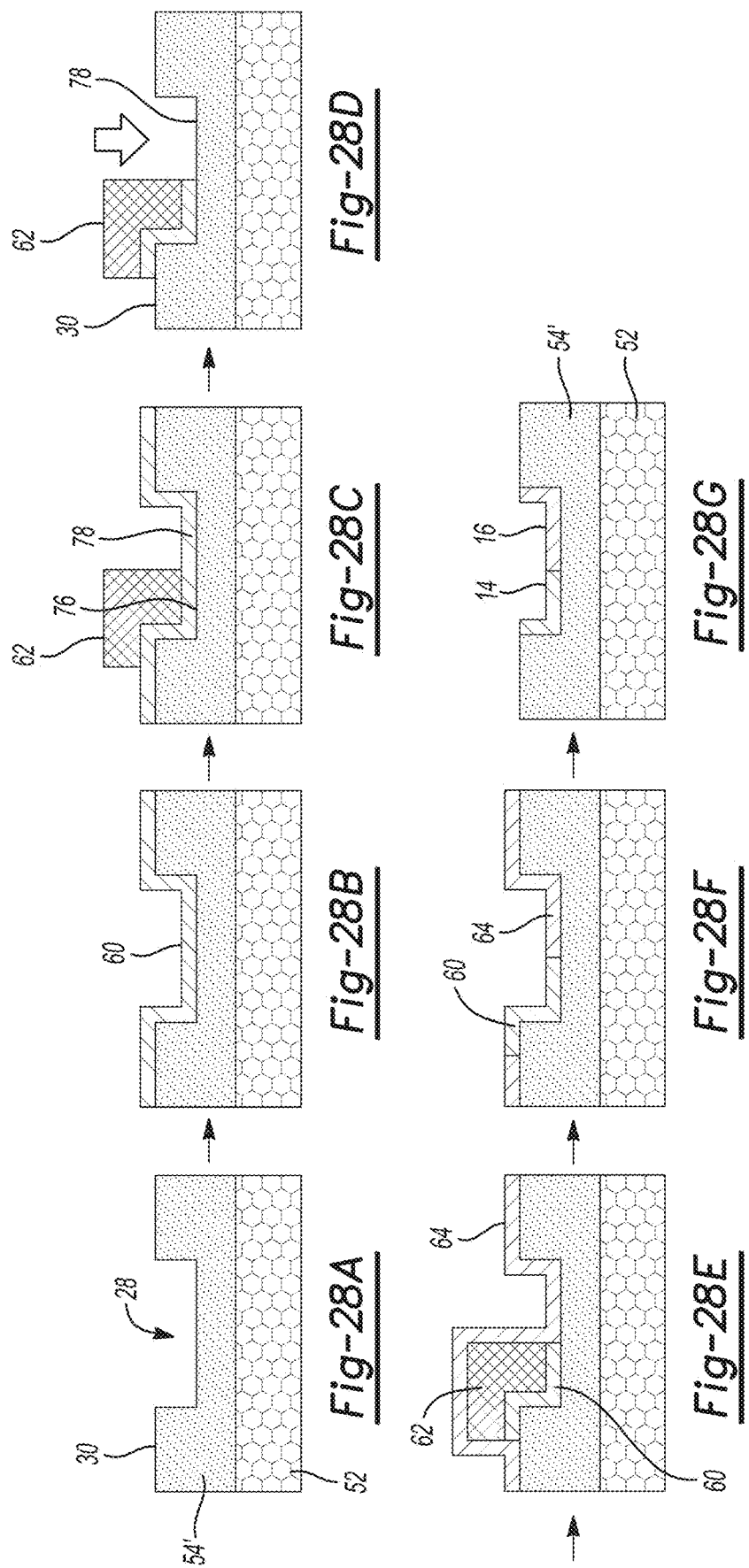

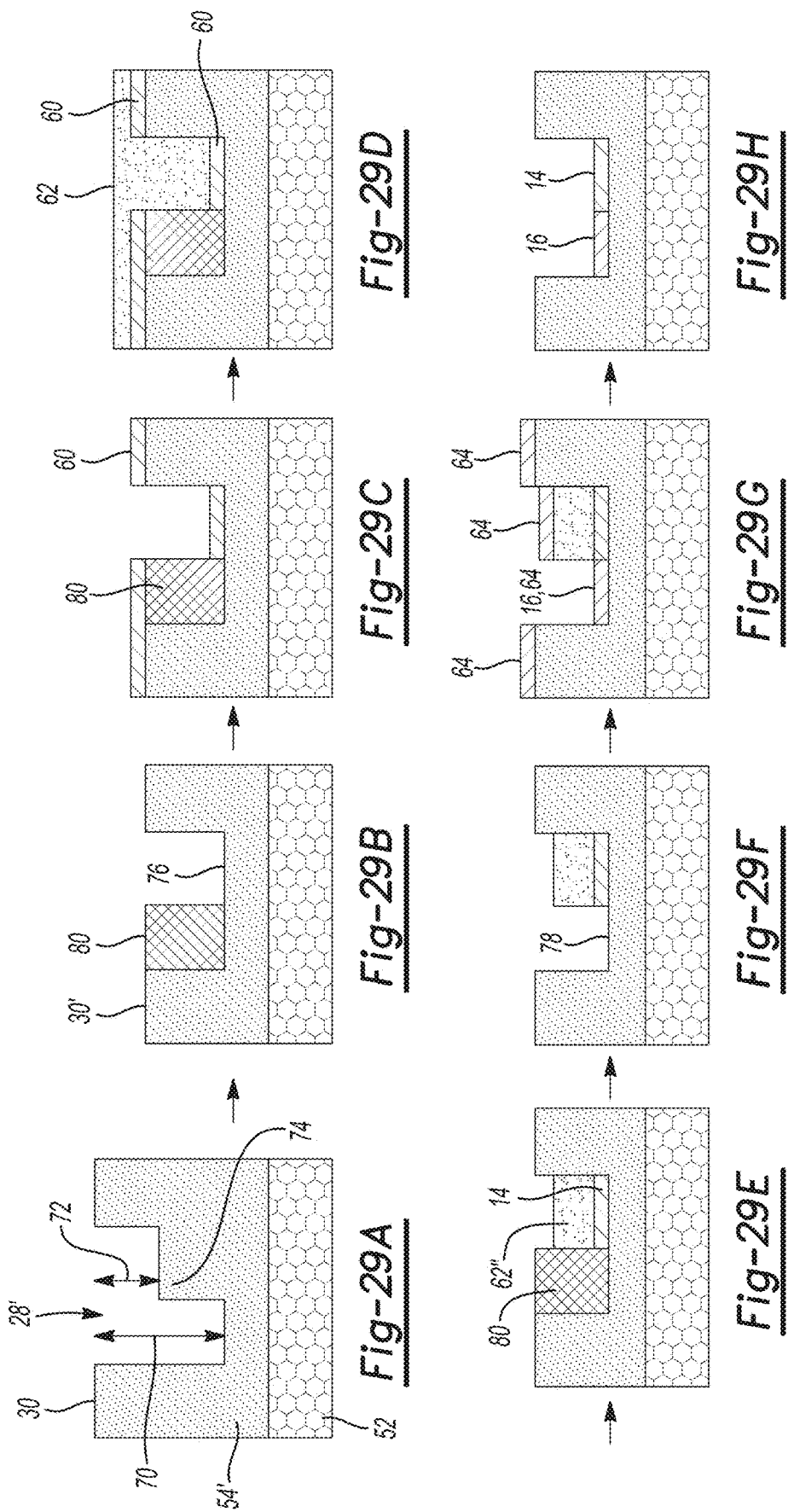

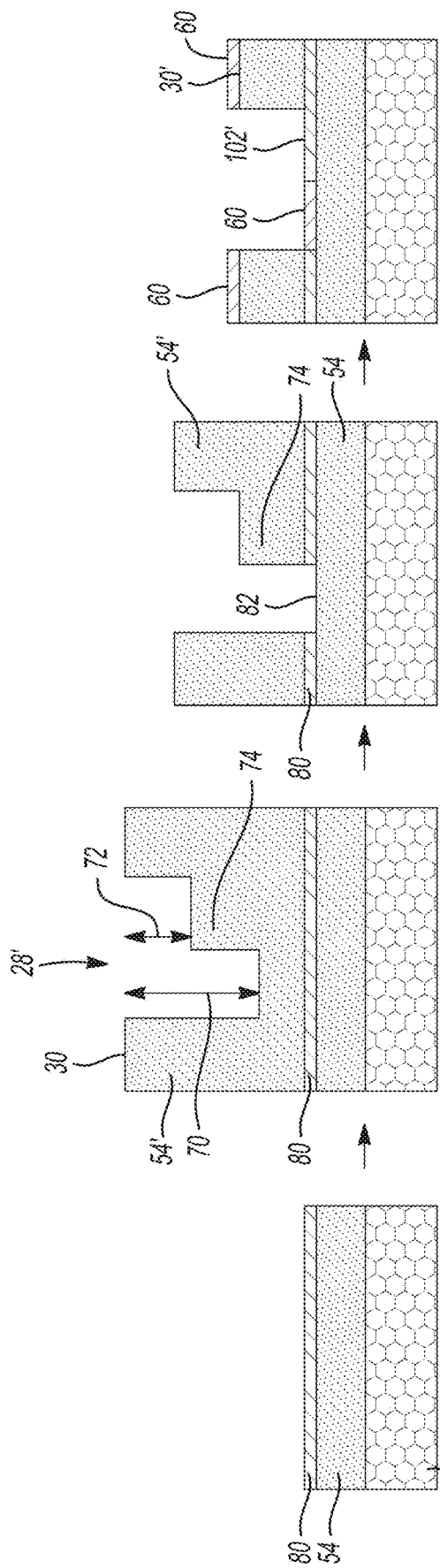
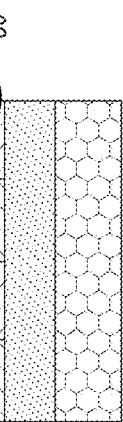
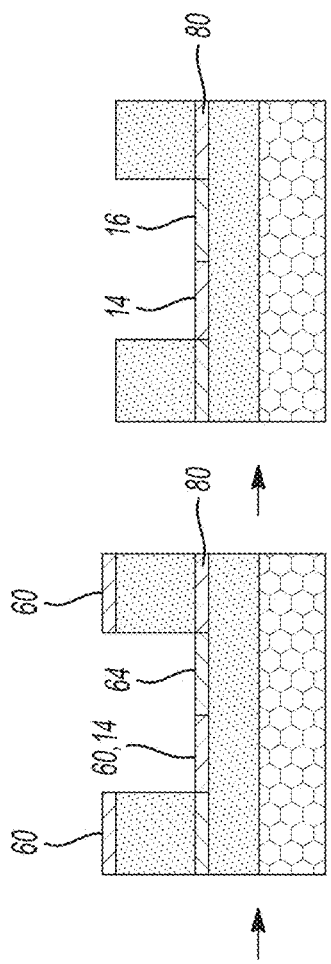

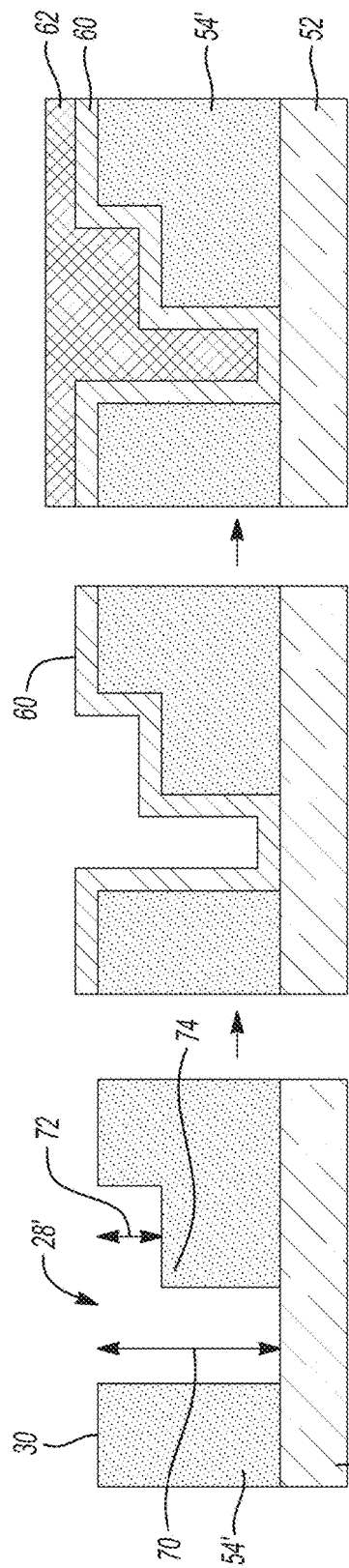
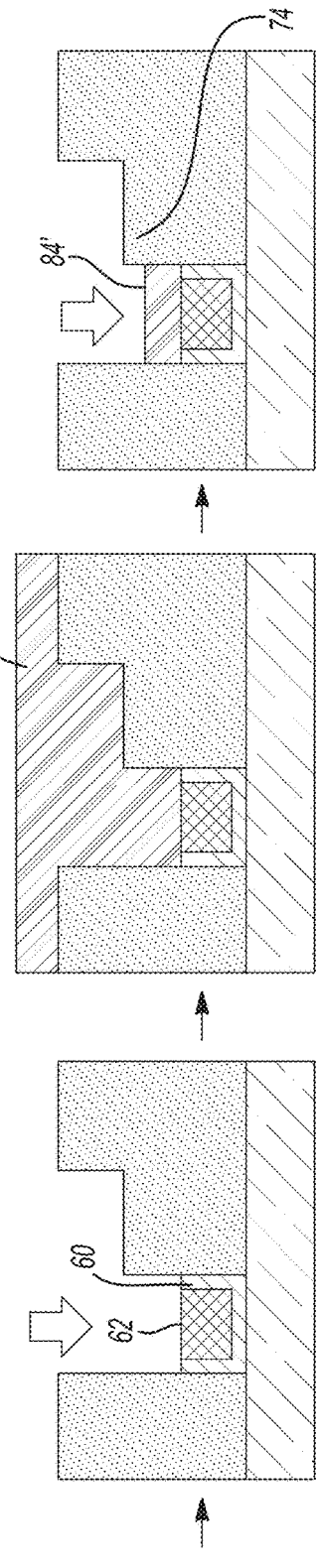
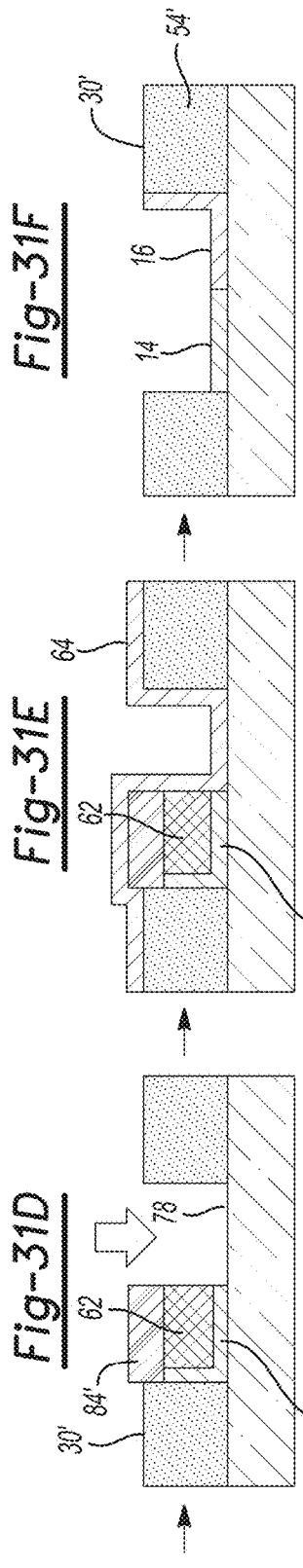
Fig-31A Fig-31B Fig-31C Fig-31D Fig-31E Fig-31F Fig-31G Fig-31H Fig-31I

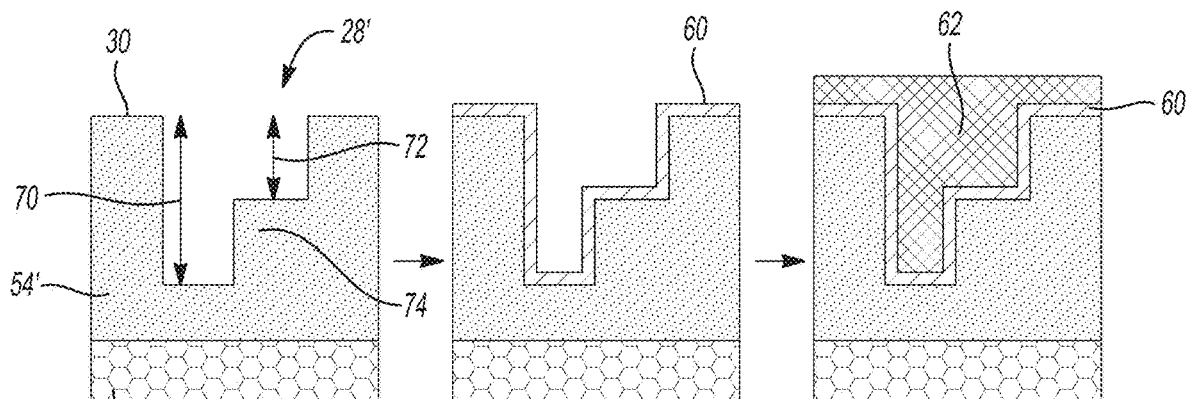
Fig-32A  Fig-32B  Fig-32C
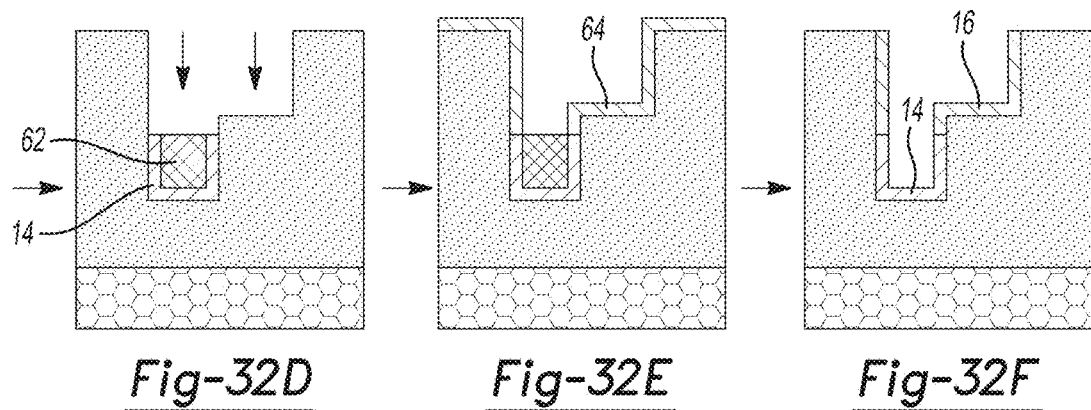
Fig-32D  Fig-32E  Fig-32F
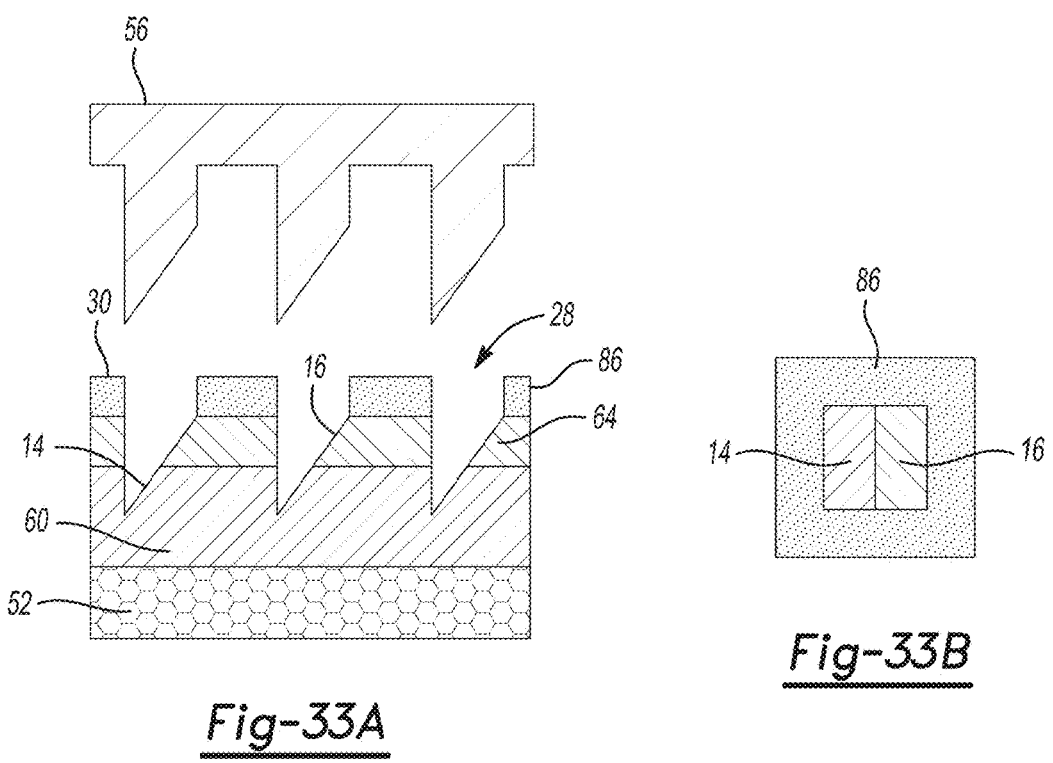
Fig-33A
Fig-33B

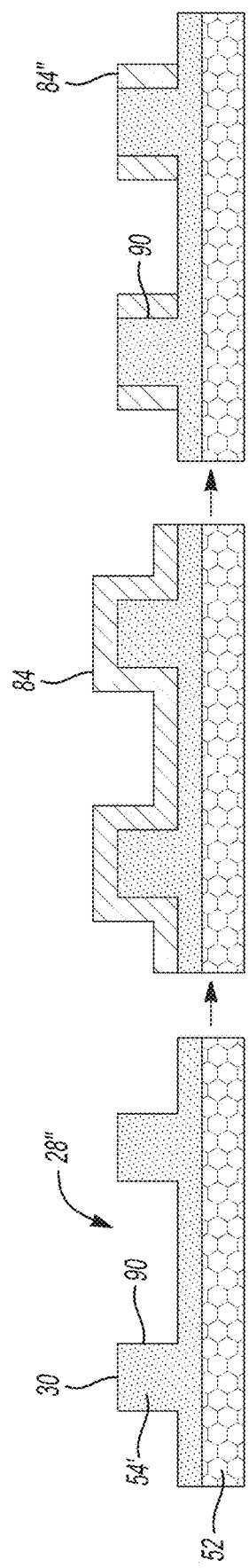
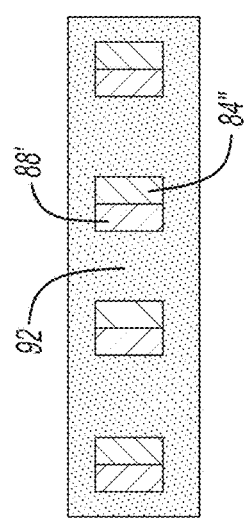
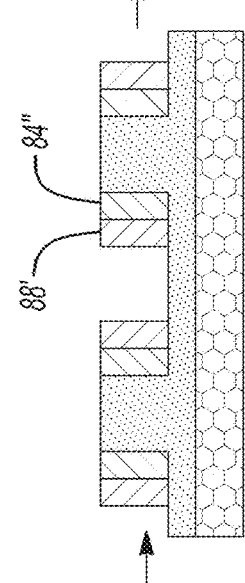
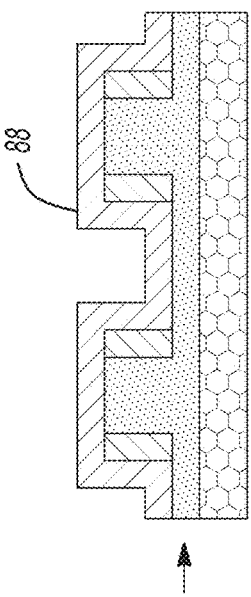
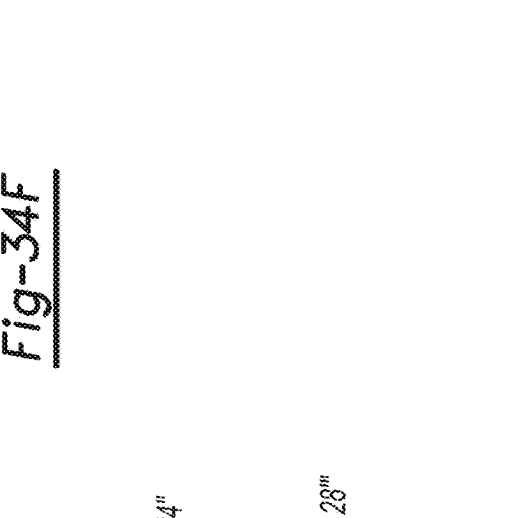
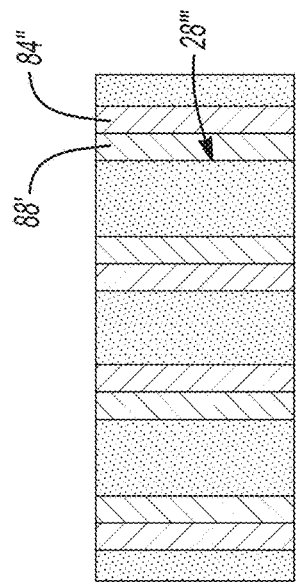
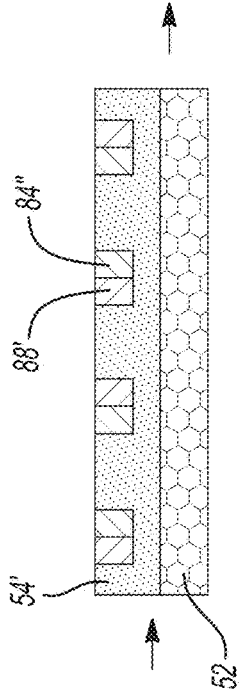

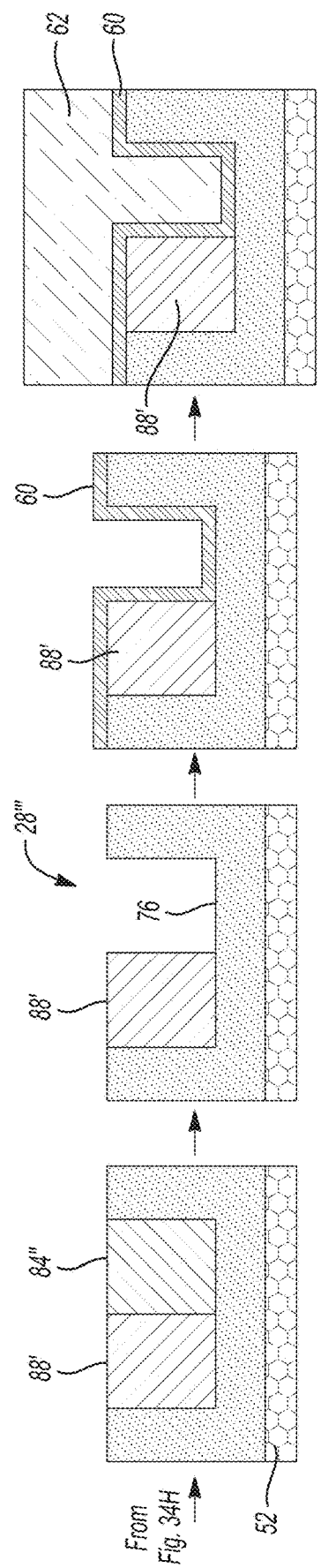
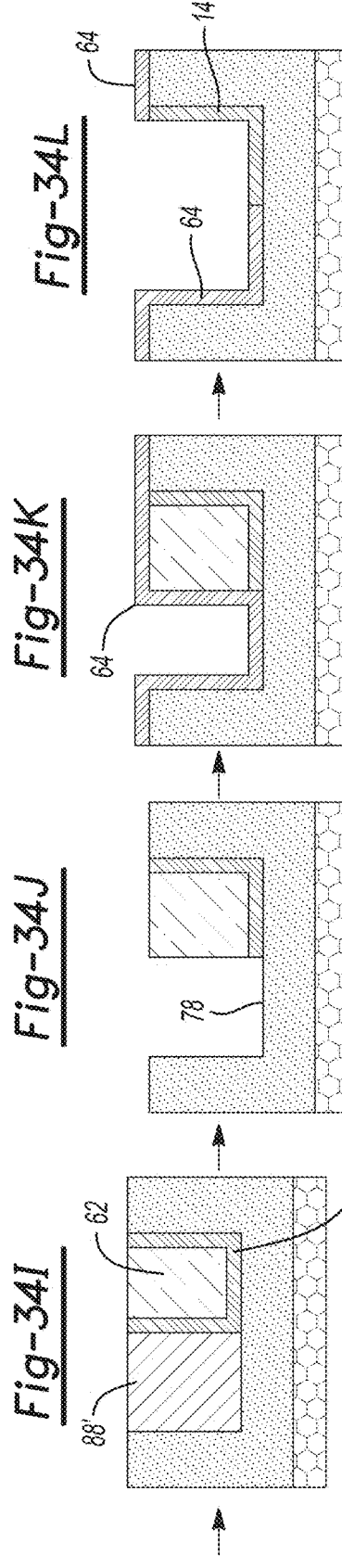
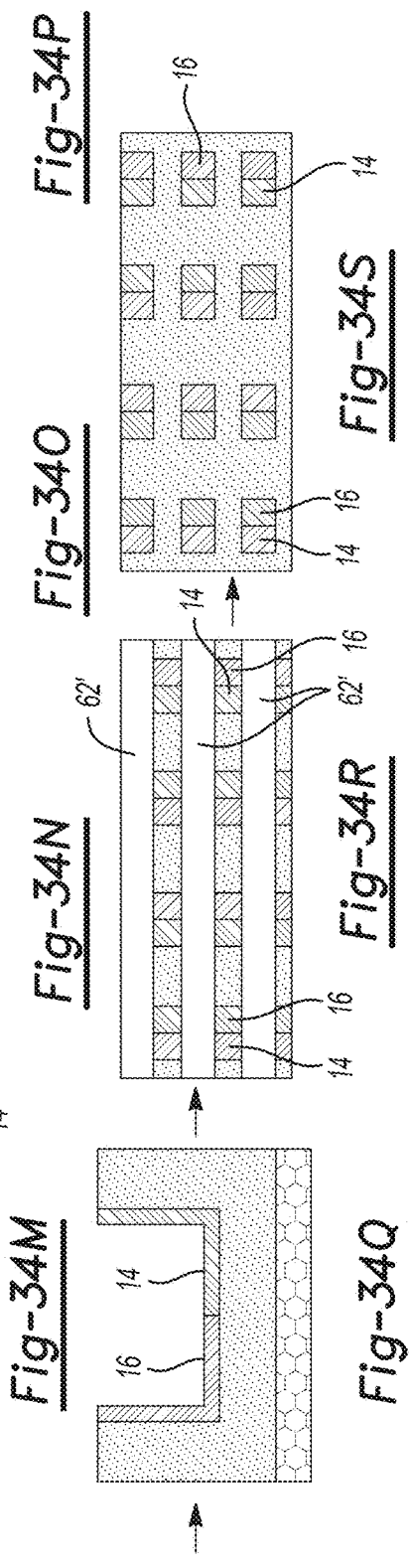

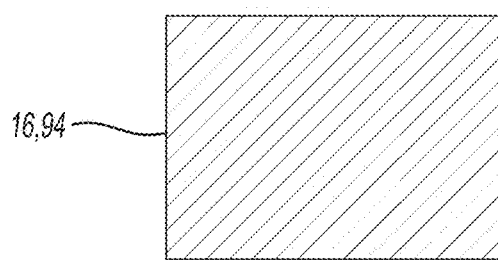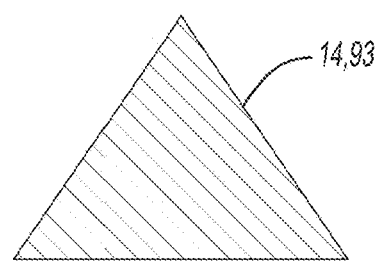
*Fig-35*
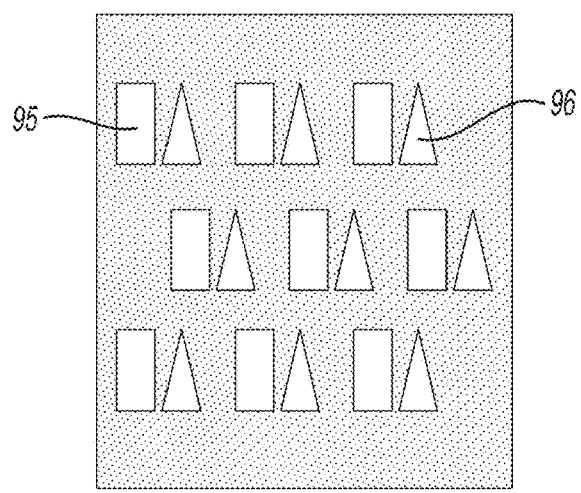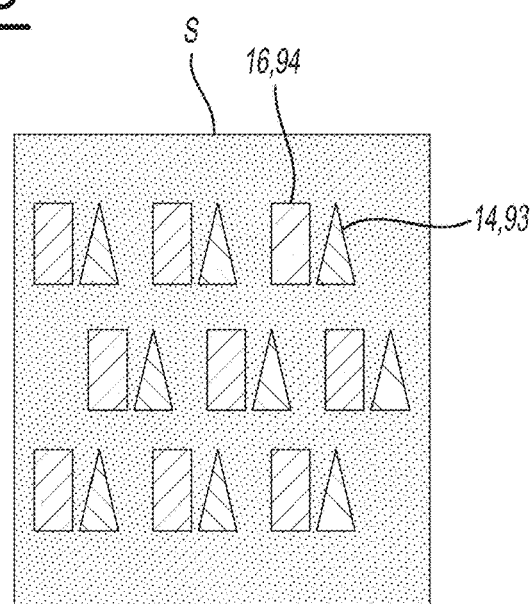
*Fig-36A*  *Fig-36B*
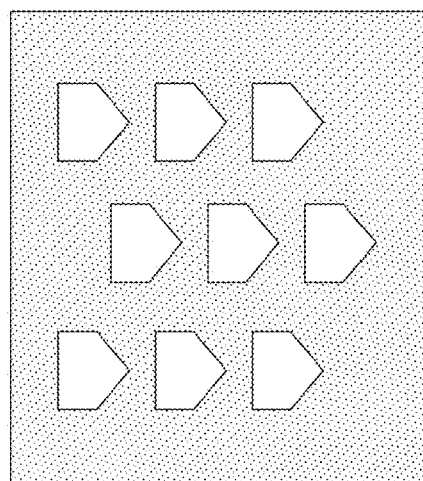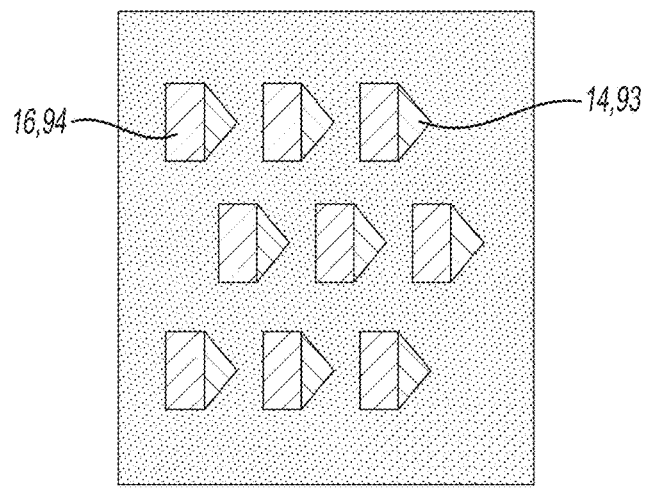
*Fig-37A*  *Fig-37B*

Anneal

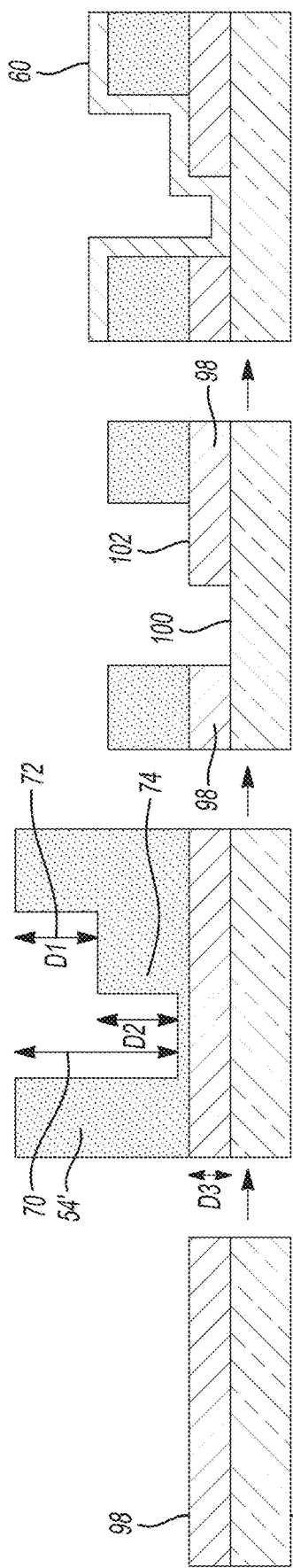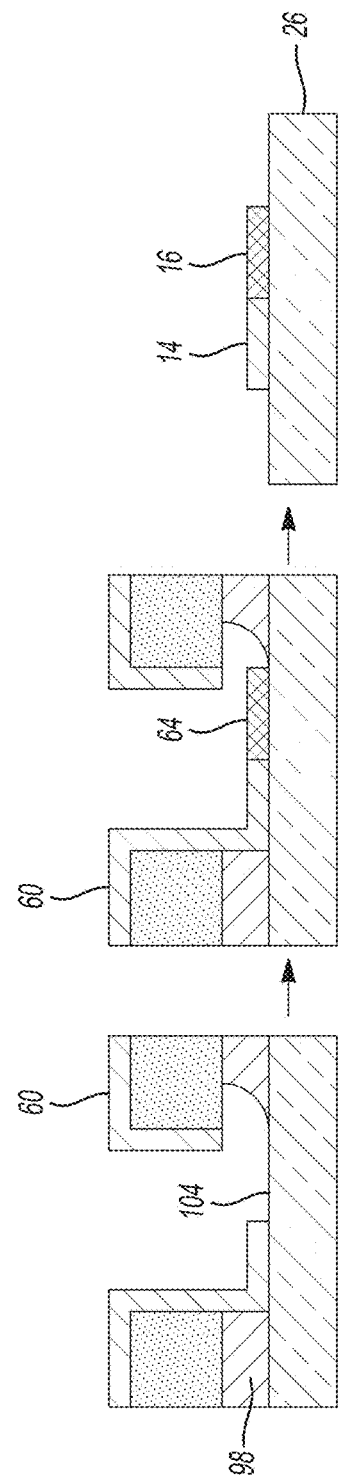

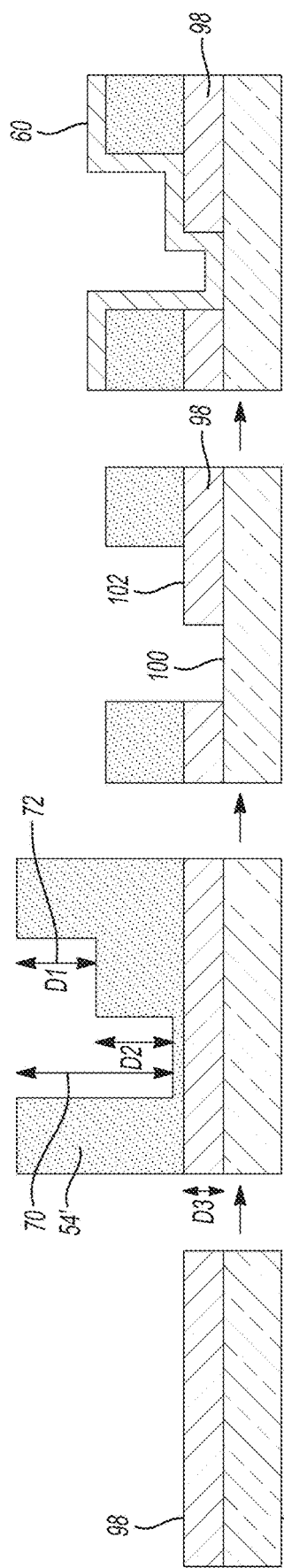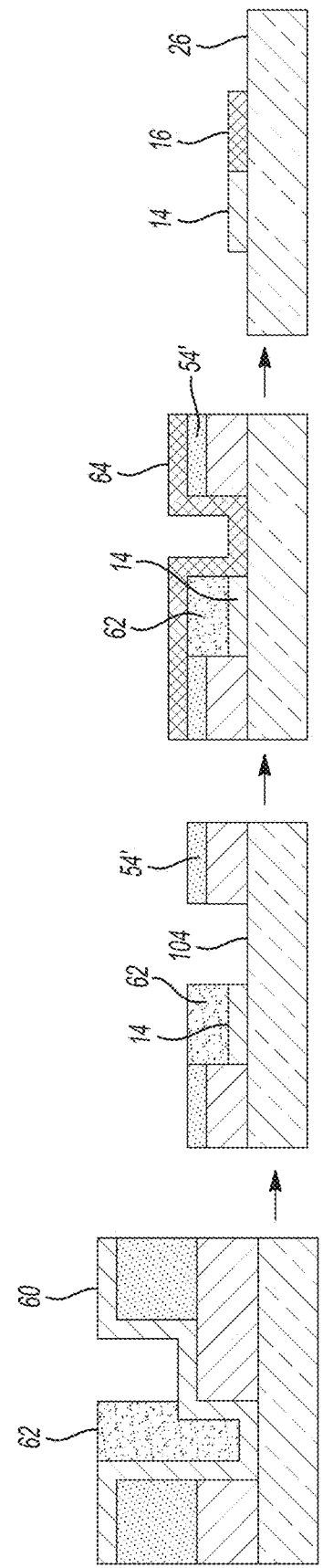

FLOW CELLS

CROSS-REFERENCE TO RELATED APPLICATIONS

This application is a continuation of U.S. application Ser. No. 17/840,569, filed Jun. 14, 2022, which is itself a continuation of U.S. application Ser. No. 17/139,834, filed Dec. 31, 2020, now U.S. Pat. No. 11,384,392 issued Jul. 12, 2022, which is itself a divisional of U.S. application Ser. No. 16/626,452, filed Dec. 24, 2019, now U.S. Pat. No. 11,124,829 issued Sep. 21, 2021, which is itself a national stage entry under 35 U.S.C. § 371 of PCT/US2019/036105, filed Jun. 7, 2019, which itself claims the benefit of U.S. Provisional Application Ser. No. 62/692,511, filed Jun. 29, 2018 and of U.S. Provisional Application Ser. No. 62/743,373, filed Oct. 9, 2018; the content of each of which is incorporated by reference herein in its entirety.

REFERENCE TO SEQUENCE LISTING

The Sequence Listing submitted herewith is hereby incorporated by reference in its entirety. The name of the file is ILI172DUS_IP-1806C-US_Sequence_Listing.xml, the size of the file is 2,788 bytes, and the date of creation of the file is May 10, 2023.

BACKGROUND

Some available platforms for sequencing nucleic acids utilize a sequencing-by-synthesis approach. With this approach, a nascent strand is synthesized, and the addition of each monomer (e.g., nucleotide) to the growing strand is detected optically and/or electronically. Because a template strand directs synthesis of the nascent strand, one can infer the sequence of the template DNA from the series of nucleotide monomers that were added to the growing strand during the synthesis. In some examples, paired-end sequencing may be used, where forward strands are sequenced and removed, and then reverse strands are constructed and sequenced.

INTRODUCTION

A first aspect disclosed herein is flow cell, comprising: a substrate; a first primer set attached to a first region on the substrate, the first primer set including an un-cleavable first primer and a cleavable second primer; and a second primer set attached to a second region on the substrate, the second primer set including a cleavable first primer and an un-cleavable second primer.

In an example of the first aspect, the first region includes a material having a first functional group; and the second region includes a material having a second functional group that is different than the first functional group.

In an example of the first aspect, the flow cell further comprises a gap separating the first primer set from the second primer set.

In an example of the first aspect, the substrate includes depressions separated by interstitial regions; and each of the depressions includes: the first region located at a first portion; and the second region located at a second portion. In one version of this example, the flow cell may further comprise a gap separating the first region from the second region. In another version of this example, the first region and the second region partially overlap. In still another version of this example, the first and second portions have different depths. In a further version of this example, the first and second regions are different blocks of a block copolymer.

In an example of the first aspect, the substrate includes depressions separated by interstitial regions; each of the depressions includes the first region; and the second region is located on at least some of the interstitial regions.

In an example of the first aspect, the first region includes a first polymer and the first primer set is grafted to the first polymer; and the second region includes a second polymer and the second primer set is grafted to the second polymer. In one version of this example, the flow cell further comprises a protective coating on the first primer set and on the first polymer. In another version of this example, the first polymer is a first layer on the substrate; the second polymer is a second layer on the first layer; the flow cell further comprises: a passivation resin on the second layer; and features defined in the passivation resin, the second polymer and the first polymer; and each of the first and second primer sets is exposed at each of the features.

In an example of the first aspect, the substrate includes depressions separated by interstitial regions; each of the depressions includes: a first portion where the first region is located; and a second portion; and the flow cell further comprises a bead located in the second portion, wherein the second region is at a surface of the bead.

In an example of the first aspect, the cleavable first primer includes a first cleavage site, the cleavable second primer includes a second cleavage site, and the first and second cleavage sites are of an identical type. In one version of this example, each of the un-cleavable first primer, the cleavable second primer, the cleavable first primer, and the cleavable second primer includes a respective linker; the first cleavage site of the first cleavable primer is located along its linker; and the second cleavage site of the second cleavable primer is located along its linker.

In an example of the first aspect, the cleavable first primer includes a first cleavage site, the cleavable second primer includes a second cleavage site, and the first and second cleavage sites are of a different type. In one version of this example, each of the un-cleavable first primer, the cleavable second primer, the cleavable first primer, and the cleavable second primer includes a respective linker; the first cleavage site of the first cleavable primer is located along its linker; and the second cleavage site of the second cleavable primer is located along its linker.

In an example of the first aspect, the first primer set is attached to a first support structure; the first region is a first capture site that is attached to the first support structure; the second primer set is attached to a second support structure that is different than the first support structure; and the second region is a second capture site that is attached to the second support structure.

It is to be understood that any features of the first aspect disclosed herein may be combined together in any desirable manner and/or configuration.

A second aspect disclosed herein is a flow cell comprising a first substrate; a first primer set attached to the first substrate, the first primer set including an un-cleavable first primer and a cleavable second primer; a second substrate opposed to the first substrate; and a second primer set attached to the second substrate, the second primer set including a cleavable first primer and an un-cleavable second primer.

It is to be understood that any features of the second aspect may be combined together in any desirable manner. Moreover, it is to be understood that any combination of features of the first aspect and/or of the second aspect may be used together, and/or may be combined with any of the examples disclosed herein.

A third aspect disclosed herein is a kit comprising a flow cell including: a substrate including depressions separated by interstitial regions; a first polymer layer in each of the depressions, wherein some functional groups of the first polymer layer are capped; a first primer set attached to other functional groups of first polymer layer in each of the depressions; and a second polymer layer on the interstitial regions; and a priming fluid including: a fluid carrier; and a second primer set that is different from the first primer set.

In an example of the third aspect, the first primer set includes an un-cleavable first primer and a cleavable second primer; and the second primer set includes a cleavable first primer and an un-cleavable second primer.

It is to be understood that any features of the third aspect may be combined together in any desirable manner. Moreover, it is to be understood that any combination of features of the third aspect and/or of the second aspect and/or of the first aspect may be used together, and/or may be combined with any of the examples disclosed herein.

A fourth aspect disclosed herein is a method comprising introducing a template fluid to a flow cell including: a substrate including depressions separated by interstitial regions; a first polymer layer in each of the depressions, wherein exposed functional groups of the first polymer layer are capped; a first primer set attached to the first polymer layer in each of the depressions, the first primer set including a cleavable first primer and an un-cleavable second primer; and a second polymer layer on the interstitial regions; whereby a template from the template fluid is amplified to form a cluster in at least some of the depressions; introducing a priming fluid, including an un-cleavable first primer and a cleavable second primer, to the flow cell, whereby the un-cleavable first primer and the cleavable second primer graft to the second polymer layer; and initiating bridge amplification from the cluster to the un-cleavable first primer and a cleavable second primer, thereby forming a second cluster on at least some of the interstitial regions.

It is to be understood that any features of the fourth aspect may be combined together in any desirable manner. Moreover, it is to be understood that any combination of features of the fourth aspect and/or of the third aspect and/or of the second aspect and/or of the first aspect may be used together, and/or may be combined with any of the examples disclosed herein.

A fifth aspect disclosed herein is a method, comprising: introducing a template fluid to a flow cell including: a substrate including depressions separated by interstitial regions; a first polymer layer in each of the depressions; a first primer set attached to the first polymer layer, the first primer set including a cleavable first primer and an un-cleavable second primer; an optional protective coating layer on the first polymer layer and on the first primer set; a second polymer layer on the interstitial regions; and a second primer set attached to the second polymer layer, the second primer set including an un-cleavable first primer and a cleavable second primer; whereby a template from the template fluid is amplified to form a cluster in at least some of the depressions and on at least some of the interstitial regions; and cleaving the cleavable first primer and the cleavable second primer.

It is to be understood that any features of the fifth aspect may be combined together in any desirable manner. Moreover, it is to be understood that any combination of features of the fifth aspect and/or of the third aspect and/or of the second aspect and/or of the first aspect may be used together, and/or may be combined with any of the examples disclosed herein.

A sixth aspect disclosed herein is a flow cell comprising a support; a patterned resin on the support, the patterned resin including first depressions and second depressions separated by interstitial regions, the first depressions having smaller opening dimensions than the second depressions; a first primer set attached in at least some of the first depressions; and a functionalized bead respectively positioned in at least some of the second depressions, the functionalized bead including a second primer set attached at a surface of a core structure, wherein the second primer set is different than the first primer set.

In an example of the sixth aspect, the core structure of the functionalized bead is selected from the group consisting of silicon dioxide, a superparamagnetic material, polystyrene, and an acrylate.

In an example of the sixth aspect, the patterned resin is selected from the group consisting of a polyhedral oligomeric silsesquioxane resin (POSS)-based resin, an epoxy resin, a poly(ethylene glycol) resin, a polyether resin, an acrylic resin, an acrylate resin, a methacrylate resin, and combinations thereof.

In an example of the sixth aspect, the flow cell further comprises a polymer in the first depressions and in the second depressions, and wherein the first primer set is attached to the polymer in the at least some of the first depressions. In one version of this example, the functionalized bead is positioned on the polymer in the at least some of the second depressions. In another version of this example, the first primer set is also attached to the polymer in the at least some of the second depressions; and the functionalized bead is positioned on the first primer set in the at least some of the second depressions.

In an example of the sixth aspect, the first primer set includes a first primer and a uracil-modified second primer; and the second primer set includes a uracil-modified first primer and a second primer.

It is to be understood that any features of the sixth aspect disclosed herein may be combined together in any desirable manner and/or configuration.

A seventh aspect disclosed herein is a flow cell comprising a support; a patterned resin on the support, the patterned resin including depressions separated by interstitial regions; a first primer set attached to at least some of the depressions; and a functionalized bead positioned in the at least some of the depressions so that at least some primers of the first primer set are exposed, the functionalized bead including a second primer set attached at a surface of a core structure, wherein the second primer set is different than the first primer set.

In an example of the seventh aspect, each of the depressions includes a first portion with a first opening dimension that is larger than or equal to a diameter of the functionalized bead, and a second portion with a second opening dimension that is smaller than the diameter of the functionalized bead; and the functionalized bead is positioned in the first portion of each of the at least some of the depressions.

In an example of the seventh aspect, the core structure of the functionalized bead is selected from the group consisting of silicon dioxide, a superparamagnetic material, polystyrene, and an acrylate.

In an example of the seventh aspect, the patterned resin is selected from the group consisting of a polyhedral oligomeric silsesquioxane resin (POSS)-based resin, an epoxy resin, a poly(ethylene glycol) resin, a polyether resin, an acrylic resin, an acrylate resin, a methacrylate resin, and combinations thereof.

In an example of the seventh aspect, the flow cell further comprises a polymer in the depressions. In one version of this aspect, the first primer set is attached to a portion of the polymer unoccupied by the functionalized bead. In one example of this version, the first primer set is attached to the polymer in the depressions; and the functionalized bead is positioned on some other primers of the first primer set.

It is to be understood that any features of the seventh aspect disclosed herein may be combined together in any desirable manner and/or configuration.

An eighth aspect disclosed herein is a method comprising selectively applying a polymer in depressions of a patterned resin on a support; grafting a first primer set to the polymer in at least some of the depressions; and before or after grafting the first primer set, depositing functionalized beads i) in a portion of each of the at least some of the depressions, or ii) in second depressions having larger opening dimensions than the at least some of the depressions, the functionalized beads including a second primer set attached at a surface of a core structure, wherein the first and second primer sets are different.

In an example of the eighth aspect, wherein prior to depositing the functionalized beads, the method further comprises forming the functionalized beads by attaching the second primer set to the core structure.

In an example of the eighth aspect, the portion of each of the at least some of the depressions has an opening dimension that is larger than or equal to a diameter of each of the functionalized beads; the at least some of the depressions include a second portion interconnected with the portion, where the second portion has a second opening dimension that is smaller than the diameter of each of the functionalized beads; and the functionalized beads self-assemble into the portion of each of the at least some of the depressions by size exclusion.

In an example of the eighth aspect, wherein prior to selectively applying the polymer, the method further comprises forming the patterned resin on the support by: depositing a resin on the support; and patterning the resin using nanoimprint lithography.

It is to be understood that any features of the eighth aspect may be combined together in any desirable manner. Moreover, it is to be understood that any combination of features of the eighth aspect and/or of the seventh aspect and/or of the sixth aspect and/or of the first aspect may be used together, and/or may be combined with any of the examples disclosed herein.

A ninth aspect disclosed herein is a flow cell comprising a support; a patterned resin on the support, the patterned resin including depressions separated by interstitial regions; a block copolymer on the patterned resin in the depressions, each block of the block copolymer having a block-specific functional group that is different from the block-specific functional group of each other block of the block copolymer; and a primer attached to the block-specific functional group of at least one of the blocks.

In an example of the ninth aspect, the patterned resin is selected from the group consisting of a polyhedral oligomeric silsesquioxane resin (POSS)-based resin, an epoxy resin, a poly(ethylene glycol) resin, a polyether resin, an acrylic resin, an acrylate resin, a methacrylate resin, and combinations thereof. In one version of this example, the patterned resin is the POSS-based resin, and wherein the POSS-based resin is a cross-linked epoxy POSS resin. In another version of this example, the block copolymer includes: a first block including an acrylamide monomer having an amino group as its block-specific functional group; and a second block including an azido acetamido pentyl acrylamide monomer having an azido group as its block-specific functional group. In an example of this other version, the block copolymer is:

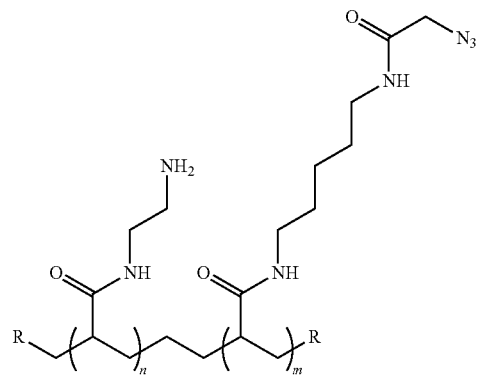

wherein R is hydrogen or a polymer initiating species end group, n ranges from 1 to 10,000, and m ranges from 1 to 10,000. In still another version of this example, the block copolymer is:

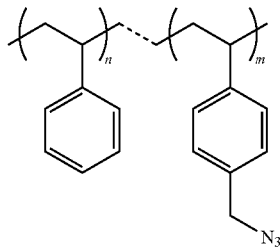

wherein n ranges from 1 to 10,000, and m ranges from 1 to 10,000.

In an example of the ninth aspect, the patterned resin is an amorphous fluoropolymer. In one version of this example, the block copolymer includes: a first block including a monomer having a trifluoromethyl group as its block-specific functional group; and a second block including a monomer having a primer-grafting functional group as its block-specific functional group.

In an example of the ninth aspect, the block copolymer includes: a first block including a monomer having a primer-grafting functional group as its block-specific functional group; and a second block including a monomer to adjust an interaction parameter to drive phase separation of the first and second blocks. In one version of this example, the primer-grafting functional group is an azido group; and the block-specific functional group of the monomer of the second block is selected from the group consisting of an amino group, an alcohol group, an aryl group, and a charged group.

In an example of the ninth aspect, the block copolymer is a terpolymer including a first block, a second block, and a third block; the block-specific functional group of the first block is attached to the patterned resin; the block-specific functional group of the second block is attached to the primer; and the block-specific functional group of the third block is attached to an other primer that is different than the primer, or to an enzyme.

In an example of the ninth aspect, the block copolymer is a terpolymer including a first block, a second block, and a third block; the block-specific functional group of the first block is attached to the patterned resin; the block-specific functional group of the second block is attached to the primer; and the block-specific functional group of the third block affects a surface free energy of the block copolymer or affects stability of the block copolymer.

In an example of the ninth aspect, wherein the depressions are selected from the group consisting of wells and trenches.

In an example of the ninth aspect, the patterned resin and the block copolymer each have a surface free energy within a range of from about 25 mN/m to about 50 mN/m.

It is to be understood that any features of the ninth aspect disclosed herein may be combined together in any desirable manner and/or configuration. Moreover, it is to be understood that any combination of features of the ninth aspect and/or of the first aspect may be used together, and/or may be combined with any of the examples disclosed herein.

A tenth aspect disclosed herein is a flow cell comprising a support; a patterned polyhedral oligomeric silsesquioxane (POSS)-based resin on the support, the patterned POSS-based resin including depressions separated by interstitial regions; segregated block copolymer on the patterned POSS-based resin in the depressions, wherein one block of the segregated block copolymer has a functional group attached to the patterned POSS-based resin and an other block of the segregated block copolymer has an other functional group; and a primer attached to the other functional group.

In an example of the tenth aspect, the segregated block copolymer is selected from the group consisting of:

i)

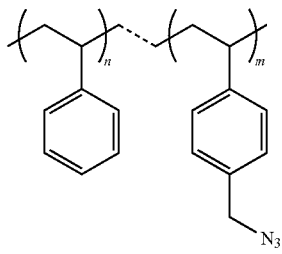

wherein n ranges from 1 to 10,000, and m ranges from 1 to 10,000; and ii)

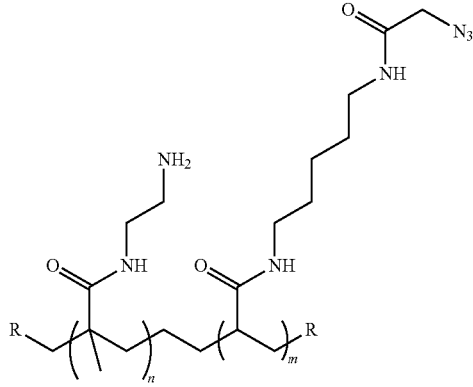

wherein R is hydrogen or a polymer initiating species end group, n ranges from 1 to 10,000, and m ranges from 1 to 10,000.

It is to be understood that any features of the tenth aspect disclosed herein may be combined together in any desirable manner and/or configuration. Moreover, it is to be understood that any combination of features of the tenth aspect and/or of the ninth aspect and/or of the first aspect may be used together, and/or may be combined with any of the examples disclosed herein.

An eleventh aspect disclosed herein is a method comprising patterning a resin to form a patterned resin including depressions separated by interstitial regions; introducing a solution including a block copolymer on the patterned resin, each block of the block copolymer having a block-specific functional group that is different from the block-specific functional group of each other block of the block copolymer; exposing the solution to solvent vapor annealing, whereby the block copolymer phase separates and self-assembles in the depressions; and grafting a primer to the block-specific functional group of at least one of the blocks.

In an example of the eleventh aspect, patterning the resin involves nano-imprint lithography.

In an example of the eleventh aspect, the solution including the block copolymer has a Flory-Huggins interaction parameter ranging from about 0.04 to about 0.30.

In an example of the eleventh aspect, wherein prior to grafting, the method further comprises exposing the patterned resin, including the phase separated and self-assembled block copolymer in the depressions, to a curing process.

It is to be understood that any features of the eleventh aspect disclosed herein may be combined together in any desirable manner and/or configuration. Moreover, it is to be understood that any combination of features of the eleventh aspect and/or of the tenth aspect and/or of the ninth aspect and/or of the first aspect may be used together, and/or may be combined with any of the examples disclosed herein.

A twelfth aspect disclosed herein is a method comprising applying a first functionalized layer on a substrate; patterning the first functionalized layer, thereby forming a first functionalized region covered by a photoresist; applying a second functionalized layer on the photoresist and portions of the substrate; lifting off the photoresist and any of the second functionalized layer thereon; removing a portion of the second functionalized layer, thereby forming a second functionalized region adjacent to the first functionalized region; and attaching a first primer set to the first functionalized layer or the first functionalized region and a second primer set to the second functionalized layer or the second functionalized region, wherein the first primer set is different from the second primer set.

In an example of the twelfth aspect, the attaching of the first primer set involves pre-grafting an un-cleavable first primer and a cleavable second primer to the first functionalized layer before the first functionalized layer is applied; and the attaching of the second primer set involves pre-grafting a cleavable first primer and an un-cleavable second primer to the second functionalized layer before the second functionalized layer is applied.

In an example of the twelfth aspect, the attaching of the first primer set involves grafting an un-cleavable first primer and a cleavable second primer to the first functionalized layer after its application; and the attaching of the second primer set involves grafting a cleavable first primer and an un-cleavable second primer to the second functionalized layer after its application.

In an example of the twelfth aspect, the method further comprises: depositing, respectively, a first self-assembled monolayer on the first functionalized region and a second self-assembled monolayer on the second functionalized region; wherein the attaching of the first primer set includes grafting an un-cleavable first primer and a cleavable second primer to the first self-assembled monolayer; and wherein the attaching of the second primer set includes grafting a cleavable first primer and an un-cleavable second primer to the second self-assembled monolayer.

In an example of the twelfth aspect, wherein the removing involves: applying a second photoresist on the first functionalized region and a second portion of the second functionalized layer that is to become the second functionalized region; and etching the portion of the second functionalized layer.

In an example of the twelfth aspect, the substrate includes a resin on a support; the resin includes depressions separated by interstitial regions; the first functionalized region is on a first portion of each depression; the second functionalized layer is on a second portion of each depression and on the interstitial regions; and the removing involves polishing the second functionalized layer from the interstitial regions.

In an example of the twelfth aspect, the substrate includes a resin on a support; the resin includes multi-level depressions separated by interstitial regions; the first functionalized region is at a first level of each multi-level depression; and prior to applying the second functionalized layer, the method further comprises: applying a sacrificial layer on the photoresist and portions of the resin; removing the sacrificial layer from the portions of the resin; and removing a region of the resin from the multi-layer depression to create an area that is adjacent to the first functionalized region; and the second functionalized layer is applied on the sacrificial layer on the photoresist, on the area, and on the interstitial regions.

It is to be understood that any features of the twelfth aspect disclosed herein may be combined together in any desirable manner and/or configuration. Moreover, it is to be understood that any combination of features of the twelfth aspect and/or of the first aspect and/or of the second aspect may be combined with any of the examples disclosed herein.

A thirteenth aspect disclosed herein is a method comprising applying a first photoresist on a substrate so that a first substrate portion is exposed; applying a first functionalized layer on the photoresist and the first substrate portion; lifting off the photoresist and any of the first functionalized layer thereon, thereby forming a first functionalized region on the first substrate portion; applying a second photoresist on the first functionalized region and on the substrate so that a second substrate portion adjacent to the first functionalized region is exposed; applying a second functionalized layer on the second photoresist and the second substrate portion; lifting off the second photoresist and any of the second functionalized layer thereon, thereby forming a second functionalized region adjacent to the first functionalized region; and attaching a first primer set to the first functionalized layer or the first functionalized region and a second primer set to the second functionalized layer or the second functionalized region, wherein the first primer set is different from the second primer set.

In an example of the thirteenth aspect, the attaching of the first primer set involves pre-grafting an un-cleavable first primer and a cleavable second primer to the first functionalized layer before the first functionalized layer is applied; and the attaching of the second primer set involves pre-grafting a cleavable first primer and an un-cleavable second primer to the second functionalized layer before the second functionalized layer is applied.

In an example of the thirteenth aspect, the attaching of the first primer set involves grafting an un-cleavable first primer and a cleavable second primer to the first functionalized layer after its application; and the attaching of the second primer set involves grafting a cleavable first primer and an un-cleavable second primer to the second functionalized layer after its application.

In an example of the thirteenth aspect, the method further comprises depositing, respectively, a first self-assembled monolayer on the first functionalized region and a second self-assembled monolayer on the second functionalized region; wherein the attaching of the first primer set includes grafting an un-cleavable first primer and a cleavable second primer to the first self-assembled monolayer; and wherein the attaching of the second primer set includes grafting a cleavable first primer and an un-cleavable second primer to the second self-assembled monolayer.

It is to be understood that any features of the thirteenth aspect disclosed herein may be combined together in any desirable manner and/or configuration. Moreover, it is to be understood that any combination of features of the thirteenth aspect and/or of the first aspect and/or of the second aspect may be combined with any of the examples disclosed herein.

A fourteenth aspect disclosed herein is a method comprising applying a first functionalized layer on a substrate including trenches separated by interstitial regions and a sacrificial material region in a first portion of each of the trenches; patterning the first functionalized layer, thereby forming a first functionalized region covered by a photoresist in a second portion of each of the trenches; removing the sacrificial material region to expose the first portion of each of the trenches; applying a second functionalized layer on the interstitial regions, on the first portion, and on the photoresist; lifting off the photoresist and any of the second functionalized layer thereon; removing any of the second functionalized layer from the interstitial regions, whereby a second functionalized region remains in the first portion of each of the trenches; applying a second photoresist in a pattern of spatially separated stripes that are at least substantially perpendicular to the trenches; removing portions of the first functionalized regions and the second functionalized regions that are exposed between the spatially separated stripes; removing the second photoresist; and attaching a first primer set to the first functionalized layer or the first functionalized regions and a second primer set to the second functionalized layer or the second functionalized regions, wherein the first primer set is different from the second primer set.

In an example of the fourteenth aspect, the attaching of the first primer set involves pre-grafting an un-cleavable first primer and a cleavable second primer to the first functionalized layer before the first functionalized layer is applied; and the attaching of the second primer set involves pre-grafting a cleavable first primer and an un-cleavable second primer to the second functionalized layer before the second functionalized layer is applied.

In an example of the fourteenth aspect, the attaching of the first primer set involves grafting an un-cleavable first primer and a cleavable second primer to the first functionalized layer after its application; and the attaching of the second primer set involves grafting a cleavable first primer and an un-cleavable second primer to the second functionalized layer after its application.

In an example of the fourteenth aspect, the substrate includes a second sacrificial material region in the second portion of each of the trenches; the substrate, the sacrificial material region, and the second sacrificial material region have different etch rates; and prior to applying the first functionalized layer, the method further comprises removing the second sacrificial material region from the second portion of each of the trenches. In one version of this example, wherein prior to removing the second sacrificial material region, the method further comprises forming the sacrificial material region and second sacrificial material region by: applying a sacrificial material on the substrate including the trenches separated by the interstitial regions; removing a portion of the sacrificial material such that a region of the sacrificial material remains directly adjacent to each sidewall of each of the trenches; applying a second sacrificial material on the substrate and on the sacrificial material regions; removing a portion of the second sacrificial material such that a region of the second sacrificial material remains directly adjacent to each of the sacrificial material regions; and applying a material to fill any spaces between the second sacrificial material regions. In one example of this version, the substrate is a multi-layer substrate; the trenches are defined in an outermost layer of the multi-layer substrate; and the material and the outermost layer are the same.

It is to be understood that any features of the fourteenth aspect disclosed herein may be combined together in any desirable manner and/or configuration. Moreover, it is to be understood that any combination of features of the fourteenth aspect and/or of the first aspect and/or of the second aspect may be combined with any of the examples disclosed herein.

A fifteenth aspect disclosed herein is a method comprising applying a sacrificial material to a substrate including depressions separated by first interstitial regions, wherein each depression includes a deep portion and a shallow portion defined by a step portion, and wherein the sacrificial layer partially fills the deep portion; sequentially removing a portion of the sacrificial layer and a portion of the substrate to form second interstitial regions that are at least substantially level with a remaining portion of the sacrificial layer and to remove the step portion to form an area next to the remaining portion of the sacrificial layer; applying a first functionalized layer on the second interstitial regions, the remaining portion of the sacrificial layer, and the area; applying a photoresist on first functionalized layer; removing a portion of the photoresist and an underlying portion of the first functionalized layer so that the remaining portion of the sacrificial layer and the second interstitial regions are exposed, and a portion of the first functionalized layer having a second portion of the photoresist thereon remain at the area; removing the remaining portion of the sacrificial layer to from a second area next to the portion of the first functionalized region; applying a second functionalized layer to the area, thereby forming a second functionalized region; lifting off the second portion of the photoresist, thereby forming a first functionalized region; and attaching a first primer set to the first functionalized layer or the first functionalized region and a second primer set to the second functionalized layer or the second functionalized region, wherein the first primer set is different from the second primer set.

In an example of the fifteenth aspect, the second functionalized layer is also applied to the second portion of the photoresist and the second interstitial regions; a first portion of the second functionalized layer is removed with the second portion of the photoresist; and the method further comprising polishing the second functionalized layer from the second interstitial regions.

In an example of the fifteenth aspect, the attaching of the first primer set involves pre-grafting an un-cleavable first primer and a cleavable second primer to the first functionalized layer before the first functionalized layer is applied; and the attaching of the second primer set involves pre-grafting a cleavable first primer and an un-cleavable second primer to the second functionalized layer before the second functionalized layer is applied.

In an example of the fifteenth aspect, the attaching of the first primer set involves grafting an un-cleavable first primer and a cleavable second primer to the first functionalized layer after its application; and the attaching of the second primer set involves grafting a cleavable first primer and an un-cleavable second primer to the second functionalized layer after its application.

It is to be understood that any features of the fifteenth aspect disclosed herein may be combined together in any desirable manner and/or configuration. Moreover, it is to be understood that any combination of features of the fifteenth aspect and/or of the first aspect and/or of the second aspect may be combined with any of the examples disclosed herein.

A sixteenth aspect disclosed herein is a method comprising imprinting a multi-layer substrate including: a support; a first functionalized layer on the support; a second functionalized layer on the first functionalized layer; and a passivation layer on the second functionalized layer; thereby forming features separated by interstitial regions of the passivation layer, wherein a region of each the first and second functionalized layers is exposed at each feature; attaching a first primer set to the first functionalized layer or the first functionalized region and a second primer set to the second functionalized layer or the second functionalized region, wherein the first primer set is different from the second primer set.

In an example of the sixteenth aspect, the attaching of the first primer set involves pre-grafting an un-cleavable first primer and a cleavable second primer to the first functionalized layer before the first functionalized layer is incorporated into the multi-layer substrate; and the attaching of the second primer set involves pre-grafting a cleavable first primer and an un-cleavable second primer to the second functionalized layer before the second functionalized layer is incorporated into the multi-layer substrate In an example of the sixteenth aspect, the attaching of the first primer set involves grafting an un-cleavable first primer and a cleavable second primer to the first functionalized region in each depression; and the attaching of the second primer set involves grafting a cleavable first primer and an un-cleavable second primer to the second functionalized region in each depression.

It is to be understood that any features of the sixteenth aspect disclosed herein may be combined together in any desirable manner and/or configuration. Moreover, it is to be understood that any combination of features of the sixteenth aspect and/or of the first aspect and/or of the second aspect may be combined with any of the examples disclosed herein.

A seventeenth aspect disclosed herein is a method comprising imprinting a first resin to form a depression including a deep portion and a shallow portion defined by a step portion, wherein the first resin is positioned on a sacrificial layer that is positioned on a second resin; etching a first portion of the first resin and a portion of the sacrificial layer underlying the deep portion, thereby exposing a portion of the second resin; etching the step portion, thereby exposing a second portion of the sacrificial layer; applying a first functionalized layer to the portion of the second resin to form a first functionalized region; removing the second portion of the sacrificial layer, thereby exposing a second portion of the second resin; applying a second functionalized layer to the second portion of the second resin to form a second functionalized region; and attaching a first primer set to the first functionalized layer or the first functionalized region and a second primer set to the second functionalized layer or the second functionalized region, wherein the first primer set is different from the second primer set In an example of the seventeenth aspect, during the applying of the second functionalized layer, the second functionalized layer is deposited on interstitial regions surrounding the depression and is not deposited on the first functionalized region; and the method further comprises polishing the second functionalized layer from the interstitial regions.

It is to be understood that any features of the seventeenth aspect disclosed herein may be combined together in any desirable manner and/or configuration. Moreover, it is to be understood that any combination of features of the seventeenth aspect and/or of the first aspect and/or of the second aspect may be combined with any of the examples disclosed herein.

An eighteenth aspect disclosed herein is a method comprising attaching a first primer set to a first support structure; attaching a second primer set to a second support structure, wherein the second primer set and the second support structure are different than the first primer set and the first support structure; and loading the first and second support structures on a substrate surface having a plurality of first capture sites to selectively attach to the first support structures and a plurality of second capture sites to selective attach to the second support structures.

It is to be understood that any features of the eighteenth aspect disclosed herein may be combined together in any desirable manner and/or configuration. Moreover, it is to be understood that any combination of features of the eighteenth aspect and/or of the first aspect and/or of the second aspect may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 8A through 8F are schematic, cross-sectional view which together depict another example of a method for making another example flow cell including an example of the first region in the depression and the second region on the substrate surface;

FIG. 9 is a schematic, cross-sectional view of an example of the first region in the depression and the second region as part of a bead that is positioned in the depression;

FIG. 10 is a schematic, cross-sectional view of an example of first and second primer sets attached to separate substrates;

FIGS. 11A, 11B, and 11D are schematic perspective views which together depict the formation of another example of a patterned resin on a support;

FIG. 18 is a cross-sectional view taken along line 8-8 of FIG. 17D;

FIGS. 19A through 19D are schematic perspective views which together depict another example of the method disclosed herein using the patterned substrate of FIG. 11D;

FIGS. 22A through 22E are schematic perspective views which together depict an example of the other method disclosed herein;

FIG. 22F is an enlarged view of a depression of an example of a flow cell shown in 22E, wherein the depression includes a block copolymer and a primer grafted to one block;

FIGS. 26A through 26H are schematic views which together illustrate an example method for forming the example regions shown in FIG. 2;

FIGS. 27A through 27F are schematic views which together illustrate another example method for forming the example regions shown in FIG. 2;

FIGS. 28A through 28G are schematic views which together illustrate an example method for forming the example regions shown in FIGS. 3A and 3B;

FIGS. 29A through 29H are schematic views which together illustrate another example method for forming the example regions shown in FIGS. 3A and 3B;

FIGS. 30A through 30F are schematic views which together illustrate still example method for forming the example regions shown in FIGS. 3A and 3B;

FIGS. 31A through 31I are schematic views which together illustrate an example method for forming the example regions shown in FIGS. 3A and 3B;

FIGS. 32A through 32F are schematic views which together illustrate an example method for forming the example regions shown in FIG. 4C;

FIG. 33A is a schematic view of an example method for forming another example of the regions disclosed herein;

FIG. 33B is a top view of one of the depressions of FIG. 33A, illustrating the regions;

FIGS. 34A through 34S are schematic views which together illustrate an example method for forming the example regions in trenches; and FIG. 35 schematically illustrates an example of functionalized support structures;

FIGS. 36A and 36B are schematic views which together illustrate an example method for forming the example regions using the functionalized support structures of FIG. 35;

FIGS. 37A and 37B are schematic views which together illustrate an example method for forming the example regions using the functionalized support structures of FIG. 35;

FIGS. 41A through 41G are schematic views which together illustrate another example method for forming the example regions shown in FIG. 2; and FIGS. 42A through 42H are schematic views which together illustrate yet another example method for forming the example regions shown in FIG. 2.

DETAILED DESCRIPTION

Figure 1:
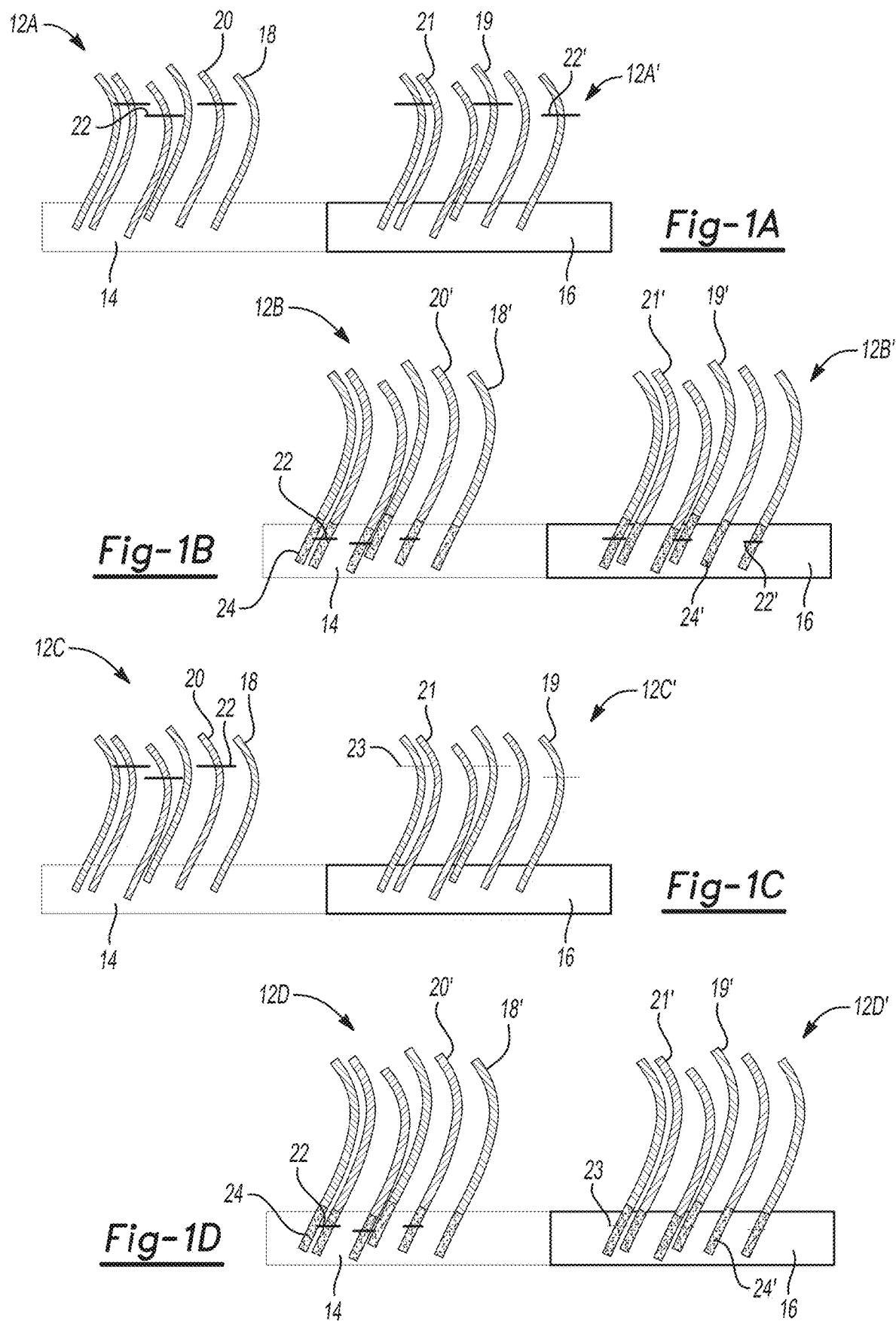
FIGS. 1A through 1D are schematic views of different examples of first and second primer sets attached to first and second region on a substrate.

Examples of the flow cells disclosed herein may be used for nucleic acid sequencing.

Some of the flow cells include different primer sets attached to different regions of the flow cell substrate. In these examples, the primer sets may be controlled so that the cleaving (linearization) chemistry is orthogonal in the different regions. Orthogonal cleaving chemistry may be realized through identical cleavage sites that are attached to different primers in the different sets, or through different cleavage sites that are attached to different primers in the different sets. This enables a cluster of forward strands to be generated in one region of the substrate and a cluster of reverse strands to be generated in another region of the substrate. In an example, the regions are directly adjacent to one another. In another example, any space between the regions is small enough that clustering can span the two regions. With some of the flow cell configurations disclosed herein, the forward and reverse strands are spatially separate, which separates the fluorescence signals from both reads while allowing for simultaneous base calling of each read. As such, some examples of the flow cells disclosed herein enable simultaneous paired-end reads to be obtained.

Other examples of the flow cells may be used to obtain simultaneous paired-end reads; or may be used to obtain sequential paired-end reads, where the forward strands are sequenced and removed, and then the reverse strands are sequenced and removed. In these other examples, a patterned resin on a flow cell support is coated with a block copolymer that undergoes directed self-assembly in depressions of the patterned resin. The patterned resin serves as a guide for the arrangement of the block copolymer. Under controlled conditions, the block copolymer self-assembles into specific domains. In some of the examples disclosed herein, the functionality of the domains is controlled to be orthogonal so that one or more domains can react with the patterned resin and one or more other domains can graft primer(s). In some examples, the functionality of a domain may be controlled to alter a characteristic of that domain. These example flow cells may be suitable for use with optical or non-optical detection methods.

Definitions

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

An "acrylamide monomer" is a monomer with the structure

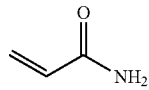

or a monomer including an acrylamide group with that structure. Examples of the monomer including an acrylamide group include azido acetamido pentyl acrylamide:

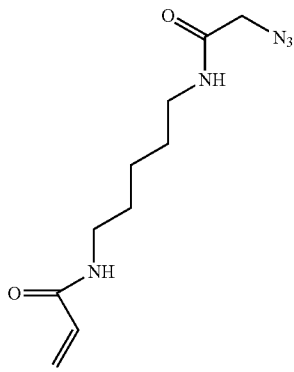 [SMILES: C=CC(=O)NCCCCCNC(=O)CN=[N+]=[N-]]

and N-isopropylacrylamide:

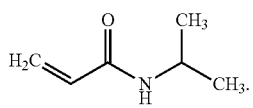

Other acrylamide monomers may be used.

An aldehyde, as used herein, is an organic compound containing a functional group with the structure —CHO, which includes a carbonyl center (i.e., a carbon double-bonded to oxygen) with the carbon atom also bonded to hydrogen and an R group, such as an alkyl or other side chain. The general structure of an aldehyde is:

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

An "amino" functional group refers to an —NR$_a$R$_b$ group, where R$_a$ and R$_b$ are each independently selected from hydrogen (e.g., 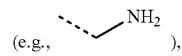 ), C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, the term "attached" refers to the state of two things being joined, fastened, adhered, connected or bound to each other, either directly or indirectly. For example, a bead that is attached to a depression may be physically entrapped in the depression. For another example, a nucleic acid can be attached to a functionalized polymer by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions. For still another example, a primer can be attached to a region on the substrate through a support structure.

An "azide" or "azido" functional group refers to —N$_3$.

The terms "bead" or "core structure" of a functionalized bead refers to a small body made of a rigid or semi-rigid material. The body can have a shape characterized, for example, as a sphere, oval, microsphere, or other recognized particle shape whether having regular or irregular dimensions. Example materials that are useful for beads/core structures include, without limitation, glass; plastic such as acrylic, polystyrene or a copolymer of styrene and another material, polypropylene, polyethylene, polybutylene, polyurethane or polytetrafluoroethylene (TEFLON®, from Chemours); polysaccharides or cross-linked polysaccharides such as agarose or Sepharose; nylon; nitrocellulose; resin; silica or silica-based materials including silicon and modified silicon; carbon-fiber, metal; inorganic glass; optical fiber bundle, or a variety of other polymers. Example beads/core structures include controlled pore glass beads, paramagnetic beads, thoria sol, Sepharose beads, nanocrystals and others known in the art as described, for example, in Microsphere Detection Guide from Bangs Laboratories, Fishers Ind. Beads may also be coated with a polymer that has a functional group that can attach to a primer.

A "block copolymer" is a copolymer formed when two or more monomers cluster together and form blocks of repeating units. Each block should have at least one feature and/or at least one block-specific functional group which is/are not present in adjacent blocks. In the examples disclosed herein, the block copolymers are capable, when exposed to particular annealing conditions, to self-assemble into ordered domains at nanometer-scale dimensions by microphase separation of the constituent polymer blocks. Specific examples of block copolymers will be described further below.

A "block-specific functional group" refers to a moiety of atoms and/or bonds within a particular block of the block polymer that has a particular functionality, such as reacting with a patterned resin, attaching a primer, adjusting an interaction parameter to drive microphase separation, altering a characteristic of the block copolymer, etc. In some examples disclosed herein, each block includes a different block-specific functional group. Specific examples of each block-specific functional group will be described further below.

As used herein, a "bonding region" refers to an area on a support that is to be bonded to another material, which may be, as examples, a spacer layer, a lid, another substrate, etc., or combinations thereof (e.g., a spacer layer and a lid). The bond that is formed at the bonding region may be a chemical bond (as described above), or a mechanical bond (e.g., using a fastener, etc.).

A "capture site", as used herein, refers to portion of a flow cell surface having been physically modified and/or modified with a chemical property that allows for localization of a functionalized support structure. In an example, the capture site may include a chemical capture agent As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms. Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" as used herein refers to —COOH.

A "chemical capture agent" is a material, molecule or moiety that is capable of attaching, retaining, or binding to a target molecule (e.g., a functionalized support structure). One example chemical capture agent includes a capture nucleic acid (e.g., a capture oligonucleotide) that is complementary to at least a portion of a target nucleic acid of or attached to the target molecule. Still another example chemical capture agent includes a member of a receptor-ligand binding pair (e.g., avidin, streptavidin, biotin, lectin, carbohydrate, nucleic acid binding protein, epitope, antibody, etc.) that is capable of binding to the target molecule (or to a linking moiety attached to the target molecule). Yet another example of the chemical capture agent is a chemical reagent capable of forming an electrostatic interaction, a hydrogen bond, or a covalent bond (e.g., thiol-disulfide exchange, click chemistry, Diels-Alder, etc.) with the target molecule.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

The term "depositing," as used herein, refers to any suitable application technique, which may be manual or automated, and, in some instances, results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, screen printing, microcontact printing, inkjet printing, or the like.

As used herein, the term "depression" refers to a discrete concave feature in a substrate or a patterned resin having a surface opening that is at least partially surrounded by interstitial region(s) of the substrate or the patterned resin. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As examples, the depression can be a well or two interconnected wells. The depression may also have more complex architectures, such as ridges, step features, etc.

The term "each," when used in reference to a collection of items, is intended to identify an individual item in the collection, but does not necessarily refer to every item in the collection. Exceptions can occur if explicit disclosure or context clearly dictates otherwise.

The term "epoxy" (also referred to as a glycidyl or oxirane group) as used herein refers to

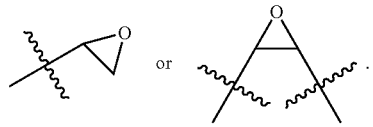

As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber/flow channel can include one or more transparent surfaces allowing for the optical detection of arrays, optically labeled molecules, or the like, at the depression.

As used herein, a "flow channel" may be an area defined between two bonded components, which can selectively receive a liquid sample. In some examples, the flow channel may be defined between a patterned resin and a lid, and thus may be in fluid communication with one or more depressions defined in the patterned resin.

A "functionalized support structure" refers to a small body made of a rigid or semi-rigid material that has one of the primer sets disclosed herein attached to its surface. The body can have a shape characterized, for example, as a sphere, oval, microsphere, or other recognized particle shape whether having regular or irregular dimensions. Example materials that are useful for the body include, without limitation, glass; plastic such as acrylic, polystyrene or a copolymer of styrene and another material, polypropylene, polyethylene, polybutylene, polyurethane or polytetrafluoroethylene (TEFLON®, from Chemours); polysaccharides or cross-linked polysaccharides such as agarose or Sepharose; nylon; nitrocellulose; resin; silica or silica-based materials including silicon and modified silicon; carbon-fiber, metal; inorganic glass; optical fiber bundle, or a variety of other polymers.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a

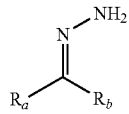

group in which $R_a$ and $R_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, "hydroxy" or "hydroxyl" refers to an —OH group.

As used herein, the term "interstitial region" refers to an area, e.g., of a substrate, patterned resin, or other support that separates depressions. For example, an interstitial region can separate one depression of an array from another depression of the array. The two depressions that are separated from each other can be discrete, i.e., lacking physical contact with each other. In many examples, the interstitial region is continuous whereas the depressions are discrete, for example, as is the case for a plurality of depressions defined in an otherwise continuous surface. In other examples, the interstitial regions and the features are discrete, for example, as is the case for a plurality of trenches separated by respective interstitial regions. The separation provided by an interstitial region can be partial or full separation. Interstitial regions may have a surface material that differs from the surface material of the depressions defined in the surface. For example, depressions can have a polymer and a first primer set therein, and the interstitial regions can have a polymer and a second primer set thereon. For another example, depressions of an array can have beads therein while the interstitial regions do not have beads thereon.

"Nitrile oxide," as used herein, means a "$R_aC\equiv N^+O^-$" group in which $R_a$ is defined herein. Examples of preparing nitrile oxide include in situ generation from aldoximes by treatment with chloramide-T or through action of base on imidoyl chlorides [RC(Cl)=NOH] or from the reaction between hydroxylamine and an aldehyde.

"Nitrone," as used herein, means a

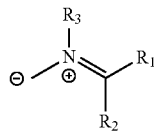

group in which $R_1$, $R_2$, and $R_3$ may be any of the $R_a$ and $R_b$ groups defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acid (PNA).

A "patterned resin" refers to any polymer that can have depressions defined therein. Specific examples of resins and techniques for patterning the resins will be described further below. In some examples disclosed herein, the patterned resin can serve as a guiding template for a block copolymer to self-assemble thereon. Specific examples of characteristics that render a polymer a "guiding template" will be described further below.

As used herein, the "primer" is defined as a single stranded nucleic acid sequence (e.g., single strand DNA or single strand RNA). Some primers, referred to herein as amplification primers, serve as a starting point for template amplification and cluster generation. Other primers, referred to herein as sequencing primers, serve as a starting point for DNA or RNA synthesis. The 5' terminus of the primer may be modified to allow a coupling reaction with a functional group of a polymer or with a bead surface. The primer length can be any number of bases long and can include a variety of non-natural nucleotides. In an example, the sequencing primer is a short strand, ranging from 10 to 60 bases, or from 20 to 40 bases.

A "spacer layer," as used herein refers to a material that bonds two components together. In some examples, the spacer layer can be a radiation-absorbing material that aids in bonding, or can be put into contact with a radiation-absorbing material that aids in bonding.

"Solvent annealing" or "solvent vapor annealing" involves exposing a polymer (e.g., in the form of a film or layer) to an excess of solvent in a sealed enclosure to generate a saturated vapor (i.e., a solvent atmosphere) above the polymer. The polymer film or layer may be held at room temperature (e.g., from about 18° C. to about 25° C.) or at an elevated temperature, which causes the polymer to swell, and increase its chain mobility.

The term "substrate" refers to a structure upon which various components of the flow cell (e.g., a polymer, primer(s), etc.) may be added. The substrate may be a wafer, a panel, a rectangular sheet, a die, or any other suitable configuration. The substrate is generally rigid and is insoluble in an aqueous liquid. The substrate may be inert to a chemistry that is used to modify the depressions or that is present in the depressions. For example, a substrate can be inert to chemistry used to form the polymer, to attach the primer(s), etc. The substrate may be a single layer structure, or a multi-layered structure (e.g., including a support and a patterned resin on the support). Examples of suitable substrates will be described further below.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

Flow Cells for Simultaneous Paired-End Read Sequencing

An example of the flow cell disclosed herein includes a substrate; a first primer set attached to a first region on the substrate, the first primer set including an un-cleavable first primer and a cleavable second primer; and a second primer set attached to a second region on the substrate, the second primer set including a cleavable first primer and an un-cleavable second primer.

Examples of suitable substrates include epoxy siloxane, glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) ($TaO_x$), hafnium oxide ($HaO_2$), carbon, metals, inorganic glasses, or the like. The substrate may also be a multi-layered structure. Some examples of the multi-layered structure include glass or silicon, with a coating layer of tantalum oxide or another ceramic oxide at the surface. Other examples of the multi-layered structure include an underlying support (e.g., glass or silicon) having a patterned resin thereon. Still other examples of the multi-layered substrate may include a silicon-on-insulator (SOI) substrate.

In an example, the substrate may have a diameter ranging from about 2 mm to about 300 mm, or a rectangular sheet or panel having its largest dimension up to about 10 feet (~3 meters). In an example, the substrate is a wafer having a diameter ranging from about 200 mm to about 300 mm. In another example, the substrate is a die having a width ranging from about 0.1 mm to about 10 mm. While example dimensions have been provided, it is to be understood that a substrate with any suitable dimensions may be used. For another example, a panel may be used that is a rectangular support, which has a greater surface area than a 300 mm round wafer.

In some examples of the flow cell, a first primer set is attached to a first region on the substrate and a second primer set is attached to a second region on the substrate. FIG. 1A through FIG. 1D depict different configurations of the primer sets 12A, 12A', 12B, 12B', 12C, 12C', and 12D, 12D' attached to the different regions 14, 16.

Each of the first primer sets 12A, 12B, 12C, and 12D includes an un-cleavable first primer 18 or 18' and a cleavable second primer 20 or 20'; and each of the second primer sets 12A', 12B', 12C', and 12D' includes a cleavable first primer 19 and an un-cleavable second primer 21.

The un-cleavable first primer 18 or 18' and the cleavable second primer 20 or 20' are oligo pairs, e.g., where the un-cleavable first primer 18 or 18' is a forward amplification primer and the cleavable second primer 20 or 20' is a reverse amplification primer or where the cleavable second primer 20 or 20' is the forward amplification primer and the un-cleavable first primer 18 or 18' is the reverse amplification primer. In each example of the first primer set 12A, 12B, 12C, and 12D, the cleavable second primer 20 or 20' includes a cleavage site 22, while the un-cleavable first primer 18 or 18' does not include a cleavage site 22.

The cleavable first primer 19 or 19' and the un-cleavable second primer 21 or 21' are also oligo pairs, e.g., where the cleavable first primer 19 or 19' is a forward amplification primer and un-cleavable second primer 21 or 21' is a reverse amplification primer or where the un-cleavable second primer 21 or 21' is the forward amplification primer and the cleavable first primer 19 or 19' is the reverse amplification primer. In each example of the second primer set 12A', 12B', 12C', and 12D', the cleavable first primer 19 or 19' includes a cleavage site 22' or 23, while the un-cleavable second primer 21 or 21' does not include a cleavage site 22' or 23.

It is to be understood that the un-cleavable first primer 18 or 18' of the first primer set 12A, 12B, 12C, 12D and the cleavable first primer 19 or 19' of the second primer set 12A', 12B', 12C', and 12D' have the same nucleotide sequence (e.g., both are forward amplification primers), except that the cleavable first primer 19 or 19' includes the cleavage site 22' or 23 integrated into the nucleotide sequence or into a linker 24' attached to the nucleotide sequence. Similarly, the cleavable second primer 20 or 20' of the first primer set 12A, 12B, 12C, 12D and the un-cleavable second primer 21 or 21' of the second primer set 12A', 12B', 12C', and 12D' have the same nucleotide sequence (e.g., both are reverse amplification primers), except that the cleavable second primer 20 or 20' includes the cleavage site 22 integrated into the nucleotide sequence or into a linker 24 attached to the nucleotide sequence.

It is to be understood that when the first primers 18 and 19 or 18' and 19' are forward amplification primers, the second primers 20 and 21 or 20' and 21' are reverse primers, and vice versa.

Examples of un-cleavable primers 18, 21 or 18', 21' include P5 and P7 primers, examples of which are used on the surface of commercial flow cells sold by Illumina Inc. for sequencing, for example, on HISEQ™, HISEQX™, MISEQ™, MISEQDX™, MINISEQ™, NEXTSEQ™, NEXTSEQDX™, NOVASEQ™, ISEQ™, GENOME ANALYZER™, and other instrument platforms. The P5 and P7 primers have a universal sequence for capture and/or amplification purposes. In an example, the P5 and P7 primers include the following:

```
P5: 5'→3'
                                            (SEQ. ID. NO. 1)
AATGATACGGCGACCACCGA

P7: 5'→3'
                                            (SEQ. ID. NO. 2)
CAAGCAGAAGACGGCATACGA
```

The P5 and P7 primers are un-cleavable primers 18, 21 or 18', 21' because they do not include a cleavage site 22, 22', 23. It is to be understood that any suitable universal sequence can be used as the un-cleavable primers 18, 21 or 18', 21'.

Examples of cleavable primers 19, 20 or 19', 20' include the P5 and P7 (or other universal sequence) primers with the respective cleavage sites 22, 22', 23 incorporated into the respective nucleic acid sequences (e.g., FIG. 1A and FIG. 1C), or into a linker 24', 24 that attaches the cleavable primers 19, 20 or 19', 20' to the respective regions 16, 14 (FIG. 1B and FIG. 1D). Examples of suitable cleavage sites 22, 22', 23 include enzymatically cleavable nucleobases or chemically cleavable nucleobases, modified nucleobases, or linkers (e.g., between nucleobases). The enzymatically cleavable nucleobase may be susceptible to cleavage by reaction with a glycosylase and an endonuclease, or with an exonuclease. One specific example of the cleavable nucleobase is deoxyuracil (dU), which can be targeted by the USER enzyme. In an example, the uracil base may be incorporated at the $7^{th}$ base position from the 3' end of the P5 primer (P5U) or of the P7 primer (P7U). Other abasic sites may also be used. Examples of the chemically cleavable nucleobases, modified nucleobases, or linkers include a vicinal diol, a disulfide, a silane, an azobenzene, a photocleavable group, allyl T (a thymine nucleotide analog having an allyl functionality), allyl ethers, or an azido functional ether.

Each primer set 12A and 12A' or 12B and 12B' or 12C and 12C' or 12D and 12D' is attached to a respective region 14 or 16 on the substrate. In some examples, the regions 14, 16 have the same surface chemistry, and any of the techniques set forth herein may be used to graft one set of primers 18, 20 or 18', 20' on the region 14, and another set of primers 19, 21 or 19', 21' on the region 16. In other examples, the regions 14 or 16 include different surface chemistries (e.g., functional groups) that can selectively react with the respective primers 18, 20 or 18', 20' or 19, 21 or 19', 21'. In these other examples, the first region 14 has a first functional group, and the second region 16 has a second functional group that is different than the first functional group.

As mentioned, FIG. 1A through FIG. 1D depict different configurations of the primer sets 12A, 12A', 12B, 12B', 12C, 12C', and 12D, 12D' attached to the different regions 14, 16. More specifically, FIG. 1A through FIG. 1D depict different configurations of the primers 18, 20 and 19, 21 or 18', 20' and 19', 21' that may be used.

In the example shown in FIG. 1A, the primers 18, 20 and 19, 21 of the primer sets 12A and 12A' are directly attached to the regions 14 and 16, for example, without a linker 24, 24'. The region 14 may have surface functional groups that can immobilize the terminal groups at the 5' end of the primers 18, 20. Similarly, the region 16 may have surface functional groups that can immobilize the terminal groups at the 5' end of the primers 19, 21. In one example, the immobilization chemistry between the region 14 and the primers 18, 20 and the immobilization chemistry between the region 16 and the primers 19, 21 may be different so that the primers 18, 20 or 19, 21 selectively attach to the desirable region 14 or 16. In another example, the immobilization chemistry may be the same for the regions 14, 16 and the respective primers 18, 20 or 19, 21, and a patterning technique may be used to graft one primer set 12A, 12A' at a time. In still another example, the materials applied to form the regions 14, 16 may have the respective primers 18, 20 or 19, 21 pre-grafted thereto, and thus the immobilization chemistries may be the same or different.

In this example, immobilization may be by single point covalent attachment to the respective region 14 or 16 at the 5' end of the respective primers 18 and 20 or 19 and 21. Any suitable covalent attachment means known in the art may be used at the regions 14, 16. Examples of terminated primers that may be used include an alkyne terminated primer, a tetrazine terminated primer, an azido terminated primer, an amino terminated primer, an epoxy or glycidyl terminated primer, a thiophosphate terminated primer, a thiol terminated primer, an aldehyde terminated primer, a hydrazine terminated primer, a phosphoramidite terminated primer, and a triazolinedione terminated primer. In some specific examples, a succinimidyl (NHS) ester terminated primer may be reacted with an amine at a surface of the region 14 and/or 16, an aldehyde terminated primer may be reacted with a hydrazine at a surface of the region 14 and/or 16, or an alkyne terminated primer may be reacted with an azide at a surface of the region 14 and/or 16, or an azide terminated primer may be reacted with an alkyne or DBCO (dibenzocyclooctyne) at a surface of the region 14 and/or 16, or an amino terminated primer may be reacted with an activated carboxylate group or NHS ester at a surface of the region 14 and/or 16, or a thiol terminated primer may be reacted with an alkylating reactant (e.g., iodoacetamine or maleimide) at a surface of the region 14 and/or 16, a phosphoramidite terminated primer may be reacted with a thioether at a surface of the region 14 and/or 16, or a biotin-modified primer may be reacted with streptavidin at a surface of the region 14 and/or 16.

Also in the example shown in FIG. 1A, the cleavage site 22, 22' of each of the cleavable primers 20, 19 is incorporated into the sequence of the primer 20, 19. In this example, the same type of cleavage site 22, 22' is used in the cleavable primers 20, 19 of the respective primer sets 12A, 12A'. As an example, the cleavage sites 22, 22' are uracil bases, and the cleavable primers 20, 19 are P5U and P7U. In this example, the un-cleavable primer 18 of the oligo pair 18, 20 may be P7, and the un-cleavable primer 21 of the oligo pair 19, 21 may be P5. Thus, in this example, the first primer set 12A includes P7, P5U and the second primer set 12A' includes P5, P7U. The primer sets 12A, 12A' have opposite linearization chemistries, which, after amplification, cluster generation, and linearization, enables forward template strands to be formed on one region 14 or 16 and reverse strands to be formed on the other region 16 or 14.

In the example shown in FIG. 1B, the primers 18', 20' and 19', 21' of the primer sets 12B and 12B' are attached to the regions 14 and 16, for example, through linkers 24, 24'. The region 14 may have surface functional groups that can immobilize the linker 24 at the 5' end of the primers 18', 20'. Similarly, the region 16 may have surface functional groups that can immobilize the linker 24' at the 5' end of the primers 19', 21'. In one example, the immobilization chemistry for the region 14 and the linkers 24 and the immobilization chemistry for the region 16 and the linkers 24' may be different so that the primers 18', 20' or 19', 21' selectively graft to the desirable region 14 or 16. In another example, the immobilization chemistry may be the same for the regions 14, 16 and the linkers 24, 24', and any suitable technique disclosed herein may be used to graft one primer set 12B, 12B' at a time. In still another example, the materials applied to form the regions 14, 16 may have the respective primers 18', 20' and 19', 21' pre-grafted thereto, and thus the immobilization chemistries may be the same or different. Examples of suitable linkers 24, 24' may include nucleic acid linkers (e.g., 10 nucleotides or less) or non-nucleic acid linkers, such as a polyethylene glycol chain, an alkyl group or a carbon chain, an aliphatic linker with vicinal diols, a peptide linker, etc. An example of a nucleic acid linker is a polyT spacer, although other nucleotides can also be used. In one example, the spacer is a 6T to 10T spacer.

The following are some examples of nucleotides including non-nucleic acid linkers (where B is the nucleobase and "oligo" is the primer):

The example shown in FIG. 1D is similar to the example shown in FIG. 1B, except that different types of cleavage sites 22, 23 are used in the linkers 24, 24' attached to the

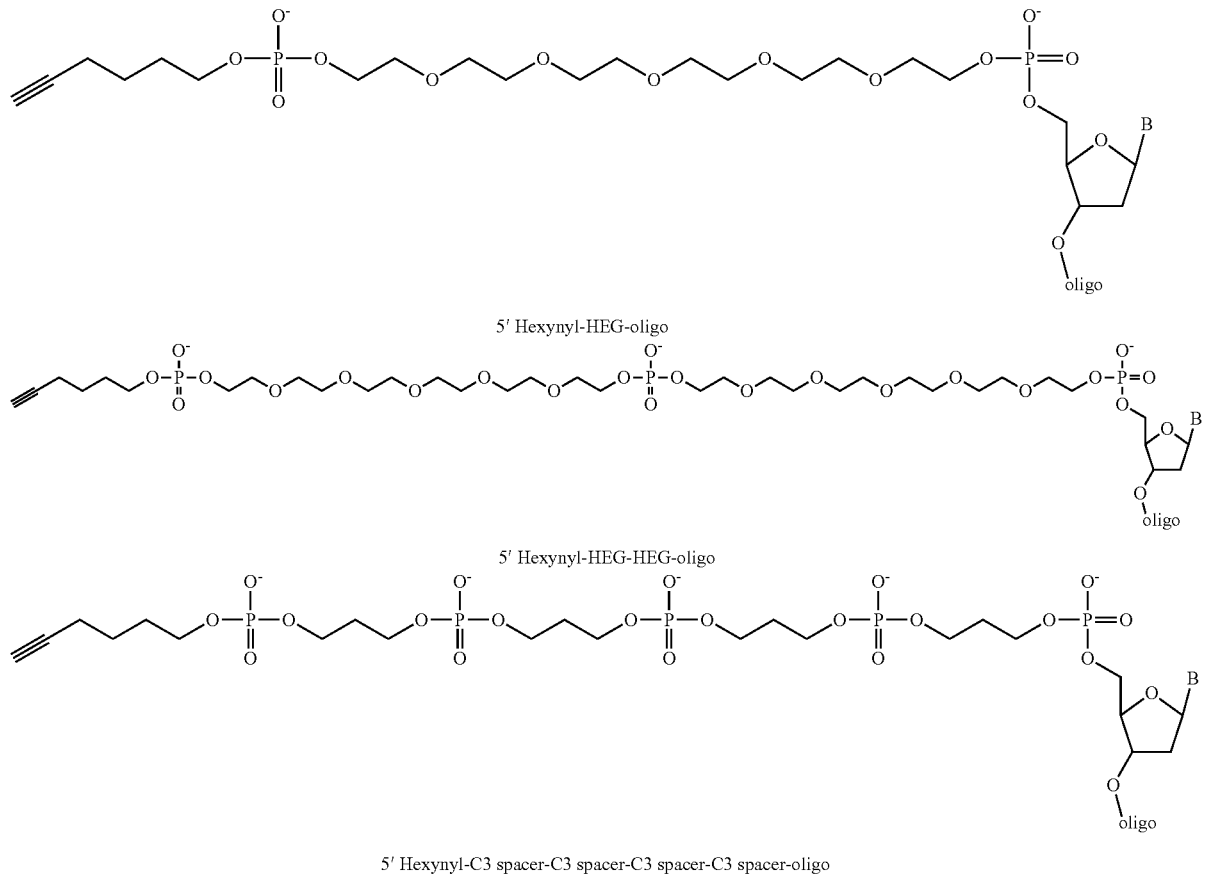

5' Hexynyl-HEG-oligo

5' Hexynyl-HEG-HEG-oligo

5' Hexynyl-C3 spacer-C3 spacer-C3 spacer-C3 spacer-oligo

In the example shown in FIG. 1B, the primers 18', 19' have the same sequence and the same or different linker 24, 24'. The primer 18' in un-cleavable, whereas the primer 19' includes the cleavage site 22' incorporated into the linker 24'. Also in this example, the primers 20', 21' have the same sequence (e.g., P7) and the same or different linker 24, 24'. The primer 21' in un-cleavable, and the primer 20' includes the cleavage site 22 incorporated into the linker 24. The same type of cleavage site 22, 22' is used in the linker 24, 24' of each of the cleavable primers 20', 19'. As an example, the cleavage sites 22, 22' may be uracil bases that are incorporated into nucleic acid linkers 24, 24'. The primer sets 12B, 12B' have opposite linearization chemistries, which, after amplification, cluster generation, and linearization, enables forward template strands to be formed on one region 14 or 16 and reverse strands to be formed on the other region 16 or 14.

The example shown in FIG. 1C is similar to the example shown in FIG. 1A, except that different types of cleavage sites 22, 23 are used in the cleavable primers 20, 19 of the respective primer sets 12C, 12C'. As examples, two different enzymatic cleavage sites may be used, two different chemical cleavage sites may be used, or one enzymatic cleavage site and one chemical cleavage site may be used. Examples of different cleavage sites 22, 23 that may be used in the respective cleavable primers 20, 19 include any combination of a vicinal diol, a uracil, an allyl ether, a disulfide, a restriction enzyme site, and 8-oxoguanine.

cleavable primers 20', 19' of the respective primer sets 12D, 12D'. Examples of different cleavage sites 22, 23 that may be used in the respective in the linkers 24, 24' attached to the cleavable primers 20, 19 include any combination of a vicinal diol, a uracil, an allyl ether, a disulfide, a restriction enzyme site, and 8-oxoguanine.

In any of the examples shown in FIG. 1A through FIG. 1D, the attachment of the primers 18, 20 and 19, 21 or 18', 20' and 19', 21' to the regions 14, 16 leaves a template-specific portion of the primers 18, 20 and 19, 21 or 18', 20' and 19', 21' free to anneal to its cognate template and the 3' hydroxyl group free for primer extension.

The regions 14, 16 represent different areas on the substrate that have different primer sets 12A, 12A', or 12B, 12B', or 12C, 12C', or 12D, 12D' attached thereto. The regions 14, 16 may include materials with different functional groups. In some instances the different functional groups are surface functional groups of the substrate or functional groups that have been introduced to a surface of the substrate, or may be functional groups of another component (e.g., a polymer layer, a bead, etc.) that is deposited on the substrate.

In some examples, the regions 14, 16 are chemically the same, and any technique disclosed herein may be used to sequentially attach the primers 18, 20 and 19, 21 or 18', 20' and 19', 21' of the respective sets 12A and 12A', or 12B and 128', or 12C and 12C', or 12D and 12D' to the respective regions 14, 16.

In one example where the regions 14, 16 are chemically the same, the both regions 14, 16 include the same polymer layer. The polymer layer may be a semi-rigid polymeric material that is permeable to liquids and gases. An example of the polymer layer includes an acrylamide copolymer, such as poly(N-(5-azidoacetamidylpentyl)acrylamide-co-acrylamide, PAZAM. PAZAM and some other forms of the acrylamide copolymer are represented by the following structure (I):

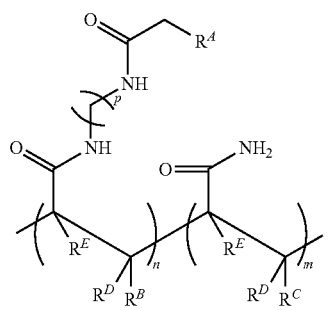

wherein:

$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;

$R^B$ is H or optionally substituted alkyl;

$R^C$, $R^D$, and $R^E$ are each independently selected from the group consisting of H and optionally substituted alkyl;

each of the $-(CH_2)_p-$ can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of the PAZAM may range from about 10 kDa to about 1500 kDa, or may be, in a specific example, about 312 kDa.

In some examples, PAZAM is a linear polymer. In some other examples, PAZAM is a lightly cross-linked polymer.

In other examples, the polymer 26 may be a variation of the structure (I). In one example, the acrylamide unit may be replaced with N,N-dimethylacrylamide

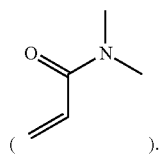

In this example, the acrylamide unit in structure (I) may be replaced with

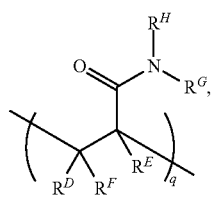

where $R^D$, $R^E$, and $R^F$ are each H, and $R^G$ and $R^H$ are each a methyl group (instead of H as is the case with the acrylamide). In this example, q may be an integer in the range of 1 to 100,000. In another example, the N,N-dimethylacrylamide may be used in addition to the acrylamide unit. In this example, structure (I) may include

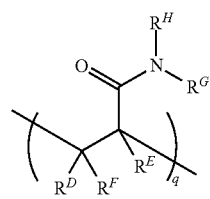

in addition to the recurring "n" and "m" features, where $R^D$, $R^E$, and $R^F$ are each H, and $R^G$ and $R^H$ are each a methyl group. In this example, q may be an integer in the range of 1 to 100,000.

As another example polymer, the recurring "n" feature in structure (I) may be replaced with a monomer including a heterocyclic azido group having structure (II):

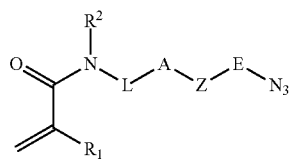

wherein $R^1$ is H or C1-C4 alkyl; $R_2$ is H or C1-C4 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or C1-C4 alkyl attached to the N; and Z is a nitrogen containing heterocycle. Examples of Z include 5 to 10 ring members present as a single cyclic structure or a fused structure.

As still another example, the polymer may include a recurring unit of each of structure (III) and (IV):

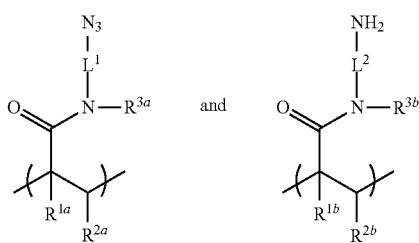

wherein each of $R^{1a}$, $R^{2a}$, $R^{1b}$ and $R^{2b}$ is independently selected from hydrogen, optionally substituted alkyl or optionally substituted phenyl; each $R^{3a}$ and $R^{3b}$ is independently selected from hydrogen, optionally substituted alkyl, optionally substituted phenyl, or optionally substituted C7-C14 aralkyl; and each $L^1$ and $L^2$ is independently selected from an optionally substituted alkylene linker or an optionally substituted heteroalkylene linker.

It is to be understood that other molecules may be used to form the polymer layer, as long as they are functionalized to interact with the first and second primer sets 12A, 12A' or 12B, 12B', or 12C, 12C', or 12D, 12D'. Other examples of suitable polymer layers include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photocycloaddition reactions. Still other examples of suitable polymer layers include mixed copolymers of acrylamides and acrylates. Branched polymers, such as star polymers, star-shaped or star-block polymers, dendrimers, and the like may also be used.

In other examples, the regions 14, 16 are chemically different. For example, the region 14 may have surface functional groups that can immobilize the primers 18, 20 or 18', 20' of the first primer sets 12A, 12B, 12C, 12D, and the region 16 may have different surface functional groups that can immobilize the primers 19, 21 or 19', 21' of the second primer sets 12A', 12B', 12C', 12D'.

In one example where the regions 14, 16 are chemically different, a block copolymer is used. In this example, the block copolymer includes two different blocks, one with primer-grafting functional groups that can attach to the primers 18, 20 or 18', 20' of the first primer sets 12A, 12B, 12C, 12D and another with primer-grafting functional groups that can attach to the primers 19, 21 or 19', 21' of the second primer sets 12A', 12B', 12C', 12D'. Examples of primer-grafting functional group are selected from the group consisting of azide/azido, optionally substituted amino, optionally substituted alkenyl, aldehyde, optionally substituted hydrazone, optionally substituted hydrazine, carboxyl, hydroxy, optionally substituted tetrazole, optionally substituted tetrazine, nitrile oxide, nitrone, thiol, and combinations thereof.

Other examples of chemically different regions 14, 16 include gold and PAZAM, gold and aluminum, silanes having two different surface functional groups (e.g., azides and amines), a thiol self-assembled monolayer on gold and a phosphonate self-assembled monolayer on aluminum or hafnium oxide, $SiO_2$ and $Ta_2O_5$, epoxy and $Ta_2O_5$, a first polymer including azide groups and a second polymer including amine groups, $SiO_2$ and copper, or epoxy and copper. While several examples have been provided, it is to be understood that other combinations of chemically different regions 14, 16 may be used.

The regions 14, 16 may also have different physical configurations. FIG. 2 through FIG. 6B illustrate different examples of these configurations. In these examples, the substrate 26 is shown as a single layer/material, such as glass, silicon, etc. It is to be understood, however, that a multi-layered substrate may be used with any of these example configurations. For example, any of these examples may include a support and a patterned resin formed on the support.

Figure 2:
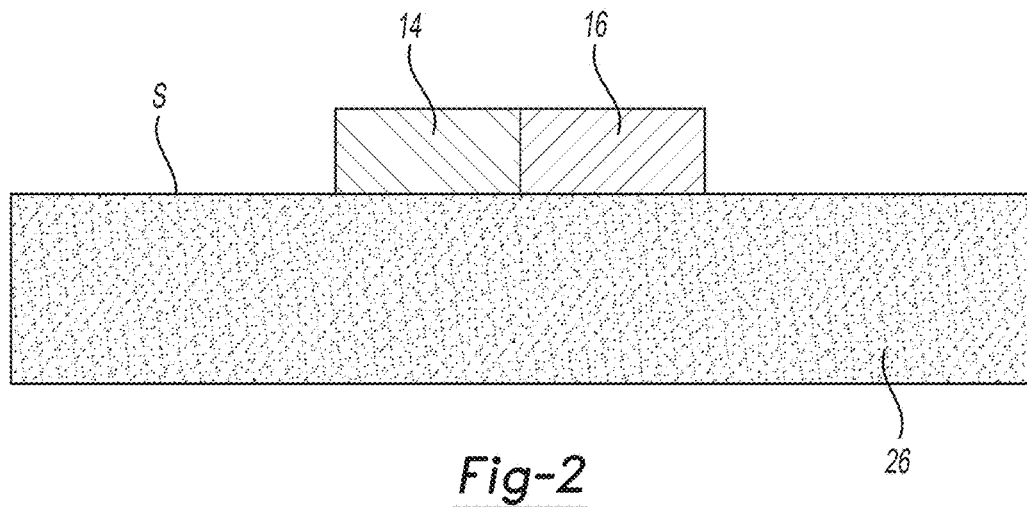
FIG. 2 is a schematic, cross-sectional view of an example of the first and second regions on a substrate surface.

FIG. 2 illustrates an example where the regions 14, 16 are located on different areas of a surface S of the substrate 26.

One example method for making the example shown in FIG. 2 is shown in FIG. 26A through FIG. 26H. While the primer sets 12A, 12A' or 12B, 12B' or 12C, 12C' or 12D, 12D' are mentioned throughout this description, they are not shown for clarity.

As shown at FIG. 26A, a first functionalized layer 60 is applied on a substrate 26. The first functionalized layer 60 may be a polymer (PAZAM), a silane, a metal (gold, aluminum, etc.) or any other material that has a functional group that can attach to the first primer set 12A, 12B, 12C, 12D. The first functionalized layer 60 may be deposited using any of the techniques described herein.

Depending upon the first functionalized layer 60 that is used, the substrate 26 may be activated using silanization or plasma ashing to generate surface groups that can react with the first functionalized layer 60. Examples of silanization and plasma ashing are described in more detail in reference to FIG. 13A. The first functionalized layer 60 may then be deposited using any of the techniques described herein. Depending upon the material used, the first functionalized layer 60 may also be cured.

In FIG. 26B and FIG. 26C, the first functionalized layer 60 is then patterned to form a first functionalized region (region 14) covered by a photoresist 62. In an example, the photoresist 62 is a negative photoresist (exposed region becomes insoluble). An example of suitable negative photoresist includes the epoxy-based SU-8 photoresist (available from MicroChemicals). The photoresist 62 is applied to the first functionalized layer 60, is selectively exposed to certain wavelengths of light to form the insoluble region (shown at 62), and is exposed to a developer solution to remove the soluble portions. In another example, the photoresist 62 is a positive photoresist (exposed region becomes soluble). Examples of suitable positive photoresists include the MICROPOSIT® S1800 series or the AZ® 1500 series, both of which are available from MicroChemicals. The photoresist 62 is applied to the substrate 26, is selectively exposed to certain wavelengths of light to form the soluble region, and is exposed to a developer solution to remove the soluble portions, leaving the insoluble region (shown at 62). In other examples, the photoresist 62 may be replaced with a nanoimprint lithography resin that is patterned to form the region (e.g., 62).

As shown in FIG. 26C, the exposed portions of the first functionalized layer 60 (e.g., those not covered by the photoresist 62) may then be removed, e.g., via etching or another suitable technique.

As shown in FIG. 26D, the second functionalized layer 64 is then applied, using any suitable deposition technique, on the photoresist 62 and on portions (e.g., the exposed surface S) of the substrate 26. Depending upon the material used, the second functionalized layer 64 may also be cured.

As shown in FIG. 26E, the photoresist 62 may then be lifted off, which also removes any of the second functionalized layer 64 thereon.

In FIG. 26F and FIG. 26G, a portion of the second functionalized layer 64 is removed. To remove the portion(s), a second photoresist 62' is applied, exposed, and developed so that the insoluble region (shown at 62') covers the first functionalized region 14 and a desirable portion of the second functionalized layer 64 that is i) adjacent to the first functionalized region 14 and ii) to become the second functionalized region 16. Once the photoresist 62' is formed, the exposed portions of the second functionalized layer 64 (e.g., those not covered by the photoresist 62') may then be removed, e.g., via etching or another suitable technique.

As shown in FIG. 26H, the photoresist 62' may then be lifted off, which exposes the first and second functionalized regions 14, 16.

In some examples, the primers 18, 20 or 18', 20' (not shown in FIG. 26A through FIG. 26H) may be pre-grafted to the first functionalized layer 60, and thus are attached to the first functionalized region 14. Similarly, the primers 19, 21 or 19', 21' (not shown in FIG. 26A through FIG. 26H) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 26A). If the regions 14, 16 have different functional groups, the primers 18, 20 or 18', 20' may be grafted at the end of the method (e.g., at FIG. 26H), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 26D). If the regions 14, 16 have different functional groups, the primers 19, 21 or 19', 21' may be grafted at the end of the method (e.g., at FIG. 26H), because they will not graft to the surface functional groups of the region 14.

When grafting is performed during the method, grafting may be accomplished by flow through deposition (e.g., using a temporarily bound lid), dunk coating, spray coating, puddle dispensing, or by another suitable method that will attach the primer(s) 18, 20 or 18', 20' to the region 14 or that will attach the primer(s) 19, 21 or 19', 21' to the region 16. Each of these example techniques may utilize a primer solution or mixture, which may include the primer(s) 18, 20 or 18', 20', 19, 21 or 19', 21' water, a buffer, and a catalyst. With any of the grafting methods, the primers 18, 20 or 18', 20' react with reactive groups of the region 14 or the primers 19, 21 or 19', 21' react with reactive groups of the region 16, and have no affinity for the substrate 26.

While not shown in FIG. 26A through FIG. 26H, this example method may further include depositing a first self-assembled monolayer (SAM) on the first functionalized region 14 and depositing a second self-assembled monolayer (SAM) on the second functionalized region 16. In an example, the region 14 is gold, and the first SAM includes thiol groups that can attach to the gold and azide groups that can attach to the primers 18, 20 or 18', 20'. In another example, the region 16 is hafnium oxide or aluminum oxide, and the second SAM includes phosphonate groups that can attach to the hafnium oxide or aluminum oxide and amine groups that can attach to the primers 19, 21 or 19', 21'. In the example using the self-assembled monolayers, the primer sets 12A, 12A' or 12B, 12B' or 12C, 12C' or 12D, 12D' are grafted after the SAMS are formed.

Another example method for making the example shown in FIG. 2 is shown in FIG. 27A through FIG. 27F. While the primer sets 12A, 12A' or 12B, 12B' or 12C, 12C' or 12D, 12D' are mentioned throughout this description, they are not shown for clarity.

As shown at FIG. 27A, a first photoresist 62 is applied on the substrate 26 so that a first substrate portion 66 remains exposed. In this example, the photoresist 62 may be a positive photoresist (exposed region becomes soluble) or a negative photoresist (exposed region becomes insoluble). The photoresist 62 may also be replaced with a nanoimprint lithography resin that is patterned to form a region (e.g., 62).

As shown in FIG. 27B, the first functionalized layer 60 may be deposited on the photoresist 62 and on the first substrate portion 66 using any of the techniques described herein. In some instances, the first functionalized layer 60 may also be cured.

As shown in FIG. 27C, the photoresist 62 may then be lifted off, which also removes any of the first functionalized layer 60 thereon. This leaves the region 14 formed on the substrate surface S.

A second photoresist 62' is applied, exposed, and developed so that the insoluble region (shown at 62') covers the first functionalized region 14 and the substrate 26, except at a second substrate portion 68 that is adjacent to the first functionalized region 14.

As shown in FIG. 27E, the second functionalized layer 64 is then applied, using any suitable deposition technique and, in some instances curing, on the photoresist 62' and on the second substrate portion 68.

As shown in FIG. 27F, the photoresist 62' may then be lifted off, which removes any of the second functionalized layer 64 thereon. This exposes the first and second functionalized regions 14, 16.

In some examples, the primers 18, 20 or 18', 20' (not shown in FIG. 27A through FIG. 27F) may be pre-grafted to the first functionalized layer 60, and thus are attached to the first functionalized region 14. Similarly, the primers 19, 21 or 19', 21' (not shown in FIG. 27A through FIG. 27F) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 27B or 27C). If the regions 14, 16 have different functional groups, the primers 18, 20 or 18', 20' may be grafted at the end of the method (e.g., at FIG. 27F), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 27E). If the regions 14, 16 have different functional groups, the primers 19, 21 or 19', 21' may be grafted at the end of the method (e.g., at FIG. 27F), because they will not graft to the surface functional groups of the region 14.

When grafting is performed during the method, grafting may be accomplished using any grafting technique disclosed herein. With any of the grafting methods, the primers 18, 20 or 18', 20' react with reactive groups of the region 14 or the primers 19, 21 or 19', 21' react with reactive groups of the region 16, and have no affinity for the substrate 26.

While not shown in FIG. 27A through FIG. 27F, this example method may further include depositing a first self-assembled monolayer (SAM) on the first functionalized region 14 and depositing a second self-assembled monolayer (SAM) on the second functionalized region 16. In the example using the self-assembled monolayers, the primer sets 12A, 12A' or 12B, 12B' or 12C, 12C' or 12D, 12D' are grafted after the SAMS are formed.

Yet another example method for making the example shown in FIG. 2 is shown in FIG. 41A through FIG. 41G. While the primer sets 12A, 12A' or 12B, 12B' or 12C, 12C' or 12D, 12D' are mentioned throughout this description, they are not shown for clarity.

The substrate 26 may be any examples of the substrate disclosed herein. While not shown, it is to be understood that the substrate may also be a multi-layered substrate including an un-patterned resin on a support (e.g., a nanoimprint lithography resin on a glass support, or any other example of the resin 54 and support 52 described herein, see the section "Bead Based Flow Cell").

As shown in FIG. 41A, in this example, a sacrificial metal layer 98 is applied on the substrate 26. In an example, the nanoimprint lithography resin/resist of the multi-layered substrate may be exposed to oxygen plasma, and then the sacrificial metal layer 98 may be deposited using any suitable metal deposition technique. In an example, the sacrificial metal layer 98 is deposited using sputtering. Examples of the sacrificial metal layer 98 include aluminum or copper, and the layer 98 may have a thickness ranging from about 10 nm to about 100 nm.

As shown in FIG. 41B, a resist is applied to the sacrificial metal layer 98 and is patterned to define a multi-level or multi-depth depression therein. The patterned resin is shown at reference numeral 54'. In this example, the resin may be any nanoimprint lithography resin. In an example, the resin is spin coated and soft baked, and then stamped and cured (e.g., using ultraviolet curing) to define a multi-level or multi-depth depression that includes a deep portion 70 and the shallow portion 72 which is defined, in part, by a step portion 74 of the patterned resin 54'.

Wet or dry etching may then be used to expose a portion 100 of the substrate 26 (e.g., a portion of the un-patterned resin or glass of the multi-layered substrate) underlying the deep portion 70 and a portion 102 of the sacrificial metal layer 98 underlying the shallow portion 72. The exposed portions are shown in FIG. 41C. In an example of wet etching, $FeCl_3$ may be used to remove a copper sacrificial metal layer 98. In another example of wet etching, KOH may be used to remove an aluminum sacrificial metal layer 98. In an example of dry etching, oxygen plasma may first be used to remove residue of the patterned resin 54', and then a combination of $Cl_2$ and $BCl_3$ plasmas may be used to etch an aluminum sacrificial metal layer 98. Oxygen plasma may again be used to clean the exposed portions 100 and 102. In this example, the depths D1 (e.g., of the shallow portion 72) and D2 (e.g., from the bottom of the deep portion 70 to the top of the step portion 74), and the thickness D3 of the sacrificial metal layer 98 may be the same or similar (e.g., within one nm of each other) so that the desired thickness of each of the materials 54' and 98 is removed during etching in order to expose the portions 100 and 102.

As shown in FIG. 41D, the first functionalized layer 60 may be deposited on the remaining patterned resin 54', on the exposed portion 100 of the substrate 26, and on the exposed portion 102 of the sacrificial metal layer 98. The first functionalized layer 60 may be any of the examples and may be deposited using any of the techniques described herein. In some instances, the first functionalized layer 60 is also cured.

In FIG. 41E, wet etching is used to selectively remove a portion of the first functionalized layer 60 and another portion of the sacrificial metal layer 98 in order to expose another portion 104 of the substrate 26. Wet etching may be performed as described herein. The etchant used can etch the sacrificial metal layer 98, thus lifting off the first functional layer 60.

As shown in FIG. 41F, the second functionalized layer 64 is then applied, on the exposed portion 104 and on the first functionalized layer 60. Any suitable deposition technique may be used for the second functionalized layer 64. In any of the example methods disclosed herein, when deposition is performed under high ionic strength (e.g., in the presence of 10×PBS, NaCl, KCl, etc.), the second functionalized layer 64 does not deposit on or adhere to the first functionalized layer 60. As such, the second functionalized layer 64 does not contaminate the first functionalized layer 60, leaving the region 16.

As shown in FIG. 41G, the remaining patterned resin 54 may then be lifted off, which removes any of the first functionalized layer 60 thereon. This lift off process may be performed in dimethylsulfoxide (DMSO) using sonication, or in acetone, or with an NMP (N-methyl-2-pyrrolidone) based stripper. The remaining sacrificial metal layer 98 is then exposed, and can be removed using wet etching as described herein. The regions 14, 16 remain intact on the substrate surface after wet etching, in part because the sacrificial metal layer 98 is not present under the regions 14, 16.

In some examples, the primers 18, 20 or 18', 20' (not shown in FIG. 41A through FIG. 41G) may be pre-grafted to the first functionalized layer 60, and thus are attached to the first functionalized region 14. Similarly, the primers 19, 21 or 19', 21' (not shown in FIG. 41A through FIG. 41G) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 41D). If the regions 14, 16 have different functional groups, the primers 18, 20 or 18', 20' may be grafted at the end of the method (e.g., at FIG. 41G), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 41F). If the regions 14, 16 have different functional groups, the primers 19, 21 or 19', 21' may be grafted at the end of the method (e.g., at FIG. 41G), because they will not graft to the surface functional groups of the region 14.

When grafting is performed during the method, grafting may be accomplished by flow through deposition (e.g., using a temporarily bound lid), dunk coating, spray coating, puddle dispensing, or by another suitable method that will attach the primer(s) 18, 20 or 18', 20' to the region 14 or that will attach the primer(s) 19, 21 or 19', 21' to the region 16. Each of these example techniques may utilize a primer solution or mixture, which may include the primer(s) 18, 20 or 18', 20', 19, 21 or 19', 21' water, a buffer, and a catalyst. With any of the grafting methods, the primers 18, 20 or 18', 20' react with reactive groups of the region 14 or the primers 19, 21 or 19', 21' react with reactive groups of the region 16, and have no affinity for the substrate 26.

Still another example method for making the example shown in FIG. 2 is shown in FIG. 42A through FIG. 42H. Again, while the primer sets 12A, 12A' or 12B, 12B' or 12C, 12C' or 12D, 12D' are mentioned throughout this description, they are not shown for clarity.

The substrate 26 may be any examples of the substrate disclosed herein. Similar to the example described in FIG. 41A through FIG. 41G, the substrate may also be a multi-layered substrate including an un-patterned resin on a support.

As shown in FIG. 42A, in this example, the sacrificial metal layer 98 is applied on the substrate 26. The sacrificial metal layer 98 may be any of the example material and may be deposited by any of the examples described in reference to FIG. 41A.

As shown in FIG. 42B, a resist is applied to the sacrificial metal layer 98 and is patterned to define a multi-level or multi-depth depression therein. The patterned resin is shown at reference numeral 54'. In this example, the resin may be any nanoimprint lithography resin. In an example, the resin is spin coated and soft baked, and then stamped and cured (e.g., using ultraviolet curing) to define multi-level or multi-depth depression that includes a deep portion 70 and the shallow portion 72 which is defined, in part, by a step portion 74 of the patterned resin 54'.

Wet or dry etching may then be used to expose a portion 100 of the substrate 26 (e.g., a portion of the un-patterned resin of the multi-layered substrate) underlying the deep portion 70 and a portion 102 of the sacrificial metal layer 98 underlying the shallow portion 72. The exposed portions 100 and 102 are shown in FIG. 42C. Wet or dry etching may be performed as described in reference to FIG. 41C.

As shown in FIG. 42D, the first functionalized layer 60 may be deposited on the remaining patterned resin 54', on the exposed portion 100 of the substrate 26, and on the exposed portion 102 of the sacrificial metal layer 98. The first functionalized layer 60 may be any of the examples and may be deposited using any of the techniques described herein. In some instances, the first functionalized layer 60 may also be cured.

In FIG. 42E and FIG. 42F, the first functionalized layer 60 is then patterned to form a first functionalized region (region 14) covered by a photoresist 62. In this example, the photoresist 62 is a negative photoresist. The photoresist 62 may be applied to the first functionalized layer 60, selectively exposed to certain wavelengths of light to form an insoluble region, and exposed to a developer solution to remove the soluble portions. The remaining photoresist 62 is positioned on the portion of the first functionalized layer 60 that is on the portion 100 in the deep portion 70.

As shown in FIG. 42F, the exposed portions of the first functionalized layer 60 (e.g., those not covered by the photoresist 62) may then be removed, e.g., via etching or another suitable technique. This etching process (e.g., oxygen plasma) also removes some of the patterned resin 54', and some of the photoresist 62. In a separate etch process, the sacrificial metal layer 98 that had been underlying the shallow portion 72 (see FIG. 42B) is removed. In this example, wet or dry etching as described in reference to FIG. 41C may be used. This process exposes the other portion 104 of the substrate 26.

As shown in FIG. 42G, the second functionalized layer 64 is then applied, using any suitable deposition technique, on the exposed portions of the resin 54', the photoresist 62, and the exposed portion 104 of the substrate 26. In an example, the second functionalized layer 64 may be deposited on the photoresist 62, but may be removed with the photoresist 62 when it is lifted off.

As shown in FIG. 42H, the remaining patterned resin 54' and the photoresist 62 may then be lifted off, which removes any of the second functionalized layer 64 thereon. This lift off process may be performed in dimethylsulfoxide (DMSO) using sonication, or in acetone, or with an NMP (N-methyl-2-pyrrolidone) based stripper. The remaining sacrificial metal layer 98 is then exposed, and can be removed using wet etching as described herein. The regions 14, 16 remain intact on the substrate surface after wet etching, in part because the sacrificial metal layer 98 is not present under the regions 14, 16.

In some examples, the primers 18, 20 or 18', 20' (not shown in FIG. 42A through FIG. 42H) may be pre-grafted to the first functionalized layer 60, and thus are attached to the first functionalized region 14. Similarly, the primers 19, 21 or 19', 21' (not shown in FIG. 42A through FIG. 42H) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 42D). If the regions 14, 16 have different functional groups, the primers 18, 20 or 18', 20' may be grafted at the end of the method (e.g., at FIG. 42H), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 42G). If the regions 14, 16 have different functional groups, the primers 19, 21 or 19', 21' may be grafted at the end of the method (e.g., at FIG. 42H), because they will not graft to the surface functional groups of the region 14.

When grafting is performed during the method, grafting may be accomplished by flow through deposition (e.g., using a temporarily bound lid), dunk coating, spray coating, puddle dispensing, or by another suitable method that will attach the primer(s) 18, 20 or 18', 20' to the region 14 or that will attach the primer(s) 19, 21 or 19', 21' to the region 16. Each of these example techniques may utilize a primer solution or mixture, which may include the primer(s) 18, 20 or 18', 20', 19, 21 or 19', 21' water, a buffer, and a catalyst. With any of the grafting methods, the primers 18, 20 or 18', 20' react with reactive groups of the region 14 or the primers 19, 21 or 19', 21' react with reactive groups of the region 16, and have no affinity for the substrate 26.

The example regions 14, 16 shown in FIG. 2 may also be formed using micro-contact printing or direct printing techniques, such as inkjet printing. These methods may be particularly suitable when it is desirable to generate regions on a micron scale, such as about 1 μm to about 50 μm.

In the example shown in FIG. 2, it is to be understood that multiple sets of isolated regions 14, 16 may be formed in an array across the substrate surface S. Many different layouts may be used for the array, as long as the regions 14, 16 within an isolated set are adjacent to one another.

FIG. 3A through FIG. 6B illustrate different examples where at least one of the regions 14, 16 is located in a depression 28 defined in the substrate 26. The depressions 28 may be formed in a single layered substrate (e.g., substrate 26) or may be formed in an outermost layer of a multi-layered substrate.

Depressions 28 may be formed using any suitable technique, such as photolithography, nanoimprint lithography (NIL), stamping techniques, embossing techniques, molding techniques, microetching techniques, etc.

While a single depression 28 is shown in each of FIG. 3A through FIG. 6B, it is to be understood that a flow cell may include a plurality of depressions 28 that are separated by interstitial regions 30, where each of the depressions 28 includes the first region 14 located at a first portion and the second region 16 located at a second portion. Still further, some of the examples disclosed herein include depressions 28A and 28B with different sizes (see, e.g., FIG. 11C), or depressions 28C that include two portions 34, 34' that are interconnected, but which have different sizes (see, e.g., FIG. 11D). It is to be understood that the following discussion related to the depressions 28 may be applicable for any example of the depressions 28, 28A, 28B, 28C disclosed herein.

Many different layouts of the depressions 28 may be envisaged, including regular, repeating, and non-regular patterns. In an example, the depressions 28 are disposed in a hexagonal grid for close packing and improved density. Other layouts may include, for example, rectilinear (i.e., rectangular) layouts (see FIG. 24), triangular layouts, and so forth. In some examples, the layout or pattern can be an x-y format of depressions 28 that are in rows and columns. In some other examples, the layout or pattern can be a repeating arrangement of depressions 28 and/or interstitial regions 30. In still other examples, the layout or pattern can be a random arrangement of depressions 28 and/or interstitial regions 30. The pattern may include stripes, swirls, lines, triangles, rectangles, circles, arcs, checks, plaids, diagonals, arrows, squares, and/or cross-hatches.

The layout or pattern may be characterized with respect to the density of the depressions 28 (i.e., number of depressions 28) in a defined area. For example, the depressions 28 may be present at a density of approximately 2 million per $mm^2$. The density may be tuned to different densities including, for example, a density of at least about 100 per $mm^2$, at least about 1,000 per $mm^2$, at least about 0.1 million per $mm^2$, at least about 1 million per $mm^2$, at least about 2 million per $mm^2$, at least about 5 million per $mm^2$, at least about 10 million per $mm^2$, at least about 50 million per $mm^2$, or more. Alternatively or additionally, the density may be tuned to be no more than about 50 million per $mm^2$, no more than about 10 million per $mm^2$, no more than about 5 million per $mm^2$, no more than about 2 million per $mm^2$, no more than about 1 million per $mm^2$ no more than about 0.1 million per $mm^2$, no more than about 1,000 per $mm^2$, no more than about 100 per $mm^2$, or less. It is to be further understood that the density of depressions 28 can be between one of the lower values and one of the upper values selected from the ranges above. As examples, a high density array may be characterized as having depressions 28 separated by less than about 100 nm, a medium density array may be characterized as having depressions 28 separated by about 400 nm to about 1 μm (1000 nm), and a low density array may be characterized as having depressions 28 separated by greater than about 1 μm. While example densities have been provided, it is to be understood that substrates with any suitable densities may be used.

The layout or pattern of the depressions 28 may also or alternatively be characterized in terms of the average pitch, i.e., the spacing from the center of the depression 28 to the center of an adjacent depression 28 (center-to-center spacing) or from the edge of one depression 28 to the edge of an adjacent depression 28 (edge-to-edge spacing). The pattern can be regular, such that the coefficient of variation around the average pitch is small, or the pattern can be non-regular in which case the coefficient of variation can be relatively large. In either case, the average pitch can be, for example, at least about 10 nm, about 0.1 μm, about 0.5 μm, about 1 μm, about 5 μm, about 10 μm, about 100 μm, or more. Alternatively or additionally, the average pitch can be, for example, at most about 100 μm, about 10 μm, about 5 μm, about 1 μm, about 0.5 μm, about 0.1 μm, or less. The average pitch for a particular pattern of depressions 28 can be between one of the lower values and one of the upper values selected from the ranges above. In an example, the depressions 28 have a pitch (center-to-center spacing) of about 1.5 μm. While example average pitch values have been provided, it is to be understood that other average pitch values may be used.

Figure 3A:
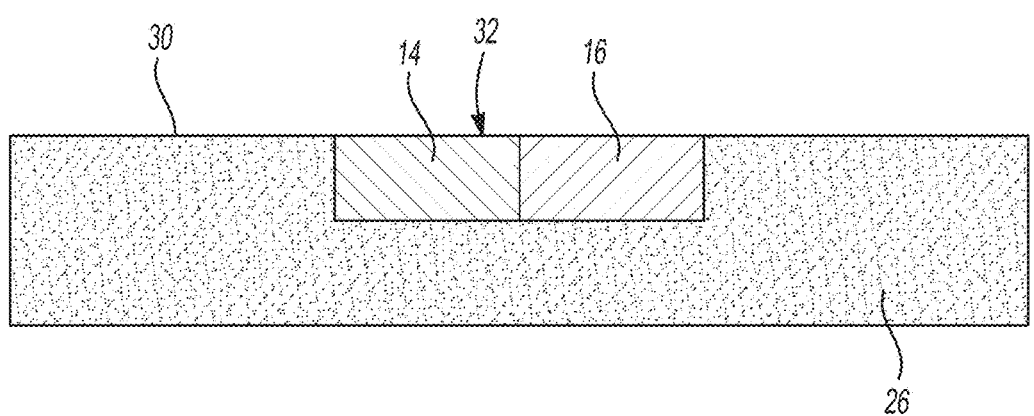
FIGS. 3A and 3B are, respectively, a schematic, cross-sectional view and a top view of an example of the first and second regions in a depression.

In the example shown in FIG. 3A through FIG. 68, the depressions 28 are wells. The wells may be micro wells or nanowells. The size of each well may be characterized by its volume, well opening area, depth, and/or diameter.

Each well can have any volume that is capable of confining a liquid. The minimum or maximum volume can be selected, for example, to accommodate the throughput (e.g., multiplexity), resolution, analyte composition, or analyte reactivity expected for downstream uses of the flow cell. For example, the volume can be at least about $1 \times 10\text{-}3$ $\mu m^3$, at least about $1 \times 10^{-2}$ $\mu m^3$, at least about 0.1 $\mu m^3$, at least about 1 $\mu m^3$, at least about 10 $\mu m^3$, at least about 100 $\mu m^3$, or more. Alternatively or additionally, the volume can be at most about $1 \times 10^4$ $\mu m^3$, at most about $1 \times 10^3$ $\mu m^3$, at most about 100 $\mu m^3$, at most about 10 $\mu m^3$, at most about 1 $\mu m^3$, at most about 0.1 $\mu m^3$, or less. It is to be understood that the region(s) 14, 16 can fill all or part of the volume of a well. The volume of, for example, the polymer layer in an individual well can be greater than, less than or between the values specified above.

The area occupied by each well opening on a surface can be selected based upon similar criteria as those set forth above for well volume. For example, the area for each well opening on a surface can be at least about $1 \times 10^{-3}$ $\mu m^2$, at least about $1 \times 10^{-2}$ $\mu m^2$, at least about 0.1 $\mu m^2$, at least about 1 $\mu m^2$, at least about 10 $\mu m^2$, at least about 100 $\mu m^2$, or more. Alternatively or additionally, the area can be at most about $1 \times 10^3$ $\mu m^2$, at most about 100 $\mu m^2$, at most about 10 $\mu m^2$, at most about 1 $\mu m^2$, at most about 0.1 $\mu m^2$, about $1 \times 10^{-2}$ $\mu m^2$, or less. The area occupied by each well opening can be greater than, less than or between the values specified above.

The depth of each well (or any other type of depression 28) can be at least about 0.1 μm, at least about 1 μm, at least about 10 μm, at least about 100 μm, or more. Alternatively or additionally, the depth can be at most about $1 \times 10^3$ μm, at most about 100 μm, at most about 10 μm, at most about 1 μm, at most about 0.1 μm, or less. The depth of each well (or other depression 28) can be greater than, less than or between the values specified above.

In some instances, the diameter of each well (or other depression 28) can be at least about 50 nm, at least about 0.1 μm, at least about 0.5 μm, at least about 1 μm, at least about 10 μm, at least about 100 μm, or more. Alternatively or additionally, the diameter can be at most about $1 \times 10^3$ μm, at most about 100 μm, at most about 10 μm, at most about 1 μm, at most about 0.5 μm, at most about 0.1 μm, or less (e.g., about 50 nm). The diameter of each well (or other depression 28) can be greater than, less than or between the values specified above.

When the depression 28 is a trench (see, e.g., FIG. 34H), both the trenches and interstitial regions can have a rectilinear configuration. The depth of each trench can be at least at least about 0.02 µm (20 nm), at least about 0.1 µm (100 nm), at least about 1 µm, at least about 10 µm, at least about 100 µm, or more. Alternatively or additionally, the depth can be at most about $1\times10^3$ µm, at most about 100 µm, at most about 10 µm, at most about 1 µm, at most about 0.1 µm, or less. The depth of each trench can be greater than, less than or between the values specified above.

In some instances, the width of each trench can be at least about 0.02 µm, at least about 0.1 µm, at least about 0.5 µm, at least about 1 µm, at least about 10 µm, at least about 100 µm, or more. Alternatively or additionally, the width can be at most about $1\times10^3$ µm, at most about 100 µm, at most about 10 µm, at most about 1 µm, at most about 0.5 µm, at most about 0.1 µm, or less (e.g., about 50 nm). The width of each trench can be greater than, less than or between the values specified above.

Figure 3B:
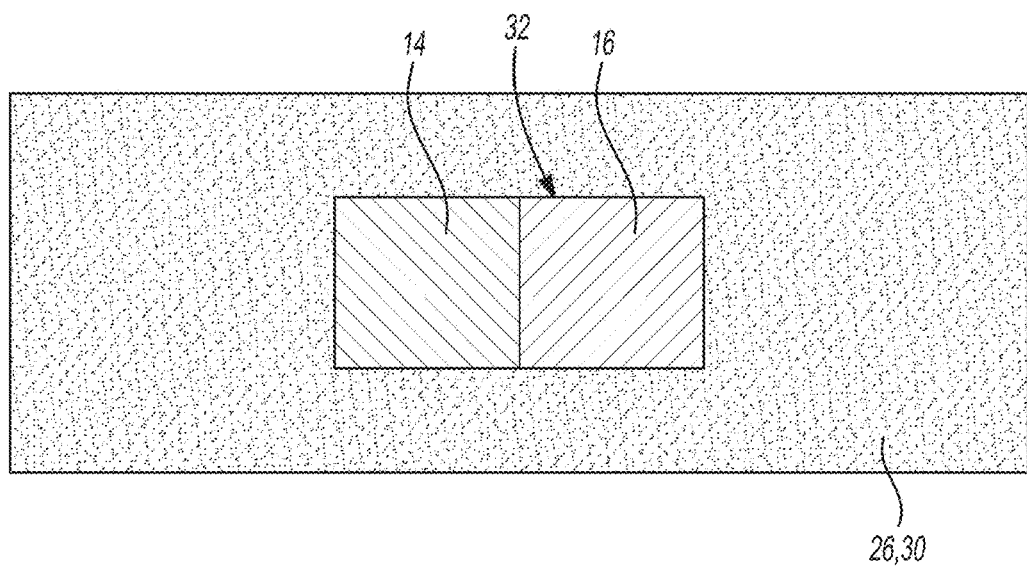

FIG. 3A and FIG. 3B depict, respectively, a cross-sectional view and a top view of an example where the regions 14, 16 are located in different areas of the depression 28. In this example, the regions 14, 16 are directly adjacent to each other within the depression 28.

One example method for making the example shown in FIG. 3A and FIG. 3B is shown in FIG. 28A through FIG. 28G. While the primer sets 12A, 12A' or 12B, 12B' or 12C, 12C' or 12D, 12D' are mentioned throughout this description, they are not shown for clarity. Moreover, FIG. 3A and FIG. 3B depict the depression 28 defined in a single layer substrate 26, while the example method depicts the depression 28 defined in a patterned resin 54' on a support 52 of a multi-layered substrate. It is to be understood that this method may be used with a single layer substrate.

In this example, the multi-layered substrate includes a (patterned) resin 54' on a support 52. Any example of the resin 54 (e.g., see the section "Bead Based Flow Cell"), the support 52, and the methods for patterning the resin 54 described herein may be used.

As shown in FIG. 28A, the depression 28 defined in the patterned resin 54' is adjacent to interstitial regions 30, which separate adjacent depressions 28 from one another. As shown in FIG. 28B, a first functionalized layer 60 is applied (e.g., deposited or deposited and cured) on the patterned resin 54' using any of the techniques described herein.

In FIG. 28C and FIG. 28D, the first functionalized layer 60 is then patterned to form a first functionalized region (region 14) covered by a photoresist 62. In this example, the photoresist 62 may be a negative photoresist (exposed region becomes insoluble) or a positive photoresist (exposed region becomes soluble). The photoresist 62 is applied to the first functionalized layer 60, is selectively exposed to certain wavelengths of light to form the insoluble or soluble region, and is exposed to a developer solution to remove the soluble portions. In other examples, the photoresist 62 may be replaced with a nanoimprint lithography resin. As shown in FIG. 28C, in this example, the photoresist 62 covers a portion of the first functionalized layer 60 that is on a first portion 76 of the depression 28 (e.g., the portion of the layer 60 that is to become the region 14) and does not cover a second portion of the first functionalized layer 60 that is on a second portion 78 of the depression 28.

As shown in FIG. 28D, the exposed portions of the first functionalized layer 60 (e.g., those not covered by the photoresist 62) may then be removed, e.g., via etching or another suitable technique. This exposes the second portion 78 of the depression 28 and the interstitial regions 30.

As shown in FIG. 28E, the second functionalized layer 64 is then applied, using any suitable deposition technique (with or without curing depending upon the material), on the photoresist 62 and on portions (e.g., the exposed surface S) of the substrate 26, including on the second portion 78 of the depression 28 and on the interstitial regions 30.

As shown in FIG. 28F, the photoresist 62 may then be lifted off, which also removes any of the second functionalized layer 64 thereon.

In FIG. 28G, a portion of the second functionalized layer 64 is removed. In particular, the second functionalized layer 64 is removed from the interstitial regions 30. In this example, removing involves polishing the second functionalized layer 64 (and any of the first functionalized layer 60 that may be present) from the interstitial regions 30.

The polishing process may be performed with a gentle chemical slurry (including, e.g., an abrasive, a buffer, a chelating agent, a surfactant, and/or a dispersant) which can remove the second functionalized layer 64 (and any of the first functionalized layer 60 that may be present) from the interstitial regions 30 without deleteriously affecting the underlying substrate 26 or patterned resin 54' at those regions. Alternatively, polishing may be performed with a solution that does not include the abrasive particles.

The chemical slurry may be used in a chemical mechanical polishing system to polish the surface of the interstitial regions 30. The polishing head(s)/pad(s) or other polishing tool(s) is/are capable of polishing the second functionalized layer 64 (and any of the first functionalized layer 60 that may be present) from the interstitial regions 30 while leaving the regions 14, 16 in the depression(s) 28 at least substantially intact. As an example, the polishing head may be a Strasbaugh ViPRR II polishing head.

Cleaning and drying processes may be performed after polishing. The cleaning process may utilize a water bath and sonication. The water bath may be maintained at a relatively low temperature ranging from about 22° C. to about 30° C. The drying process may involve spin drying, or drying via another suitable technique.

In some examples, the primers 18, 20 or 18', 20' (not shown in FIG. 28A through FIG. 28G) may be pre-grafted to the first functionalized layer 60, and thus are attached to the first functionalized region 14. Similarly, the primers 19, 21 or 19', 21' (not shown in FIG. 28A through FIG. 28G) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 28B). If the regions 14, 16 have different functional groups, the primers 18, 20 or 18', 20' may be grafted at the end of the method (e.g., at FIG. 28G), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 28E). If the regions 14, 16 have different functional groups, the primers 19, 21 or 19', 21' may be grafted at the end of the method (e.g., at FIG. 28G), because they will not graft to the surface functional groups of the region 14.

When grafting is performed during the method, grafting may be accomplished using any grafting technique disclosed herein. With any of the grafting methods, the primers 18, 20 or 18', 20' react with reactive groups of the region 14 or the primers 19, 21 or 19', 21' react with reactive groups of the region 16, and have no affinity for the patterned resin 54'.

While not shown in FIG. 28A through FIG. 28G, this example method may further include depositing a first self-assembled monolayer (SAM) on the first functionalized region 14 and depositing a second self-assembled monolayer (SAM) on the second functionalized region 16. In the example using the self-assembled monolayers, the primer sets 12A, 12A' or 12B, 12B' or 12C, 12C' or 12D, 12D' are grafted after the SAMS are formed.

Another example method for making the example shown in FIG. 3A and FIG. 3B is shown in FIG. 29A through FIG. 29H. While the primer sets 12A, 12A' or 12B, 12B' or 12C, 12C' or 12D, 12D' are mentioned throughout this description, they are not shown for clarity. Moreover, FIG. 3A and FIG. 3B depict the depression 28 defined in a single layer substrate 26, while the example method depicts the depression 28' defined in a patterned resin 54' on a support 52 of a multi-layered substrate. It is to be understood that this method may be used with a single layer substrate.

In this example, the multi-layered substrate includes the (patterned) resin 54' on the support 52. As shown in FIG. 29A, the depression 28' defined in the patterned resin 54' is adjacent to interstitial regions 30, which separate adjacent depressions 28' from one another. The depression 28' is a multi-level or multi-depth depression that includes a deep portion 70 and a shallow portion 72 which is defined, in part, by a step portion 74 of the patterned resin 54'.

In this example, a sacrificial layer is applied on the patterned resin 54' so that the sacrificial layer at least partially fills the deep portion 70 in the depression 28'. An example sacrificial layer 76 is any material that has an etch rate that is different than the resin 54' and a photoresist 62 used in the method. Examples of suitable sacrificial layer materials 76 include silicon, aluminum, negative or positive photoresists, copper, etc. These materials may be deposited using any suitable technique disclosed herein. While not shown, it is to be understood that in addition to being deposited in at least part of the deep portion 70, the sacrificial layer may also be deposited on the interstitial regions 30 and on the step portion 74, or to completely fill the depression 28'.

A portion of the sacrificial layer and a portion of the resin 54' are then sequentially removed. The sacrificial layer may first be etched back so that it is removed from the interstitial regions 30 and from the step portion 74, and so that the remaining portion of the sacrificial layer (shown at reference numeral 80 in FIG. 29B) in the deep portion 70 is substantially level with the step portion 74. As shown in FIG. 29B, several portions of the resin 54' are removed. For example, portions of the resin 54' are removed to form new (referred to as second) interstitial regions 30' that are substantially level with the remaining portion of the sacrificial layer 80, and the resin 54' is removed to get rid of the step portion 74. Removal of the step portion 74 forms an area/portion 76 of the depression 28' next to the remaining portion of the sacrificial layer 80.

As shown in FIG. 29C, the first functionalized layer 60 is applied on the remaining portion of the sacrificial layer 80, the area/portion 76, and the (second) interstitial regions 30'. As shown in FIG. 29D, a photoresist 62 is then applied on the first functionalized layer 60.

Portions of the photoresist 62 and the underlying first functionalized layer 60 may then be removed to expose the remaining portion of the sacrificial layer 80 and the interstitial regions 30'. This is shown in FIG. 29E. This removal process may be accomplished by etching with an etchant that selectively removes the portion of the photoresist 62 and the underlying first functionalized layer 60, but does not remove the remaining portion of the sacrificial layer 80. In this example, wet etching may be performed with a basic pH developer solution, such as NaOH, KOH, or TMAH (tetramethylammonium hydroxide), or dry etching may be performed with an oxygen plasma. In this example, etching is stopped when the remaining portion of the sacrificial layer 80 is exposed. This leaves a second portion (e.g., region 14) of the first functionalized layer 60 having a second portion 62" of the photoresist thereon at the area/portion 76.

As shown at FIG. 29F, the remaining portion of the sacrificial layer 80 is then removed to expose a second area/portion 78 next to the second portion (e.g., region 14) of the first functionalized layer 60. This removal process may be accomplished by etching with an etchant that selectively removes the remaining sacrificial layer 76, but does not remove second portion (e.g., region 14) of the first functionalized layer 60 having a second portion 62" of the photoresist thereon. As examples, an aluminum sacrificial layer 80 can be removed in acidic or basic conditions, a copper sacrificial layer 80 can be removed using $FeCl_3$, a photoresist sacrificial layer 80 can be removed using organic solvents, such as acetone, or in basic (pH) conditions; and a silicon sacrificial layer 80 can be removed in basic (pH) conditions.

As shown in FIG. 29G, the second functionalized layer 64 is then applied to the area/portion 78, using any suitable deposition (and if applicable, curing) technique. This forms the second functionalized region 16. As shown in FIG. 29G, the second functionalized layer 64 may also be applied on the second portion 62" of the photoresist and on the interstitial regions 30.

As shown in FIG. 29G, the second portion 62" of the photoresist may then be lifted off, which also removes any of the second functionalized layer 64 thereon. This forms the first functionalized region 14. Polishing may also be performed to remove the second functionalized layer 64 from the interstitial regions 30'.

While the example shown in FIG. 29A through 29H includes the photoresist 62, it is to be understood that if the second functionalized layer 64 does not adhere to the first functionalized layer 60, then the photoresist 62 may be omitted. Moreover, if the sacrificial layer 80 is a transparent material that the first functionalized layer 60 does not adhere to, then the sacrificial layer 80 may not be removed and the region 16 may be formed on the sacrificial layer 80.

In some examples, the primers 18, 20 or 18', 20' (not shown in FIG. 29A through FIG. 29H) may be pre-grafted to the first functionalized layer 60, and thus are attached to the first functionalized region 14. Similarly, the primers 19, 21 or 19', 21' (not shown in FIG. 29A through FIG. 29H) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 29C). If the regions 14, 16 have different functional groups, the primers 18, 20 or 18', 20' may be grafted at the end of the method (e.g., at FIG. 29H), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 29G). If the regions 14, 16 have different functional groups, the primers 19, 21 or 19', 21' may be grafted at the end of the method (e.g., at FIG. 29H), because they will not graft to the surface functional groups of the region 14.

When grafting is performed during the method, grafting may be accomplished using any grafting technique disclosed herein. With any of the grafting methods, the primers 18, 20 or 18', 20' react with reactive groups of the region 14 or the primers 19, 21 or 19', 21' react with reactive groups of the region 16, and have no affinity for the patterned resin 54'.

While not shown in FIG. 29A through FIG. 29H, this example method may further include depositing a first self-assembled monolayer (SAM) on the first functionalized region 14 and depositing a second self-assembled monolayer (SAM) on the second functionalized region 16. In the example using the self-assembled monolayers, the primer sets 12A, 12A' or 12B, 12B' or 12C, 12C' or 12D, 12D' are grafted after the SAMS are formed.

Still another example method for making the example shown in FIG. 3A and FIG. 3B is shown in FIG. 30A through FIG. 30F. While the primer sets 12A, 12A' or 12B, 12B' or 12C, 12C' or 12D, 12D' are mentioned throughout this description, they are not shown for clarity. Moreover, FIG. 3A and FIG. 3B depict the depression 28' defined in a single layer substrate 26, while the example method depicts the depression 28' defined in a patterned resin 54' on a support 52 of a multi-layered substrate. It is to be understood that this method may be used with a single layer substrate.

As shown in FIG. 30A, in this example, the multi-layered substrate includes an un-patterned resin 54 on the support 52, and the sacrificial layer 80 on the resin 54. Any examples of the resin 54, support 52, and sacrificial layer 80 may be used.

As shown in FIG. 30B, additional resin is applied to the sacrificial layer 80 and is patterned to define the depression 28' therein. The additional resin may be the same as or different than the resin 54. The depression 28' is a multi-level or multi-depth depression that includes the deep portion 70 and the shallow portion 72 which is defined, in part, by a step portion 74 of the patterned resin 54'.

As shown in FIG. 30C, a first portion of the patterned resin 54' (adjacent to the deep portion 70) and a portion of the sacrificial layer 80 underlying the deep portion 70 are etched. This exposes a portion 82 of the resin 54. In an example, the patterned resin 54' may be etched using an anisotropic oxygen plasma to expose the underlying portion of the sacrificial layer 80, and then the portion of the sacrificial layer 80 may be removed, e.g., using a BCl$_3$ and Cl$_2$ plasma.

As shown in FIG. 30D, the step portion 74 of the patterned resin 54' is etched away, e.g., using oxygen plasma. This exposes the sacrificial layer 80 that underlies the step portion 74. The etchant used can etch the resin 54', but not the sacrificial layer 80. As such, the sacrificial layer 80 acts as an etch stop, and thus portion 102' of the sacrificial layer 80 is exposed.

It is to be understood that when the resin 54' is etched, the initial interstitial regions 30 may be shortened. As such, the interstitial regions 30' are formed.

Also as shown in FIG. 30D, the first functionalized layer 60 may be deposited (and cured in some instances). The first functionalized layer 60 may not adhere to the exposed portion 102' of the sacrificial layer 80, but will adhere to the portion 82 of the resin 54 and to the interstitial regions 30' surrounding the depression 28'.

The exposed portion 102' of the sacrificial layer 80 may then be etched away (e.g., using a basic solution or FeCl$_3$ depending upon the material), and the second functionalized layer 64 may be deposited (and cured depending upon the material). As shown in FIG. 30E, the second functionalized layer 64 is applied to the newly exposed portion of the resin 54 (where portion 102' has been removed). In one example, the first functionalized layer 60 has no affinity for the second functionalized layer 64, and thus the second functionalized layer 64 does not deposit on the first functionalized layer 60. In this example of the method, as shown in FIG. 30F, polishing may be performed to remove the first functionalized layer 60 from the interstitial regions 30'.

In some examples of the method(s) of FIG. 30A through FIG. 30F, the primers 18, 20 or 18', 20' (not shown in FIG. 30A through FIG. 30F) may be pre-grafted to the first functionalized layer 60, and thus are attached to the first functionalized region 14. Similarly, the primers 19, 21 or 19', 21' (not shown in FIG. 30A-FIG. 30) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 30A or 30D). If the regions 14, 16 have different functional groups, the primers 18, 20 or 18', 20' may be grafted at the end of the method (e.g., at FIG. 30F), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 30E). If the regions 14, 16 have different functional groups, the primers 19, 21 or 19', 21' may be grafted at the end of the method (e.g., at FIG. 30F), because they will not graft to the surface functional groups of the region 14.

When grafting is performed during the method, grafting may be accomplished using any grafting technique disclosed herein. With any of the grafting methods, the primers 18, 20 or 18', 20' react with reactive groups of the region 14 or the primers 19, 21 or 19', 21' react with reactive groups of the region 16, and have no affinity for the patterned resin 54'.

While not shown in FIG. 30A through FIG. 30F, this example method may further include depositing a first self-assembled monolayer (SAM) on the first functionalized region 14 and depositing a second self-assembled monolayer (SAM) on the second functionalized region 16. In the example using the self-assembled monolayers, the primer sets 12A, 12A' or 12B, 12B' or 12C, 12C' or 12D, 12D' are grafted after the SAMS are formed.

Still another example method for making the example shown in FIG. 3A and FIG. 3B is shown in FIG. 31A through FIG. 31I. While the primer sets 12A, 12A' or 12B, 12B' or 12C, 12C' or 12D, 12D' are mentioned throughout this description, they are not shown for clarity. Moreover, FIG. 3A and FIG. 3B depict the depression 28' defined in a single layer substrate 26, while the example method depicts the depression 28' defined in a patterned resin 54' on a support 52 of a multi-layered substrate. It is to be understood that this method may be used with a single layer substrate.

As shown at FIG. 31A, the multi-layered substrate includes the (patterned) resin 54' on the support 52. The depression 28' defined in the patterned resin 54' is adjacent to interstitial regions 30, which separate adjacent depressions 28' from one another. The depression 28' is a multi-level or multi-depth depression that includes a deep portion 70 and a shallow portion 72 which is defined, in part, by a step portion 74 of the patterned resin 54'.

As shown in FIG. 31B, a first functionalized layer 60 is applied on the patterned resin 54'. The first functionalized layer 60 may be any of the examples disclosed herein and may be deposited using any of the techniques described herein.

In FIG. 31C and FIG. 31D, the first functionalized layer 60 is then patterned to form a first functionalized region (region 14) covered by a photoresist 62. In this example, the photoresist 62 is a negative photoresist (exposed region becomes insoluble). As shown in FIG. 31C, the photoresist 62 is applied to the first functionalized layer 60, is selectively exposed to certain wavelengths of light to form the insoluble region (shown at 62 in FIG. 31D), and is exposed to a developer solution to remove the soluble portions. As shown in FIG. 31D, the exposed portions of the first functionalized layer 60 (e.g., those not covered by the photoresist 62) may then be removed, e.g., via etching or another suitable technique. The remaining portion of the first functionalized layer 60 (e.g., the region 14) is at a first level of each multi-level depression. In this example, the first level is in deep portion 70 on the support 52.

In this example, a sacrificial layer 84 is applied on the photoresist 62 and portions of the resin 54' (e.g., interstitial regions 30, surface of step portion 74). The sacrificial layer 84 is shown in FIG. 31E. Any material may be used as the sacrificial layer 84 that has an etch differential relative to the resin 54'. In an example, aluminum may be used as the sacrificial layer 84.

As shown in FIG. 31F, the sacrificial layer 84 is removed from the portions of the resin 54'. The sacrificial layer 84 may first be etched back so that it is removed from the interstitial regions 30 and from the step portion 74, and so that the remaining portion of the sacrificial layer (shown at reference numeral 84' in FIG. 31F) remains on the photoresist 62 in the deep portion 70.

A region of the resin 54' (specifically the step region 74) is then removed from the multi-layer depression 28' to create an area/portion 78 that is adjacent to the first functionalized region 14 (e.g., the portion of the first functionalized layer 60 that underlies the photoresist 62 and the remaining portion of the sacrificial layer 84'. This process may also remove portions of the interstitial regions 30, resulting in new interstitial regions 30'. This removal process may be accomplished by etching with an etchant, such as oxygen plasma, that selectively removes the resin 54', but does not remove the remaining portion of the sacrificial layer 84'.

As shown in FIG. 31H, the second functionalized layer 64 is then applied, using any suitable deposition technique, on the remaining portion of the sacrificial layer 84, on the area/portion 78, and on the interstitial regions 30'.

As shown in FIG. 31I, the photoresist 62 may then be lifted off, which also removes the remaining portion of the sacrificial layer 84' and any of the second functionalized layer 64 thereon. Any of the second functionalized layer 64 on the interstitial regions 30' may also be removed via polishing.

In some examples of the method(s) of FIG. 31A through FIG. 31I, the primers 18, 20 or 18', 20' (not shown in FIG. 31A through FIG. 31I) may be pre-grafted to the first functionalized layer 60, and thus are attached to the first functionalized region 14. Similarly, the primers 19, 21 or 19', 21' (not shown in FIG. 31A through FIG. 31I) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 31B). If the regions 14, 16 have different functional groups, the primers 18, 20 or 18', 20' may be grafted at the end of the method (e.g., at FIG. 31I), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 31H). If the regions 14, 16 have different functional groups, the primers 19, 21 or 19', 21' may be grafted at the end of the method (e.g., at FIG. 31I), because they will not graft to the surface functional groups of the region 14.

When grafting is performed during the method, grafting may be accomplished using any grafting technique disclosed herein. With any of the grafting methods, the primers 18, 20 or 18', 20' react with reactive groups of the region 14 or the primers 19, 21 or 19', 21' react with reactive groups of the region 16, and have no affinity for the patterned resin 54'.

While not shown in FIG. 31A through FIG. 31I, this example method may further include depositing a first self-assembled monolayer (SAM) on the first functionalized region 14 and depositing a second self-assembled monolayer (SAM) on the second functionalized region 16. In the example using the self-assembled monolayers, the primer sets 12A, 12A' or 12B, 12B' or 12C, 12C' or 12D, 12D' are grafted after the SAMS are formed.

Throughout the processing in the examples shown in FIG. 31A through FIG. 31I, the multi-level depression 28' becomes a single-level depression 28, as shown in FIG. 3A.

Figure 4A:
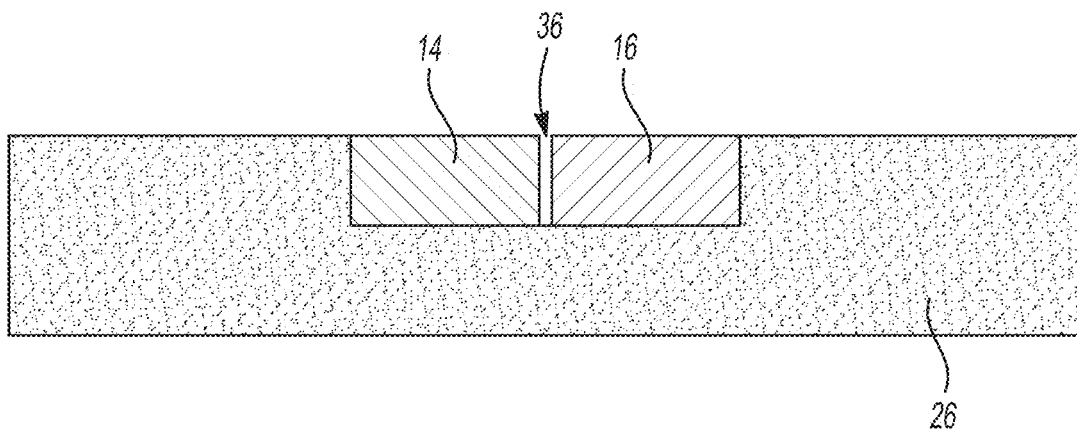
FIGS. 4A through 4C are schematic, cross-sectional views of different examples of the first and second regions in the depression.
Figure 4B:
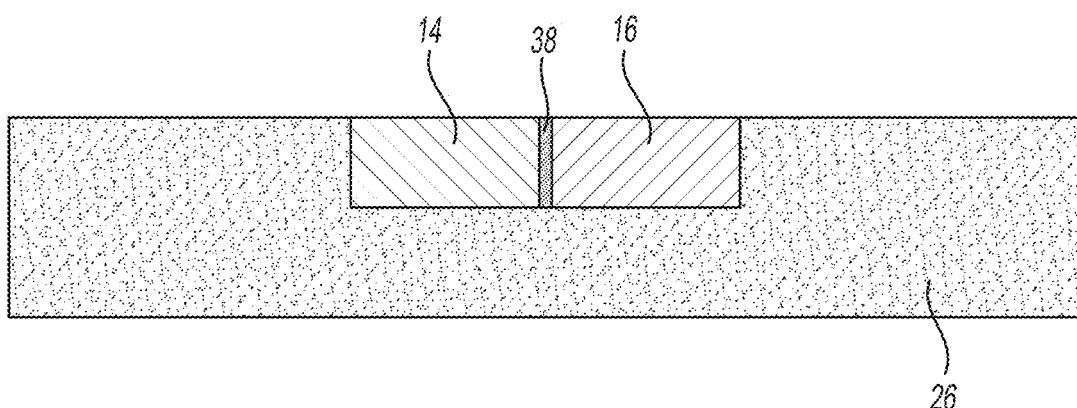
Figure 4C:
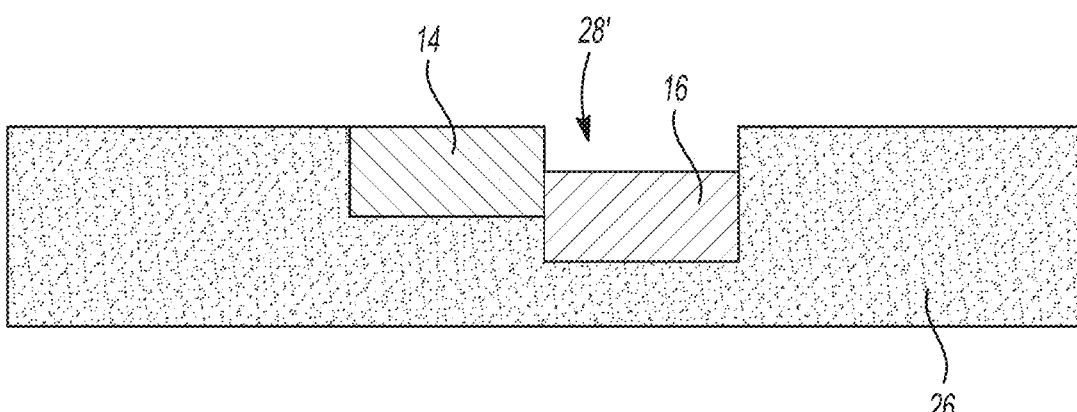

FIGS. 4A through 4C illustrate different examples of the regions 14, 16 that are located in different portions of the depression 28.

In FIG. 4A, there is a gap 36 between the regions 14, 16. As such, this example of the flow cell includes a gap 36 separating the first primer set 12A, 12B, 12C, 12D (at region 14, not shown in FIG. 4A) and the second primer set 12A', 12B', 12C', 12D' (at region 16, not shown in FIG. 4B). In one example, the gap 36 is a space between respective polymer sections where the regions 14, 16 are formed. Any of the method methods shown in FIG. 31A through FIG. 31I may be modified to form the gap 36. The gap 36 may have any measurable length greater than zero. In an example, the gap 36 is greater is 1 nm. In an example, the gap ranges from about 1 nm to about 10 nm.

In FIG. 4B, the regions 14, 16 partially overlap. The overlapping region 38 is an area where both primers 18, 20 or 18', 20' and primers 19, 21 or 19', 21' are grafted. In an example, this overlapping region 38 may be formed during the patterning and grafting process by having the same portion of the polymer layer 32 exposed when the primers 18, 20 or 18', 20' are grafted and when the primers 19, 21 or 19', 21' are grafted. In another example, this overlapping region 38 may be formed when separately grafted primers 18, 20 or 18', 20' and primers 19, 21 or 19', 21' physically overlap or interdiffuse during or after the process.

In FIGS. 4C, the first and second portions of the depression 28' where the respective regions 14, 16 are generated have different depths. Any of the depression depths described herein may be used, as long as one portion of the depression 28' is deeper than the other portion of the depression 28'. The different depths may be generated when the depression 28' is formed, e.g., via nanoimprinting, etching, etc.

One example method for making the example shown in FIG. 4C is shown in FIG. 32A through FIG. 32F. While the primer sets 12A, 12A' or 12B, 12B' or 12C, 12C' or 12D, 12D' are mentioned throughout this description, they are not shown for clarity. Moreover, FIG. 4C depicts the depression 28' defined in a single layer substrate 26, while the example method depicts the depression 28' defined in a patterned resin 54' on a support 52 of a multi-layered substrate. It is to be understood that this method may be used with a single layer substrate.

As shown at FIG. 32A, the multi-layered substrate includes the (patterned) resin 54' on the support 52. The depression 28' defined in the patterned resin 54' is adjacent to interstitial regions 30, which separate adjacent depressions 28' from one another. The depression 28' is a multi-level or multi-depth depression that includes a deep portion 70 and a shallow portion 72 which is defined, in part, by a step portion 74 of the patterned resin 54'.

As shown in FIG. 32B, a first functionalized layer 60 is applied on the patterned resin 54'. The first functionalized layer 60 may be any of the examples disclosed herein and may be deposited using any of the techniques described herein, and if suitable, may also be cured.

In FIG. 32C and FIG. 32D, the first functionalized layer 60 is then patterned to form a first functionalized region (region 14) covered by a photoresist 62. In this example, the photoresist 62 is a negative photoresist or a positive photoresist. As shown in FIG. 32C, the photoresist 62 is applied to the first functionalized layer 60, is selectively exposed to certain wavelengths of light to form the insoluble region or the soluble region (depending on the resist used), and is exposed to a developer solution to remove the soluble portions. As shown in FIG. 32D, the exposed portions of the first functionalized layer 60 (e.g., those not covered by the photoresist 62) may then be removed, e.g., via etching or another suitable technique. In this example, the first functionalized layer 60 and the resin 54' may have an etch differential. The remaining portion of the first functionalized layer 60 (e.g., region 14) is at a first level of each multi-level depression. In this example, the first level is in deep portion 70 on the resin 54'.

As shown in FIG. 32E, the second functionalized layer 64 is then applied, using any suitable deposition technique, on the exposed portions of the resin 54' (e.g., on the interstitial regions 30 and on the step region 74). Depending on the material, the second functionalized layer 64 may also be cured. In one example, the photoresist 62 has no affinity for the second functionalized layer 64, and thus the second functionalized layer 64 does not deposit on the photoresist 62. In another example, the second functionalized layer 64 may be deposited on the photoresist 62, but may be removed with the photoresist 62 is lifted off.

As shown in FIG. 32F, the photoresist 62 may then be lifted off, which, in some instances, also removes any of the second functionalized layer 64 thereon. Any of the second functionalized layer 64 on the interstitial regions 30 may also be removed via polishing.

In some examples of the method(s) of FIG. 32A through FIG. 32F, the primers 18, 20 or 18', 20' (not shown in FIG. 32A through FIG. 32F) may be pre-grafted to the first functionalized layer 60, and thus are attached to the first functionalized region 14. Similarly, the primers 19, 21 or 19', 21' (not shown in FIG. 32A through FIG. 32F) may be pre-grafted to the second functionalized layer 64, and thus are attached to the second functionalized region 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 32B). If the regions 14, 16 have different functional groups, the primers 18, 20 or 18', 20' may be grafted at the end of the method (e.g., at FIG. 32F), because they will not graft to the surface functional groups of the region 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 32E). If the regions 14, 16 have different functional groups, the primers 19, 21 or 19', 21' may be grafted at the end of the method (e.g., at FIG. 32F), because they will not graft to the surface functional groups of the region 14.

When grafting is performed during the method, grafting may be accomplished using any grafting technique disclosed herein. With any of the grafting methods, the primers 18, 20 or 18', 20' react with reactive groups of the region 14 or the primers 19, 21 or 19', 21' react with reactive groups of the region 16, and have no affinity for the patterned resin 54'.

While not shown in FIG. 32A through FIG. 32F, this example method may further include depositing a first self-assembled monolayer (SAM) on the first functionalized region 14 and depositing a second self-assembled monolayer (SAM) on the second functionalized region 16. In the example using the self-assembled monolayers, the primer sets 12A, 12A' or 12B, 12B' or 12C, 12C' or 12D, 12D' are grafted after the SAMS are formed.

Figure 5:
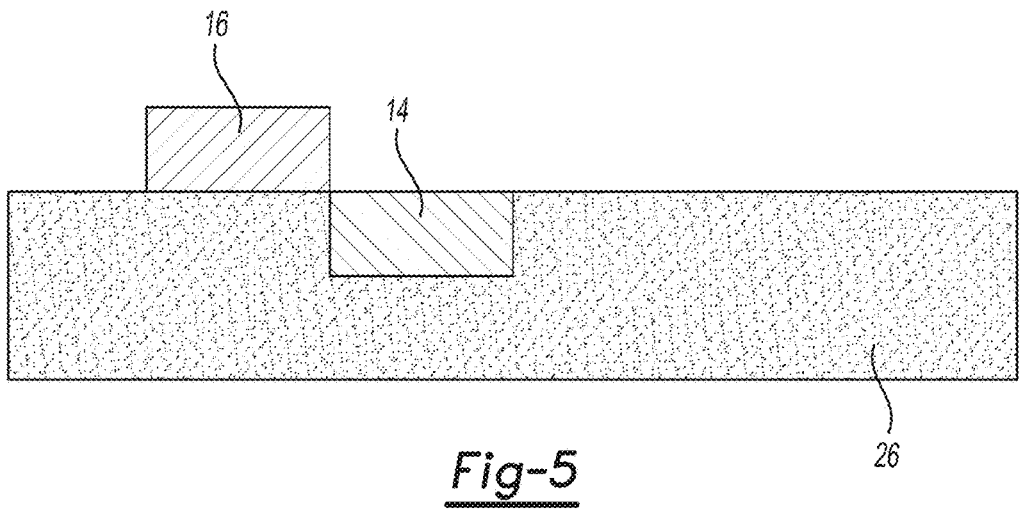
FIG. 5 is a schematic, cross-sectional view of an example of the first region in the depression and the second region on a substrate surface.
Figure 6A:
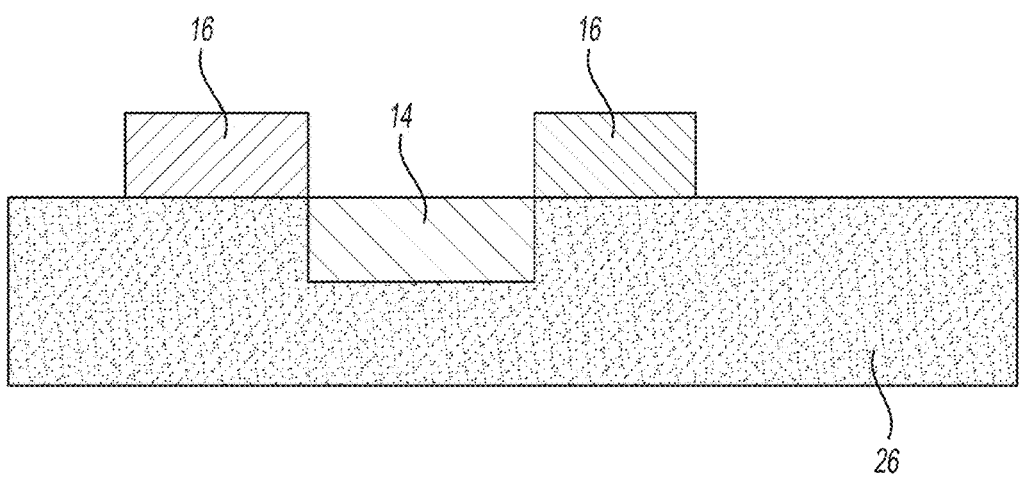
FIGS. 6A and 6B are, respectively, a schematic, cross-sectional view and a top view of an example of the first region in the depression and the second region on a substrate surface.
Figure 6B:
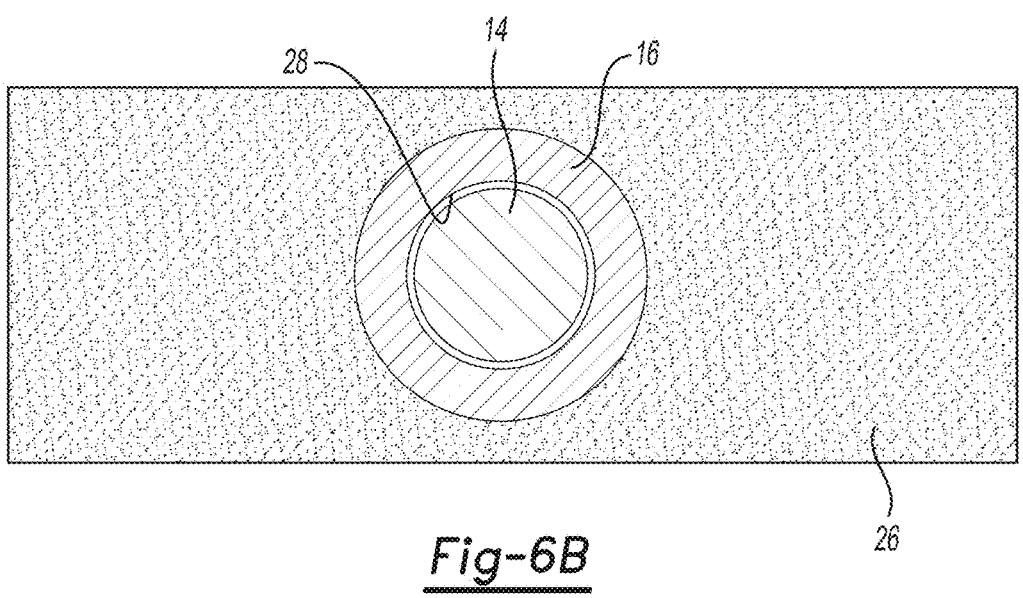

FIGS. 5, 6A and 6B illustrate different examples where the substrate 26 includes depressions 28 separated by interstitial regions 30; each of the depressions includes the first region 14; and the second region 16 is located on at least some of the interstitial regions 30. As such, in these examples, one of the regions 14 is located in the depression 28 and the other of the regions 16 is located on the substrate surface S adjacent to the depression 28. In the example shown in FIG. 5, the region 16 on the substrate surface S is next to the depression 28. In the example shown in FIGS. 6A and 6B, the region 16 on the substrate surface S surrounds the depression 28. Example methods for making one of the regions 14, 16 in the depression 28 and the other of the regions 16, 14 on at least a portion of the substrate surface S will now be described in reference to FIG. 7A through FIG. 7G and FIG. 8A through FIG. 8F.

Figure 7A:
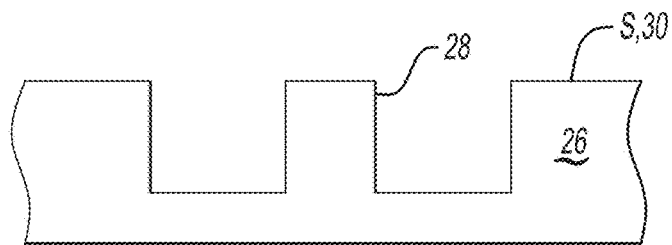
FIGS. 7A through 7G are schematic, cross-sectional view which together depict an example of a method for making an example flow cell including an example of the first region in the depression and the second region on the substrate surface.
Figure 7B:
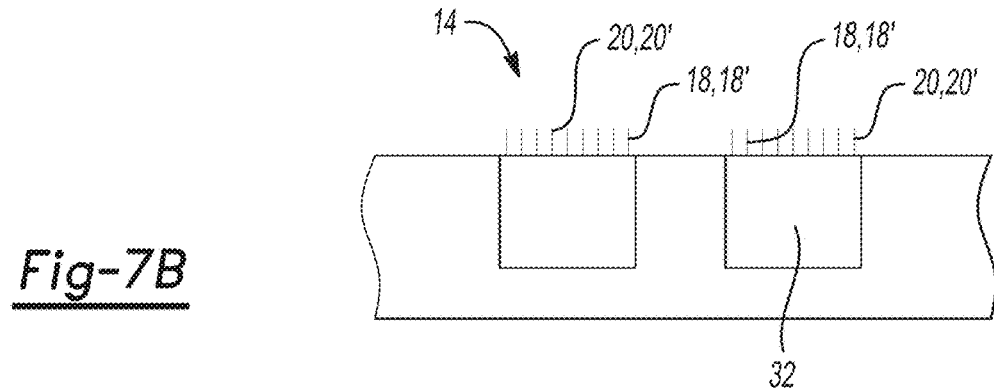

One example method for making the example shown in FIGS. 6A and 6B is shown in FIGS. 7A through 7G. As shown in FIG. 7A, the method utilizes the substrate 26 having a plurality of depressions 28 separated by interstitial regions 30. In this example method, the polymer layer 32 is deposited on the substrate 26 and polished from the interstitial regions 30 as described in reference to FIGS. 3A and 3B. This leaves the polymer layer 32 in the depression 28 and not on the interstitial regions 30. If it is desirable for the regions 14 to be in the depressions 28, then the primers 18, 20 or 18', 20' may be grafted using any of the examples disclosed herein. If it is desirable for the regions 16 to be in the depressions 28, then the primers 19, 21 or 19', 21' may be grafted using any of the examples disclosed herein. In the example shown in FIG. 7B, the primers 18, 20 or 18', 20' are grafted to the polymer layer 32. It is to be understood that the primers 18, 20 or 18', 20' will graft to the polymer layer 32 in the depression 28 and will not graft to the interstitial regions 30, as shown in FIG. 7B.

In some examples of this method, the substrate 26 (which has the region 14 or 16 formed in the depression 28) is exposed to a capping agent. The capping agent includes a chemical species that can react with any unreacted functional groups of the polymer layer 32 (e.g., any functional groups that have not reacted with a primer 18, 20 or 18', 20") in order to render these functional groups non-functional during subsequent processing. This process may reduce the ability of the subsequently deposited polymer layer 32' to adhere to the region 14. In other words, the interaction between the polymer layer 32 and the subsequently deposited polymer layer 32' is reduced so that little or no polymer layer 32' adheres to the polymer layer 32. This, in turn, reduces the ability of subsequently deposited primers (e.g., 19, 21 or 19', 21') to graft to the area overlying the region 14.

In an example where the polymer layer 32 includes azide functional groups, the chemical species in the capping agent may be a reducing agent, such as a phosphine. An example phosphine is tris(hydroxypropyl)phosphine. The non-reacted azides of the polymer layer 32 will be reduced by the phosphine, which renders them non-functional for additional primer grafting.

Figure 7C:
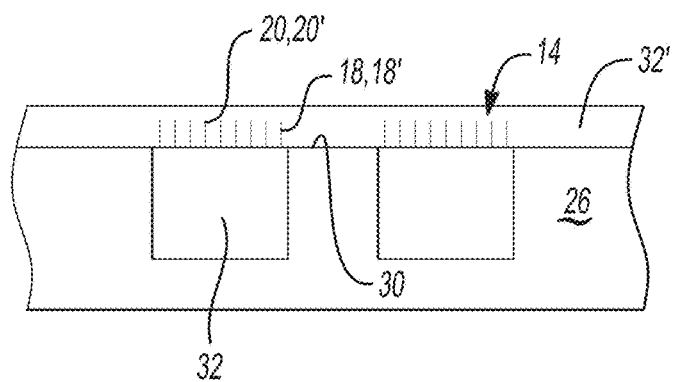

As shown in FIG. 7C, the method then includes depositing the second polymer layer 32'. The polymer layer 32' may be the same polymer that is used in the polymer layer 32, or may be a different type of polymer than that used in the polymer layer 32. In an example, each of the first polymer 32 and the second polymer 32' is an acrylamide copolymer, such as PAZAM. The polymer layer 32' may coat the interstitial regions 30 alone, or may coat at least some of the regions 14 in addition to the interstitial regions 30. Whether the polymer layer 32' at least partially coats the regions 14 will depend upon the capping agent used on the polymer layer 32.

In this example, template polynucleotide strands, including an un-cleavable first template strand 40 and a cleavable second template strand 42, may be formed in the region 14 using, respectively, the primers 18 or 18' and 20, 20'. At the outset of template polynucleotide strand formation, library templates may be prepared from any nucleic acid sample (e.g., a DNA sample or an RNA sample). The nucleic acid sample may be fragmented into single-stranded, similarly sized (e.g., <1000 bp) DNA or RNA fragments. During preparation, adapters may be added to the ends of these fragments. Through reduced cycle amplification, different motifs may be introduced in the adapters, such as sequencing binding sites, indices, and regions that are complementary to the primers 18 or 18' and 20, 20' in the regions 14. The final library templates include the DNA or RNA fragment and adapters at both ends. In some examples, the fragments from a single nucleic acid sample have the same adapters added thereto.

A plurality of library templates may be introduced to the substrate 26. This may involve introducing a template fluid to the flow cell. The template fluid may include a liquid carrier and the plurality of library templates. Because the substrate 26 includes an array of regions 14 in the depressions 28, multiple library templates are hybridized, for example, to one of two types of primers 18, 18' or 20, 20' immobilized therein.

Figure 7D:
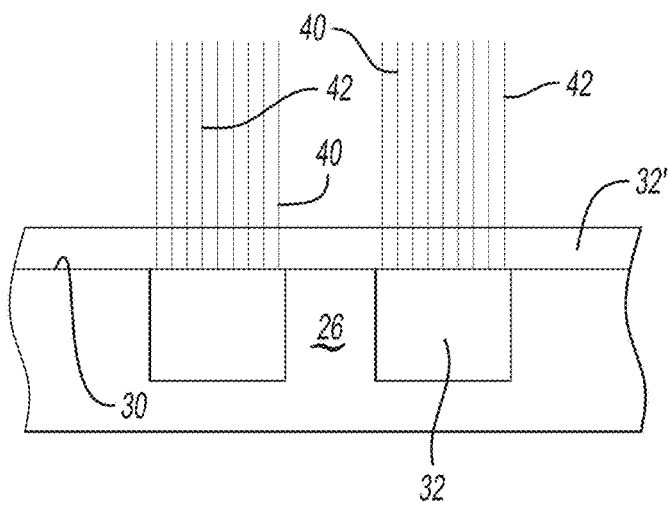

Cluster generation may then be performed. During cluster generation, a template from the template fluid is amplified to form a cluster in at least some of the depressions 28. In one example of cluster generation, the library templates are copied from the hybridized primers 18, 18' or 20, 20' by 3' extension using a high-fidelity DNA polymerase. The original library templates are denatured, leaving the copies immobilized in the regions 14. Isothermal bridge amplification may be used to amplify the immobilized copies. For example, the copied templates loop over to hybridize to an adjacent, complementary primer 20, 20' or 18, 18', and a polymerase copies the copied templates to form double stranded bridges, which are denatured to form two single stranded strands. These two strands loop over and hybridize to adjacent, complementary primers 20, 20' or 18, 18' and are extended again to form two new double stranded loops. The process is repeated on each template copy by cycles of isothermal denaturation and amplification to create dense clonal clusters. Each cluster of double stranded bridges is denatured, resulting in un-cleavable first template strands 40 attached to the un-cleavable first primers 18, 18' and cleavable second template strands 42 attached to the cleavable second primers 20, 20' as shown in FIG. 7D. It is to be understood that the cleavability of the primers drives the cleavability of the template strands attached thereto. Because the second template strands 42 attached to the cleavable second primers 20, 20' include the cleavage site 22, the cleavable second template strands 42 are cleavable. This example of clustering is bridge amplification, and is one example of the amplification that may be performed. It is to be understood that other amplification techniques may be used, such as the exclusion amplification (Examp) workflow (Illumina Inc.).

It is to be understood that because the second polymer layer 32' does not have primers 18, 18' or 20, 20' grafted thereto, the amplification process does not extend beyond the individual depressions 28.

A priming fluid may then be introduced to the substrate 26. The priming fluid includes a liquid carrier and a second primer set 12A', 12B', 12C', 12D' that is different from the first primer set 12A, 12B, 12C, 12D that has been introduced into the depressions 28. The liquid carrier in the priming fluid may be any liquid that can support click chemistry, such as phosphate buffered saline (PBS), saline-sodium citrate (SSC), a carbonate based buffer, etc. In this example, the primer set in the priming fluid includes primers 19 or 19' and 21 or 21'. It is to be understood that if the primer set 12A', 12B', 12C', 12D' (including primers 19 or 19' and 21 or 21') is grafted first to form the region 16 in the depressions 28, then the priming fluid may include the primer set 12A, 12B, 12C, 12D (including primers 18 or 18' and 20 or 20').

The primers 19 or 19' and 21 or 21' in the priming fluid may graft to the second polymer layer 32' that overlies the interstitial regions 30. Because the second polymer layer 32' may not adhere to the polymer layer 32, because amplification has been performed in the region 14, and because the functional groups of the underlying polymer layer 32 have been rendered non-functional, the primers 19 or 19' and 21 or 21' may not graft to the exposed polymer layer 32.

Figure 7E:
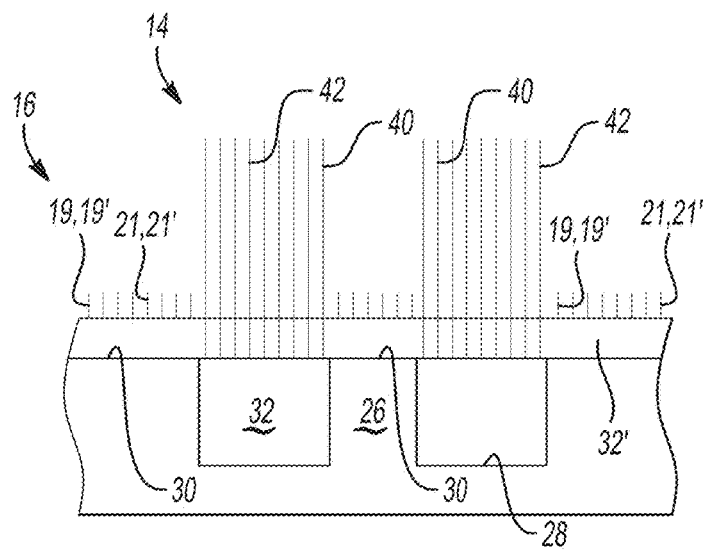

As shown in FIG. 7E, the grafted primers 19 or 19' and 21 or 21' attach to the second polymer layer 32' that overlies the interstitial regions 30, which forms the region 16.

Figure 7F:
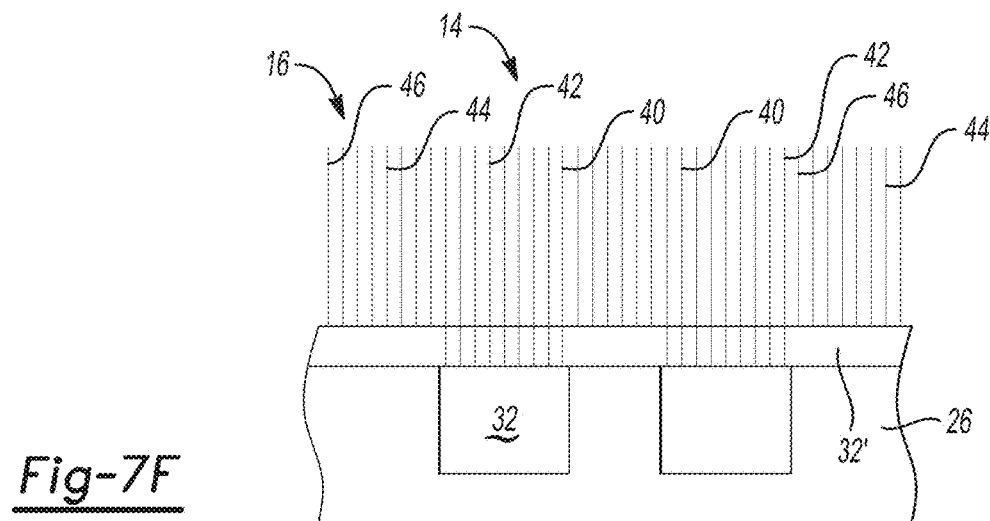

Additional amplification may then be performed. For example, bridge amplification may be initiated from the cluster to the grafted primers 19 or 19' and 21 or 21' in order to form a second cluster on at least some of the interstitial regions. During this round of amplification, the un-cleavable first template strands 40 loop over and hybridize to adjacent, complementary primers 21, 21' while the cleavable second template strands 42 loop over and hybridize to adjacent, complementary primers 19, 19'. The respective strands 40, 42 are extended to form two new double stranded loops. The process is repeated on each template copy by cycles of isothermal denaturation and amplification to create dense clonal clusters that grow out of the depressions 28 into the interstitial regions 30. Each additional cluster of double stranded bridges is denatured, resulting in un-cleavable second template strands 44 attached to the un-cleavable second primers 21, 21' and cleavable first template strands 46 attached to the cleavable first primers 19, 19' as shown in FIG. 7F. Because the cleavable first template strands 46 attached to the cleavable first primers 19, 19' include the cleavage site 22' or 23, the cleavable first template strands 46 are cleavable.

It is to be understood that when the un-cleavable first template strands 40 are forward strands, the un-cleavable second template strands 44 are reverse strands, and when the un-cleavable first template strands 40 are reverse strands, the un-cleavable second template strands 44 are forward strands. Similarly, when the cleavable first template strands 46 are forward strands, the cleavable second template strands 42 are reverse strands, and when the cleavable first template strands 46 are reverse strands, the cleavable second template strands 42 are forward strands.

Figure 7G:
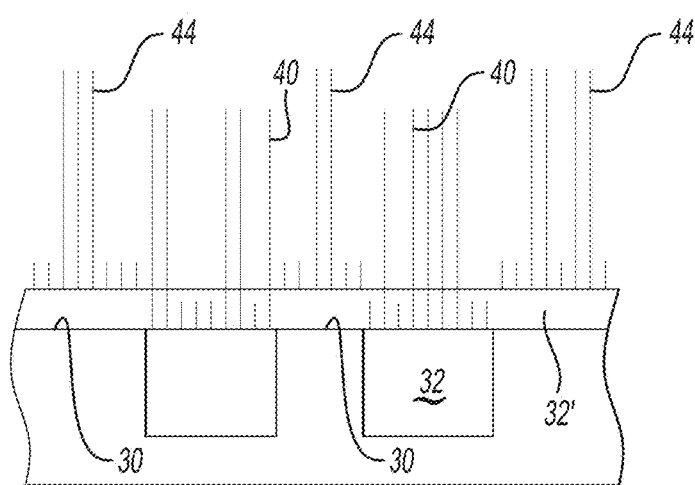

The cleavable first and second template strands 46, 42 may then be removed by introducing a chemical agent or an enzymatic cleaving agent depending on the cleavage sites 22, 22' or 22, 23. As shown in FIG. 7G, after cleavage, the un-cleavable first template strands 40 remain in the region 14 in the depression 28, and the un-cleavable second template strands 44 remain in the region 16 on the interstitial regions 30. In one example after cleavage is performed, the region 14 includes forward strands and the region 16 includes reverse strands.

Figure 8A:
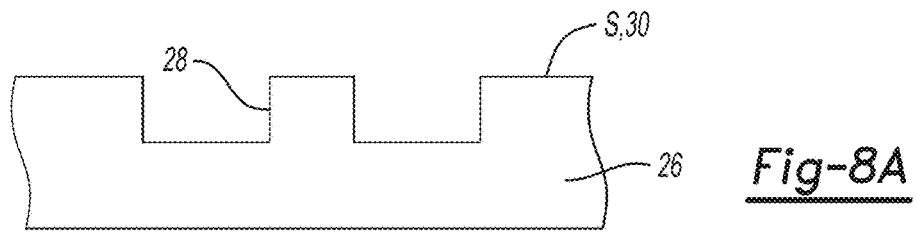
Figure 8B:
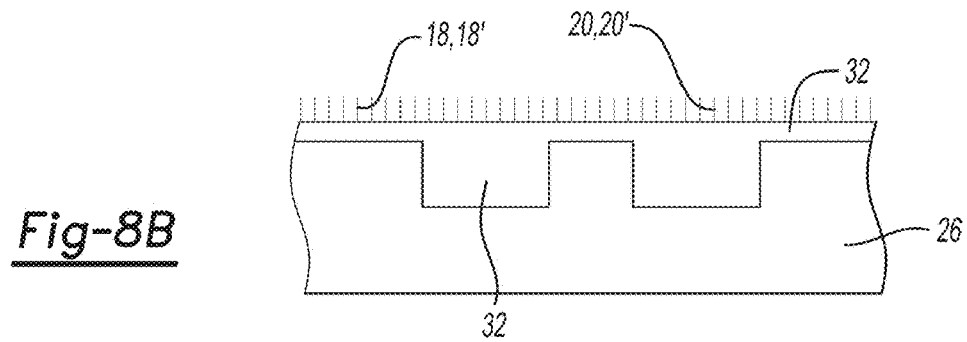

Another example method for making the examples shown in FIGS. 5, 6A and 6B is shown in FIGS. 8A through 8G. As shown in FIG. 8A, the method utilizes the substrate 26 having a plurality of depressions 28 separated by interstitial regions 30. In this example method, the polymer layer 32 is deposited on the substrate 26 so that it is present in the depressions 28 and on the interstitial regions 30. If it is desirable for the regions 14 to be in the depressions 28, then the primers 18, 20 or 18', 20' may be grafted using any of the examples disclosed herein. If it is desirable for the regions 16 to be in the depressions 28, then the primers 19, 21 or 19', 21' may be grafted using any of the examples disclosed herein. In the example shown in FIG. 8B, the primers 18, 20 or 18', 20' are grafted to the polymer layer 32. It is to be understood that the primers 18, 20 or 18', 20' will graft to the polymer layer 32 across the entire substrate 26, as shown in FIG. 8B.

Figure 8C:
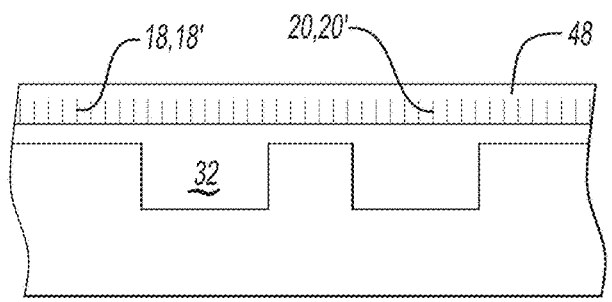

In this example method, as shown at FIG. 8C, a protective coating 48 is then deposited on the polymer layer 32 having the primer set 12A, 12B, 12C, 12D grafted thereto. The protective coating 48 may be a lift-off resist. This type of protective coating 48 may be spun on, cured, and subsequently removed at a desirable time in the process. The protective coating 48 may also be a water-soluble coating.

Figure 8D:
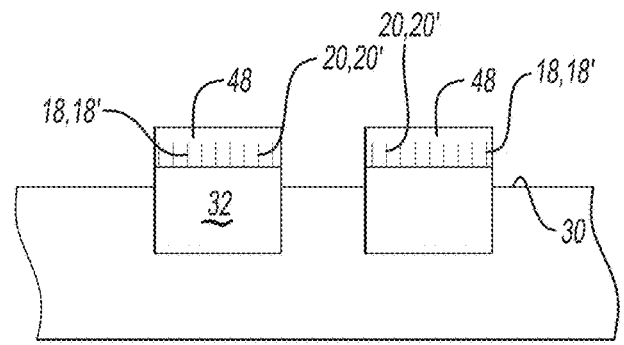

Etching may then be performed to expose those interstitial regions 30 where it is desirable to generate the region 16 including the primer set 12A', 128', 12C', 12D'. For example, an isolated section of the substrate surface S next to each depression 28 may be exposed via etching to form the example shown in FIG. 5. For another example, a section of the substrate surface S that surrounds the entire depression 28 may be exposed via etching to form the example shown in FIGS. 6A and 6B. FIG. 8D illustrates one example of the substrate 26 after etching is performed to expose the interstitial regions 30. In this example, plasma etching may be performed with air or oxygen gas.

This example method may then involve silanizing the exposed portions of the substrate surface S. Silanization introduces an adhesion promotor to the substrate surface S to help the second polymer layer 32' adhere thereto.

Figure 8E:
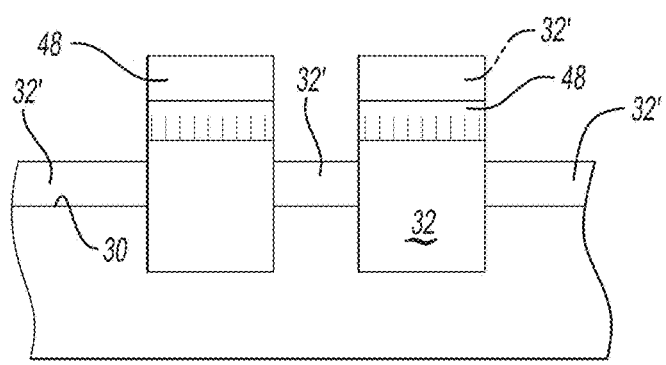

The second polymer layer 32' is then deposited. As shown in FIG. 8E, the second polymer layer 32' may be deposited on the exposed portions of the substrate surface S (e.g., at the interstitial regions 30) and on the protective coating 48. In this example method, the polymer layer 32' may be the same polymer that is used in the polymer layer 32, or may be a different type of polymer than that used in the polymer layer 32.

As shown in FIG. 8F, the primers 19, 19' and 21, 21' of the second primer set 12A', 128', 12C', 12D' may then be grafted to the polymer layer 32' to generate the regions 16. Grafting may be performed using any of the methods described herein. In another example, the polymer layer 32' may be pre-grafted with the primers 19, 19' and 21, 21'.

While not shown, it is to be understood that this example method may then include removing the protective coating 48. As an example, a lift-off method may be used to remove the protective coating 48 and any polymer layer 32' and primers 19, 19' and 21, 21' thereon. If the protective coating 48 is water soluble, removal may involve dissolving the coating 48 in water, which will also remove any overlying polymer layer 32' and primers 19, 19' and 21, 21'. Removal of the protective coating exposes all of the primer 18, 18' and 20, 20' at the regions 14 and all of the primer 19, 19' and 21, 21' at the regions 16.

While not shown in FIG. 8A through FIG. 8F, it is to be understood that a plurality of library templates may then be introduced to the substrate 26. Because the substrate 26 includes an array of regions 14 in the depressions 28, multiple library templates are hybridized, for example, to one of two types of primers 18, 18' or 20, 20' immobilized therein. In this example, because the substrate 26 also includes an array of regions 16 on at least some of the interstitial regions 30, multiple library templates are hybridized, for example, to one of two types of primers 19, 19' or 21, 21' immobilized therein. Cluster generation may then be performed as described herein. Cleavage of the cleavable templates may also be performed by cleaving the cleavable first primer 19, 19' and the cleavable second primer 20, 20'

FIG. 9 illustrates yet another example of the regions 14, 16 that are located in different portions of the depression 28'. In this example, one of the regions 14 or 16 is part of a bead 50 that is positioned in the depression 28. The bead 50 includes a core structure 49 and the region 16 at the surface of the core structure 49. In this example, the region 16 may include functional group(s) inherently present at the surface of the core structure 49, or functional group(s) incorporated on the surface of the core structure 49 through any suitable functionalization technique (e.g., chemical reaction, coating the core structure 49 with a reactive group-containing polymer, etc.).

While a single depression 28 is shown in FIG. 9, it is to be understood that in some examples, the substrate 26 includes a plurality of depressions 28 separated by interstitial regions 30; and each of the depressions includes a first portion where the first region 14 is located, and a second portion; and the flow cell further comprises a bead 50 located in the second portion, wherein the second region 16 is at a surface of the bead. Several variations of this example are further described herein in reference to FIGS. 11A through 20 in the section "Bead Based Flow Cell".

FIG. 10 depicts still another example configuration for the regions 14, 16. In this example, the regions 14, 16 are positioned on separate substrates 26, 26'. As such, this example of the flow cell includes a first substrate 26, a first primer set 12A attached to the first substrate 26, the first primer set including an un-cleavable first primer 18, 18' and a cleavable second primer 20, 20', a second substrate 26' opposed to the first substrate 26, and a second primer set 12A' attached to the second substrate 26', the second primer set 12A' including a cleavable first primer 19, 19' and an un-cleavable second primer 21, 21'. As one example of the method for making this flow cell, each of the substrates 26, 26' may be coated with the polymer layer (e.g., 32, not shown in FIG. 10), the first primer set 12A (or 12B, 12C, or 12D) may be grafted to one of the substrates 26, and the second primer set 12A' (or 12B', 12C', or 12D') may be grafted to the other of the substrates 26'.

While shown on the respective substrate surfaces S, it is to be understood that the regions 14, 16 may alternatively be positioned in depressions 28 of the respective substrates 26, 26'. In this example, the polymer layer may be deposited in the depressions 28 and on the interstitial regions 30, and then may be removed from the interstitial regions 30 via polishing. The first primer set 12A (or 12B, 12C, or 12D) may be grafted to the depressions 28 of one substrate 26, and the second primer set 12A' (or 128', 12C', or 12D') may be grafted to the depressions of the other substrate 26'.

In this example, it may be desirable for the substrates 26, 26' to be within close proximity so that template seeding and clustering may be performed successfully. In an example, "close proximity" means that the distance between the two substrates 26, 26' is about 100 μm or less. In another example, the distance between the two substrates 26, 26' ranges from about 10 μm to about 90 μm.

Instead of being positioned on separate substrates 26, 26', the first and second regions 14, 16 and primer sets 12A, 12A', or 12B, 12B', or 12C, 12C', or 12D, 12D' may be macro-separated on the substrate surface S or may be present in separate depressions 28 that are macro-separated from each other. By macro-separated it is meant that the regions 14, 16 are separated from each other by at least 5 μm. In one example, the regions 14, 16 are separated from each other by a distance ranging from about 5 μm to about 100 μm.

FIG. 33A depicts still another example configuration for the regions 14, 16. In this example, the first and second functionalized layers 60, 64 are integrated into the resin portion of the multi-layered substrate. As shown in FIG. 33A, this example of the multi-layer substrate includes a support 52; the first functionalized layer 60 on the support 52; the second functionalized layer 64 on the first functionalized layer 60; and a passivation layer 86 on the second functionalized layer 64.

In this example, the first and second functionalized layers 60, 64 may be any nanoimprint lithography resin having or capable of having introduced thereto surface functional groups that can attach to the respective primer sets 12A, 12A', or 12B, 12B', or 12C, 12C', or 12D, 12D'. In one example, layer 60 may be functionalized with epoxy groups and layer 64 may be functionalized with amine groups.

The resins of the layers 60, 64 may be the same if the respective primer sets 12A, 12A', or 12B, 12B', or 12C, 12C', or 12D, 12D' are pre-grafted into the layers 60, 64 before the multi-layer substrate shown in FIG. 33A is formed. In these examples of this method, the first primer set 12A, 12B, 12C, 12D (e.g., an un-cleavable first primer 18, 18' and a cleavable second primer 20, 20') may be pre-grafted to the first functionalized layer 60 before the first functionalized layer 60 is incorporated into the multi-layer substrate; and the second primer set 12A', 12B', 12C', 12D' (e.g., a cleavable first primer 19, 19' and an un-cleavable second primer 21, 21') may be pre-grafted to the second functionalized layer 66 before the second functionalized layer 64 is incorporated into the multi-layer substrate.

The layers (whether pre-grafted or not) may be deposited on the support 52 using any of the examples disclosed herein.

When the primers are grafted post-imprinting, it is to be understood that the layers 60, 64 at least have different surface functional groups that can attach to the respective primer sets 12A, 12A', or 12B, 12B', or 12C, 12C', or 12D, 12D'. Any of the resins disclosed herein may be used.

The passivation layer 86 may be any hydrophobic layer that can be imprinted. As examples, the passivation layer 86 is selected from the group consisting of a fluorinated polymer, a perfluorinated polymer, a silicon polymer, and a mixture thereof. As examples, the passivation layer 86 may include an amorphous fluoropolymer (commercially available examples of which include those in the CYTOP® series from AGC Chemicals, which have one of the following terminal functional groups: A type: —COOH, M type: —CONH—Si(OR)$_n$, or S type: —CF$_3$), a polytetrafluoroethylene (a commercially available example of which is TEFLON® from Chemours), parylen, a fluorinated hydrocarbon, a fluoroacrylic copolymer (a commercially available example of which includes as FLUOROPEL® from Cytonix). The passivation layer 86 may be deposited on the support 52 using any of the examples disclosed herein.

As shown in FIG. 33A, this example of the method includes imprinting the multi-layer substrate, thereby forming features (e.g., depressions 28) separated by interstitial regions 30 of the passivation layer 86, wherein a region 14, 16, respectively, of each the first and second functionalized layers is exposed at each feature/depression 28. The exposed regions 14, 16 of a single feature/depression 28 and the surrounding interstitial regions 30 of the passivation layer 86 are shown from a top view in FIG. 33B. For each region 14, 16, the feature/depression 28 has a slanted bottom or a step region, or some other variation in geometry that exposes both a portion of the layer 60 and a portion of the layer 64 from the top of the feature/depression 28.

To imprint the multi-layer substrate, a nanoimprint lithography mold or working stamp 56 is pressed against the layer of resin 54 to create an imprint of the features in the layers 60, 64, 68. In other words, the each of the layers 60, 64, 68 is indented or perforated by the protrusions of the working stamp 56. The layers 60, 64, 68 may be then be cured with the working stamp 56 in place. Curing may be accomplished by exposure to actinic radiation, such as visible light radiation or ultraviolet (UV) radiation, or to radiation of a wavelength ranging from about 240 nm and 380 nm when a photoresist is used; or by exposure to heat when a thermal-curable resist is used. Curing may promote polymerization and/or cross-linking. As an example, curing may include multiple stages, including a softbake (e.g., to drive off solvent(s)) and a hardbake. The softbake may take place at a lower temperature, ranging from about 50° C. to about 150° C. The duration of the hardbake may last from about 5 seconds to about 10 minutes at a temperature ranging from about 100° C. to about 300° C. Examples of devices that can be used for softbaking and/or hardbaking include a hot plate, oven, etc.

After curing, the working stamp 56 is released. This creates topographic features, i.e., the depressions 28, in the layers 60, 64, 68.

As mentioned, the primers 18, 20 or 18', 20' (not shown in FIG. 33A or FIG. 33B) may be pre-grafted to the first functionalized layer 60, and thus are attached to the first functionalized region 14; and the primers 19, 21 or 19', 21' (not shown in FIG. 33A or FIG. 33B) may be pre-grafted to the second functionalized layer 64, and thus are attached to the second functionalized region 16. In these examples, additional primer grafting is not performed.

In other examples, the primers 18, 20 or 18', 20' and/or the primers 19, 21 or 19', 21' are not pre-grafted, respectively, to the first functionalized layer 60 and the second functionalized layer 64. In these examples, the regions 14, 16 have different functional groups, and the primers 18, 20 or 18', 20' and primers 19, 21 or 19', 21' may be grafted after imprinting.

When grafting is performed after imprinting, grafting may be accomplished using any grafting technique disclosed herein. With any of the grafting methods, the primers 18, 20 or 18', 20' react with reactive groups of the region 14 or the primers 19, 21 or 19', 21' react with reactive groups of the region 16, and have no affinity for the passivation layer 86.

As mentioned, some examples of the depression 28 may be in the form of trenches. FIG. 34S depicts (from a top view) still another example configuration for the regions 14, 16, where they are formed in trenches 28".

As shown at FIG. 34A, the multi-layered substrate includes the (patterned) resin 54' on the support 52. The trenches 28" defined in the patterned resin 54' (e.g., an NIL resin, SiO$_2$, etc.) are adjacent to interstitial regions 30, which separate adjacent trenches 28" from one another (see, e.g., FIG. 34H, which illustrates a top view of multiple trenches 28").

As shown in FIG. 34B, a sacrificial layer 84 is applied on the resin 54' (e.g., interstitial regions 30 and in the trench 28"). Any material may be used as the sacrificial layer 84 that has an etch differential relative to the resin 54' and relative to a second sacrificial layer 88 that is used. In an example, the sacrificial layer 84 is silicon, aluminum, or chromium.

As shown in FIG. 34C, the sacrificial layer 84 is removed from the portions of the resin 54'. In this example, the sacrificial layer 84 may be etched such that a region of the sacrificial material 84" remains directly adjacent to each sidewall 90 of each of the trenches 28". After etching, interstitial regions 30 and a bottom portion of each trench 28" is exposed.

As shown in FIG. 34D, a second sacrificial layer 88 is applied on the regions of the sacrificial material 84" and on any exposed areas of the resin 54' (e.g., interstitial regions 30 and in the bottom portion of trench 28"). Any material may be used as the second sacrificial layer 88 that has an etch differential relative to the resin 54' and relative to a second sacrificial layer 84 that is used. For example, if layer 84 is silicon, then layer 88 may be aluminum or chromium.

The sacrificial layers 84, 88 may be applied using any of the deposition techniques described herein.

As shown in FIG. 34E, the second sacrificial layer 88 is removed from the regions of the sacrificial material 84" and from portions of the resin 54'. In this example, the second sacrificial layer 88 may be etched such that a region of the second sacrificial material 88" remains directly adjacent to each of the sacrificial material regions 84". In this example, after etching, interstitial regions 30 and another (smaller) bottom portion of each trench 28" is exposed.

As shown in FIG. 34F (depicting a top view), a material 92 is deposited to fill any spaces between the second sacrificial material regions 84". In other words, the additional material 92 covers the bottom portion of each trench 28", and completely separates the regions of the second sacrificial material 88'. The additional material 92 may be the same material as the resin 54'. For example, if silicon dioxide is used as the resin 54', then the additional material 92 may be silicon dioxide. The additional material 92 helps to define new tranches 28''' (in which the regions 14, 16 will be defined), which are smaller than the trenches 28".

In this example of the method, as shown in FIG. 34G, polishing may be performed to remove the additional material 92 from the interstitial regions 30'.

FIG. 34H depicts a top view of the trenches 28''' filled with the two sacrificial materials/layers 84", 88'. As shown each of the sacrificial materials/layers 84", 88' extends the length of each trench 28'''.

FIG. 34I depicts a cross-sectional view of one of the trenches 28''' filled with the two sacrificial materials/layers 84", 88'.

As shown in FIG. 34J, the sacrificial material region 84" is removed from a portion of each of the trenches 28'''. This exposes an area/portion 76 where the first functionalized region 14 is to be formed. The sacrificial material region 84" may be etched, and this etching process does not affect the resin 54' or the second sacrificial material region 88' due to the different etch rates.

In FIG. 34K, a first functionalized layer 60 is applied on the interstitial regions 30, the area 76, and the second sacrificial material region 88'. The first functionalized layer 60 may be any of the examples disclosed herein and may be deposited using any of the techniques described herein.

In FIG. 34KL and FIG. 34M, the first functionalized layer 60 is then patterned to form a first functionalized region (region 14) covered by a photoresist 62 in the area/portion 76. The photoresist 62 and the underlying first functionalized layer 60 may be polished or etched away, using the interstitial regions 30 and the second sacrificial material region 88' as an etch stop. This forms the first functionalized region 14 covered by the photoresist 62 in the area/portion 76 of the trench 28'''.

As shown in FIG. 34N, the second sacrificial material region 88' is removed from a portion of each of the trenches 28'''. This exposes an area/portion 78 where the second functionalized region 16 is to be formed. The second sacrificial material region 88' may be etched, and this etching process does not affect the resin 54' or the photoresist 62 due to the different etch rates. The exposed portion of the first functionalized layer 60 may be removed during this etching process.

In FIG. 34O, a second functionalized layer 64 is applied on the interstitial regions 30, the area 78, the photoresist 62, and any exposed portion of the region 14. The second functionalized layer 64 may be any of the examples disclosed herein and may be deposited using any of the techniques described herein.

In FIG. 34P, the photoresist 62 may then be lifted off, which removes any of the second functionalized layer 64 thereon. In any of the examples disclosed herein, sonication may be performed to improve the efficiency of the photoresist stripping or lift off process.

In FIG. 34Q, the interstitial regions 30 may be polished to remove any of the second functionalized layer 64 thereon. As shown in FIG. 34Q, the regions 14, 16 are formed in respective regions of the trench 28'''. It is to be understood that the regions 14, 16 extend the length of the trenches 28'''

(as shown in FIG. 34R). This configuration of the regions 14, 16 may be used for simultaneous paired end read sequencing using the primer sets 12A, 12A', or 12B, 12B', or 12C, 12C', or 12D, 12D' disclosed herein.

In FIG. 34R, a second photoresist 62' is applied (and exposed and developed) to form a pattern of spatially separated stripes that are at least substantially perpendicular to the trenches 28'''. This pattern leaves portions of the first functionalized regions 14 and the second functionalized regions 14 that are exposed between the spatially separated stripes, as shown in FIG. 34R. The portions of the first functionalized regions 14 and the second functionalized regions 16 that are exposed between the spatially separated stripes are removed (e.g., via etching), and then the spatially separated stripes (second photoresist 62') are removed (e.g., via etching). The regions 14, 16 underlying the spatially separated stripes (second photoresist 62') remain intact after removal of the spatially separated stripes (second photoresist 62'), as shown in FIG. 34S. In this example, the respective regions 14, 16 are isolated pairs along the trenches 28'''.

In some examples, the primers 18, 20 or 18', 20' (not shown in FIG. 34A through FIG. 34S) may be pre-grafted to the first functionalized layer 60, and thus are attached to the first functionalized regions 14. Similarly, the primers 19, 21 or 19', 21' (not shown in FIG. 34A through FIG. 34S) may be pre-grafted to the second functionalized layer 64, and thus are attached to the second functionalized regions 16. In these examples, additional primer grafting is not performed.

In other examples, the primers 18, 20 or 18', 20' are not pre-grafted to the first functionalized layer 60. In these examples, the primers 18, 20 or 18', 20' may be grafted after the first functionalized layer 60 is applied (e.g., at FIG. 34K). If the regions 14, 16 have different functional groups, the primers 18, 20 or 18', 20' may be grafted at the end of the method (e.g., at FIG. 34S), because they will not graft to the surface functional groups of the regions 16.

Similarly, the primers 19, 21 or 19', 21' may not be pre-grafted to the second functionalized layer 64. In these examples, the primers 19, 21 or 19', 21' may be grafted after the second functionalized layer 64 is applied (e.g., at FIG. 34O). If the regions 14, 16 have different functional groups, the primers 19, 21 or 19', 21' may be grafted at the end of the method (e.g., at FIG. 34S), because they will not graft to the surface functional groups of the regions 14.

When grafting is performed during the method, grafting may be performed using any example disclosed herein. With any of the grafting methods, the primers 18, 20 or 18', 20' react with reactive groups of the region 14 or the primers 19, 21 or 19', 21' react with reactive groups of the region 16, and have no affinity for the resin 54'.

In still another example of the flow cell, the regions 14, 16 may be formed on respective functionalized support structures 93, 94, as shown in FIG. 35. The functionalized support structures 93, 94 have surface functional groups that they can attach the respective primer sets 12A, 12A', or 12B, 12B', or 12C, 12C', or 12D, 12D' disclosed herein. Any example of the core structure 49 disclosed herein may be used for the functionalized support structures 93, 94. Any of the surface functional groups disclosed herein that are capable of attaching the different primer sets 12A, 12A', or 12B, 12B', or 12C, 12C', or 12D, 12D' may also be used. The functionalized support structure 93, 94 may be formed, for example, using the method(s) disclosed herein for forming the functionalized bead 50 (see the section "Bead Based Flow Cell").

In some examples, the functionalized support structures 93, 94 may also have different shapes. In some examples, the respective shapes correspond with, respectively, the shapes of the capture sites 95, 96 (shown in FIG. 36A, FIG. 36B, FIG. 37A, and FIG. 37B) on or defined in a surface S of the substrate (which may be a single layer or multi-layer substrate as described herein). For example, the functionalized support structures 93, 94 may respectively have the same shape as well capture sites 95, 96 (described below). The different shapes will aid in the functionalized support structure 93 becoming physically entrapped in the complementary shaped well capture site 95 and in the functionalized support structure 94 becoming physically entrapped in the complementary shaped well capture site 96.

In some examples, the functionalized support structures 93, 94 may also have different capture chemistry. The capture chemistry is the chemistry that enables the structures 93, 94 to attach to a desirable location on the substrate surface S. In some examples, the capture chemistry of the functionalized support structures 93, 94 respectively corresponds with the capture chemistry of the capture sites 95, 96 that is to receive the respective functionalized support structure 93, 94. For example, the functionalized support structure 93 and the capture site 95 may each include a member of one type of receptor-ligand binding pair, while the functionalized support structure 94 and the capture site 96 may each include a member of a different type of receptor-ligand binding pair. The different chemistries can help to endure that the functionalized support structures 93, 94 (and the respective regions 14, 16) are captures at desirable regions on the substrate surface S.

The capture sites 95, 96 are physically and/or chemically capable of immobilizing the respective functionalized support structure 93, 94 on the substrate 26 (or resin 54' of a multi-layer substrate). The capture sites 95, 96 may be positioned at any suitable location where it is desirable to have adjacent regions 14, 16. The position of the capture sites 95, 96 across the substrate 26 may be uniform (see FIGS. 36A and 36B) or may be non-uniform. The capture sites 95, 96 may have any suitable shape, geometry and dimensions, which may depend, at least in part, on the configuration of the capture sites 95, 96 (e.g., a patch, a well, a protrusion, etc.), and the type of functionalized support structure 93, 94 that is to be captured by the capture sites 95, 96.

In some examples, the capture sites 95, 96 are different chemical capture agents that are applied on a portion of the substrate surface S. Any examples of the chemical capture agent disclosed herein may be used. In one example, the respective chemical capture agents may be deposited in the desirable locations using microcontact printing, or another suitable technique.

In other examples, the capture sites 95, 96 include respective wells that are defined in the surface S of the substrate 26 (or resin 54'). The wells may be formed using etching or imprinting depending upon the substrate (e.g., single or multi-layer) that is used. The wells may have any suitable shape and geometry, such as those set forth herein for the depressions 28.

In some examples, the wells do not have an additional chemical capture agent added thereto. In these examples, the opening dimensions enable the respective functionalized support structure 93, 94 to self-assemble into the corresponding wells (e.g., based on shape). In other examples, the wells do have respective chemical capture agents added thereto.

Other examples of the capture sites 95, 96 include the well and a capture bead having a chemical capture agent on a surface thereof. The capture bead may be sized to fit into the wells. In some examples, the capture beads may be coplanar with or extend slightly above the adjacent interstitial regions 30, 30' so that the functionalized support structure 93, 94 that ultimately attaches thereto is not confined within the well. In an example, the capture bead is selected from the group consisting of silicon dioxide, a superparamagnetic material, polystyrene, and an acrylate. Any examples of the chemical capture agent disclosed herein may be used on the surface of the capture bead, and may be coated on the capture bead before it is introduced into the well. The configuration of the wells and beads of these capture sites 95, 96 may be such that the functionalized support structure 93, 94 (when attached) form regions 14, 16 that are adjacent to one another.

The depth of the capture sites 95, 96 well may vary depending upon whether the chemical capture agent is to be introduced thereto and whether the capture bead is to be introduced thereto. The depth may be selected at least to accommodate these materials (i.e., the material is contained within the wells). In an example, the depth of the well ranges from about 1 nm to about 5 microns.

As another example, the capture sites 95, 96 include protrusions that are defined in the substrate 26 (or in the resin 54'). The protrusions are three-dimensional structures that extend outward (upward) from an adjacent surface. The protrusions may be generated via etching, photolithography, imprinting, etc.

While any suitable three-dimensional geometry may be used for the protrusion capture sites 95, 96, a geometry with an at least substantially flat top surface may be desirable. Example protrusion geometries include a sphere, a cylinder, a cube, polygonal prisms (e.g., rectangular prisms, hexagonal prisms, etc.), or the like.

Different chemical capture agents may be applied on the top surface of the respective protrusion capture sites 95, 96. Any examples of the chemical capture agent disclosed herein may be used, and any deposition technique may be used to apply the chemical capture agent to the top surface of the protrusions.

It is to be understood that while the capture sites 95, 96 have been described as both being capture agents, wells, etc., any combination of the types of capture sites 95, 96 may be used together (e.g., capture agent and well) on the flow cell.

In FIG. 36A, the capture sites 95, 96, on the surface S have different shapes. When the functionalized support structure 93, 94 having respectively corresponding shapes are loaded into the flow cell (FIG. 36B), the functionalized support structure 93, 94 self-assemble, either by physical exclusion and/or by the capture chemistry, so that the functionalized support structures 93 attach to the capture sites 95 and the functionalized support structure 94 attach to the capture sites 96.

In FIG. 37A, the capture sites 95, 96, on the surface S also have different shapes, but are arranged differently than the example shown in FIG. 36A. When the functionalized support structure 93, 94 having respectively corresponding shapes are loaded into the flow cell (FIG. 37B), the functionalized support structure 93, 94 self-assemble, either by physical exclusion and/or by the capture chemistry, so that the functionalized support structures 93 attach to the capture sites 95 and the functionalized support structure 94 attach to the capture sites 96.

Both configurations shown in FIG. 36B and FIG. 37B result in an array of regions 14, 16 in isolated positions across the substrate surface S.

FIG. 2 through FIG. 10, FIG. 33A, FIG. 34S, FIG. 36B, and FIG. 37B illustrate different configurations for the regions 14, 16 of the flow cell without a lid bonded to the substrate 26 (or the resin 54'). While not shown, it is to be understood that the flow cells may have the lid bonded to at least a portion of the interstitial region 30, 30'. In some examples, the lid may be bonded before or after grafting of the primer sets 12A, 12A', or 12B, 12B', or 12C, 12C', or 12D, 12D'. When the lid is bonded prior to primer grafting, it is to be understood that a flow through process may be used for grafting. In the flow through process, the primer solution or mixture may be introduced into a flow channel(s) (defined between the lid and the interstitial region 30, 30') through respective input port(s) (not shown), may be maintained in the flow channel(s) for a time sufficient (i.e., an incubation period) for the primer(s) 18, 18', 20, 20', 19, 19', 21, 21' to attach to the respective regions 14, 16, and then may be removed from respective output port(s) (not shown). After primer 18, 18', 20, 20', 19, 19', 21, 21' attachment, the additional fluid(s) may be directed through the flow channel(s) to wash the now functionalized depressions and the flow channel(s).

The lid may be positioned on the interstitial region 30 so that it defines a single flow channel or multiple, fluidically separated flow channels.

The lid may be any material that is transparent to an excitation light that is directed toward the substrate 26. As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

In some examples, the lid may be integrally formed with sidewall(s) that correspond with the shape of the portion of the interstitial region 30 to which it will be bonded. For example, a recess may be etched into a transparent block to form a substantially planar (e.g., top) portion and sidewall(s) extending from the substantially planar portion. When the etched block is mounted to the interstitial region 30, the recess may become the flow channel. In other examples, the sidewall(s) and the lid may be separate components that are coupled to each other. For example, the lid may be a substantially rectangular block having an at least substantially planar exterior surface and an at least substantially planar interior surface that defines a portion (e.g., a top portion) of the flow channel (once bonded to the portion of the interstitial region 30). The block may be mounted onto (e.g., bonded to) the sidewall(s), which are bonded to the portion of the interstitial region 30 and form sidewall(s) of the flow channel. In this example, the sidewall(s) may include any of the materials set forth herein for the spacer layer (described below).

The lid may be bonded using any suitable technique, such as laser bonding, diffusion bonding, anodic bonding, eutectic bonding, plasma activation bonding, glass frit bonding, or others methods known in the art. In an example, a spacer layer may be used to bond the lid to the portion of the interstitial region 30. The spacer layer may be any material that will seal at least some of the interstitial regions 30 and the lid together.

In one example, the spacer layer may be a radiation-absorbing material that absorbs radiation at a wavelength that is transmitted by the lid and/or the substrate 26 (or, for example, a patterned resin of the substrate 26). The absorbed energy, in turn, forms the bond between the spacer layer and the lid and between the spacer layer and the substrate 26. An example of this radiation-absorbing material is black KAPTON® (polyimide containing carbon black) from DuPont (USA), which absorbs at about 1064 nm. It is to be understood that polyimide could be used without the addition of carbon black, except that the wavelength would have to be altered to one that is significantly absorbed by the natural polyimide material (e.g., 480 nm). As another example, polyimide CEN JP can be bonded when irradiated with light at 532 nm. When the spacer layer is the radiation-absorbing material, the spacer layer may be positioned at an interface between the lid and the portion of the interstitial region 30 so that the spacer layer contacts the desired bonding region. Compression may be applied (e.g., approximately 100 PSI of pressure) while laser energy at a suitable wavelength is applied to the interface (i.e., the radiation-absorbing material is irradiated). The laser energy may be applied to the interface both from the top and from the bottom in order to achieve suitable bonding.

In another example, the spacer layer may include a radiation-absorbing material in contact therewith. The radiation-absorbing material may be applied at the interface between the spacer layer and the lid as well as at the interface between the spacer layer and the portion of the interstitial region 30. As an example, the spacer layer may be polyimide and the separate radiation-absorbing material may be carbon black. In this example, the separate radiation-absorbing material absorbs the laser energy that forms the bonds between the spacer layer and the lid and between the spacer layer and the portion of the interstitial region 30. In this example, compression may be applied at the respective interfaces while laser energy at a suitable wavelength is applied to the interfaces (i.e., the radiation-absorbing material is irradiated).

Simultaneous Paired-end Sequencing Method

Any examples of the flow cell including the primer sets 12A, 12A', or 12B, 12B', or 12C, 12C', or 12D, 12D' described herein may be used in simultaneous paired-end sequencing, where the forward and reverse strands (e.g., strands 40 and 44) are read simultaneously.

Once the clusters of un-cleavable first template strands 40 are generated in the regions 14 and the clusters of un-cleavable second template strands 44 are generated in the region 16 (described in reference to FIG. 7C through FIG. 7G), the free ends may be blocked to prevent undesirable priming. It is to be understood that the free ends of any primers that remain may also be blocked.

In these methods, an incorporation mix may be added, which includes sequencing primers that are capable of respectively hybridizing to the un-cleavable first template strands 40 and the un-cleavable second template strands 44. The extension of the sequencing primers along the respective template strands 40, 44 is monitored to determine the sequence of nucleotides in the template strands 40, 44. The underlying chemical process can be polymerization (e.g., catalyzed by a polymerase enzyme) or ligation (e.g., catalyzed by a ligase enzyme). In a particular polymerase-based process, fluorescently labeled nucleotides are added to the respective sequencing primers in a template dependent fashion such that detection of the order and type of nucleotides added to the respective sequencing primers can be used to determine the sequence of the template. For example, to initiate a first sequencing by synthesis cycle, one or more labeled nucleotides, DNA polymerase, etc., may be delivered into/through the flow cell, where sequencing primer extension causes a labeled nucleotide to be incorporated into a nascent strand that is complementary to the respective template 40, 44. The incorporation events can be detected in tandem through an imaging event without substantial physical overlap of the fluorescent signals generated at the respective templates 40, 44. This allows for simultaneous base calling at the respective templates 40, 44. During an imaging event, an illumination system (not shown) may provide an excitation light to the flow cell, and images may be captured and analyzed. As examples, illumination may be accomplished with a laser, light emitting diode, planar waveguide, or the like.

In some examples, the fluorescently labeled nucleotides can further include a reversible termination property that terminates further primer extension once a nucleotide has been added to the respective templates 40, 44. For example, a nucleotide analog having a reversible terminator moiety can be added to the templates 40, 44 such that subsequent extension cannot occur until a deblocking agent is delivered to remove the moiety. Thus, for examples that use reversible termination, a deblocking reagent can be delivered to the flow cell, etc. (after detection occurs).

Wash(es) may take place between the various fluid delivery steps. The sequencing cycle can then be repeated n times to extend the template by n nucleotides, thereby detecting a sequence of length n.

Paired-end sequencing allows users to sequence both ends of a fragment and generate high-quality, alignable sequence data. Paired-end sequencing facilitates detection of genomic rearrangements and repetitive sequence elements, as well as gene fusions and novel transcripts. While one example paired-end sequencing method has been described in detail, it is to be understood that the flow cells described herein may be utilized with other sequencing protocol, for genotyping, or in other chemical and/or biological applications. In yet another example, the flow cells disclosed herein may be used for on-cell library generation.

Kits

Any example of the flow cells described herein may be part of a kit.

Some examples of the kit include the flow cell, a template mix/fluid, and an incorporation mix. These examples of the flow cell have both primer sets 12A, 12A', or 12B, 128', or 12C, 12C', or 12D, 12D' attached thereto. The template mix/fluid includes the template to be sequenced, and the incorporation mix includes sequencing primers that are capable of respectively hybridizing to the un-cleavable first template strands 40 and the un-cleavable second template strands 44 (formed using the template).

Other examples of the kit include the flow cell and the priming fluid described herein. These examples of the flow cell have one primer set 12A, 12B, 12C, or 12D attached thereto, and the priming fluid may be used to introduce the other primer set 12A', 12B', 12C', or 12D'. In one example of the kit, the flow cell includes a substrate 26 including depressions 28 separated by interstitial regions 30, a first polymer layer 32 in each of the depressions, wherein some functional groups of the first polymer layer are capped, a first primer set 12A, 12B, 12C, or 12D attached to other functional groups of first polymer layer 32 in each of the depressions 28, and a second polymer layer 32' on the interstitial regions 30; and the priming fluid includes a fluid carrier, and a second primer set 12A', 12B', 12C', or 12D' that is different from the first primer set 12A, 12B, 12C, or 12D. This example kit may also include the template mix and the incorporation mix.

Bead Based Flow Cell

FIG. 9 depicts one configuration for the flow cell, where one of the regions 14 or 16 is part of a bead 50. This section describes various examples and methods for this flow cell configuration.

Figure 11C:
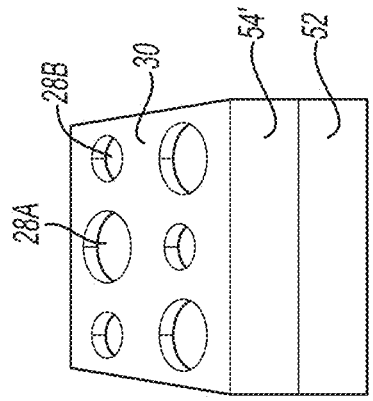
FIGS. 11A through 11C are schematic perspective views which together depict the formation of one example of a patterned resin on a support.
Figure 11B:
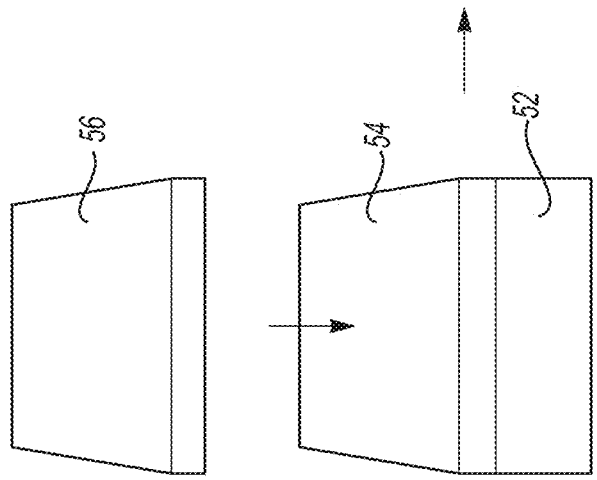
Figure 11D:
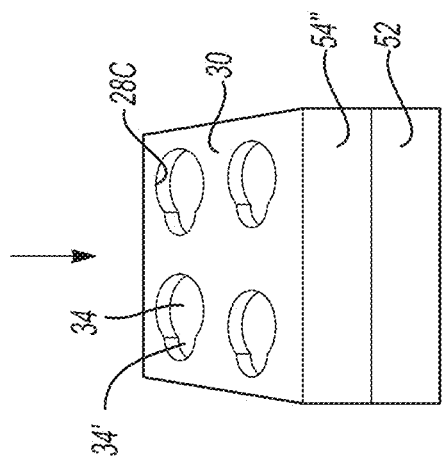
Figure 11A:
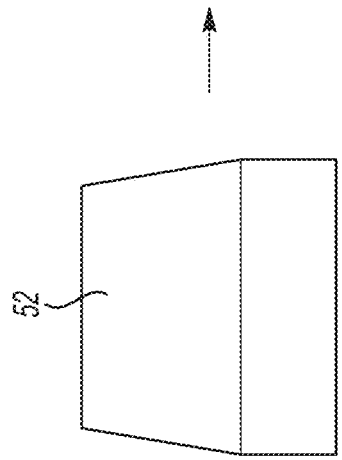

Examples of this flow cell 10A (FIGS. 13D and 14), 10B (FIGS. 15D and 16), 10C (FIGS. 17D and 18), 10D (FIGS. 19D and 20) disclosed herein include a support 52 and a patterned resin 54', 54" on the support 52, the patterned resin including depressions 28A, 28B or 28C separated by interstitial regions 30. FIGS. 11A through 11D together depict an example of a method for patterning a resin 54 to form the depressions 28A, 28B or 28C. More specifically, FIGS. 11A through 11C depict the formation of the depressions 28A, 28B, and FIGS. 11A, 11B, and 11D depict the formation of the depressions 28C.

FIG. 11A depicts a support 52, and FIG. 11B depicts a resin 54 deposited on the support 52. Any example of the substrate 12 described herein may be used for the support 52.

Some examples of suitable resins 54 are selected from the group consisting of a polyhedral oligomeric silsesquioxane resin (POSS)-based resin, an epoxy resin, a poly(ethylene glycol) resin, a polyether resin, an acrylic resin, an acrylate resin, a methacrylate resin, and combinations thereof. While several examples have been provided, it is believed that any resin that can be cured may be used.

As used herein, the terms "polyhedral oligomeric silsesquioxane" (POSS) and "POSS-based resin" refers to a chemical composition that is a hybrid intermediate ($RSiO_{1.5}$) between that of silica ($SiO_2$) and silicone ($R_2SiO$). An example of POSS can be that described in Kehagias et al., Microelectronic Engineering 86 (2009), pp. 776-778, which is incorporated by reference in its entirety. The composition is an organosilicon compound with the chemical formula $[RSiO_3/2]_n$, where the R groups can be the same or different. The composition may comprise one or more different cage or core structures as monomeric units. In some instances, the structure includes the following polyoctahedral cage or core structure. In some instances, the polyhedral structure may be a $T_8$ structure, such as:

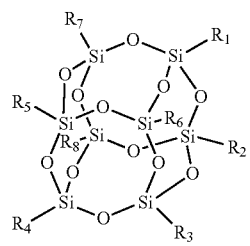

and represented by:

$T_8$

This monomeric unit typically has eight arms of functional groups $R_1$ through $R_8$.

The monomeric unit may have a cage structure with 10 silicon atoms and 10 R groups, referred to as $T_{10}$, such as:

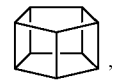

$T_{10}$ or may have a cage structure with 12 silicon atoms and 12 R groups, referred to as $T_{12}$, such as:

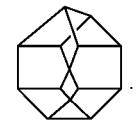

$T_{12}$

The POSS-based material may include $T_6$, $T_{14}$, or $T_{16}$ cage structures. The average cage content can be adjusted during the synthesis, and/or controlled by purification methods, and a distribution of cage sizes of the monomeric unit(s) may be used in the examples disclosed herein. As examples, any of the cage structures may be present in an amount ranging from about 30% to about 100% of the total POSS monomeric units used. The POSS-based material may be a mixture of cage structures along with open and partially open cage structures. Thus, a POSS-based resin precursor or resin may include epoxy POSS materials, which may be a mixture of silsesquioxane configurations. For example, any POSS material described herein may be a mixture of discrete POSS cages and non-discrete silsesquioxane structures and/or incompletely condensed, discrete structures, such as polymers, ladders, and the like. The partially condensed materials would therefore include epoxy R groups as described herein at some silicon vertices, but some silicon atoms would not be substituted with the R groups and could be substituted instead with OH groups. In some examples, the POSS materials comprise a mixture of various forms, such as:

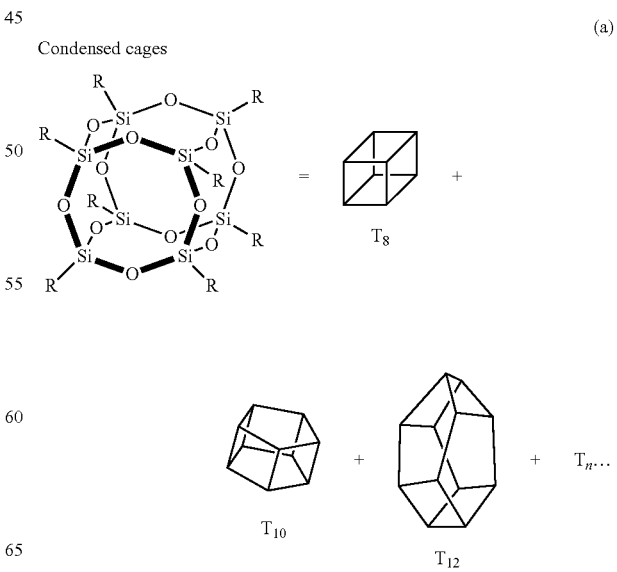

-continued

Incompletely Condensed cages

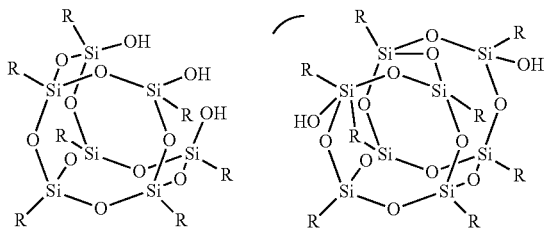

(b)

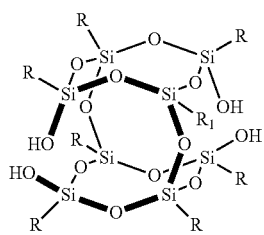

and/or (c)

Non-cage content
Large & ill-defined structure

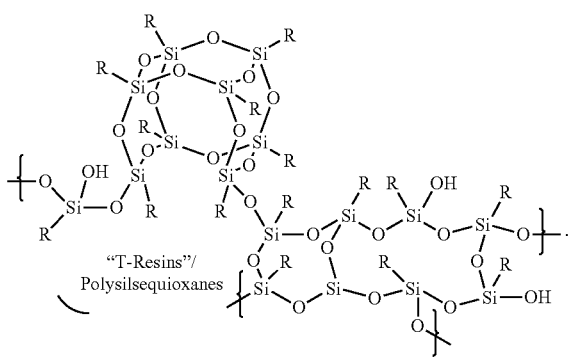

"T-Resins"/
Polysilsequioxanes

In some of the examples disclosed herein, at least one of $R_1$ through $R_8$ or $R_{10}$ or $R_{12}$ comprises an epoxy, and thus the POSS is referred to as an epoxy POSS. In some examples, a majority of the arms, such as the eight, ten, or twelve arms, or R groups, comprise epoxy groups. In other examples, $R_1$ through $R_8$ or $R_{10}$ or $R_{12}$ are the same, and thus each of $R_1$ through $R_8$ or $R_{10}$ or $R_{12}$ comprises an epoxy group. In still other examples, $R_1$ through $R_8$ or $R_{10}$ or $R_{12}$ are not the same, and thus at least one of $R_1$ through $R_8$ or $R_{10}$ or $R_{12}$ comprises epoxy and at least one other of $R_1$ through $R_8$ or $R_{10}$ or $R_{12}$ is a non-epoxy functional group. The non-epoxy functional group may be (a) a reactive group that is orthogonally reactive to an epoxy group (i.e., reacts under different conditions than an epoxy group), that serves as a handle for coupling the resin to an amplification primer, a polymer, or a polymerization agent; or (b) a group that adjusts the mechanical or functional properties of the resin, e.g., surface energy adjustments. In some examples, the non-epoxy functional group is selected from the group consisting of an azide/azido, a thiol, a poly(ethylene glycol), a norbornene, a tetrazine, an amino, a hydroxyl, an alkynyl, a ketone, an aldehyde, an ester group, an alkyl, an aryl, an alkoxy, and a haloalkyl. In some aspects, the non-epoxy functional group is selected to increase the surface energy of the resin. In these other examples, the ratio of epoxy groups to non-epoxy groups ranges from 7:1 to 1:7, or 9:1 to 1:9, or 11:1 to 1:11. In any of the examples, disubstituted or monosubstituted (terminal) epoxy group(s) allow the monomeric unit to polymerize into a cross-linked matrix upon initiation using ultraviolet (UV) light and an acid. In some aspects, the epoxy POSS comprises terminal epoxy groups. An example of this type of POSS is glycidyl POSS having the structure:

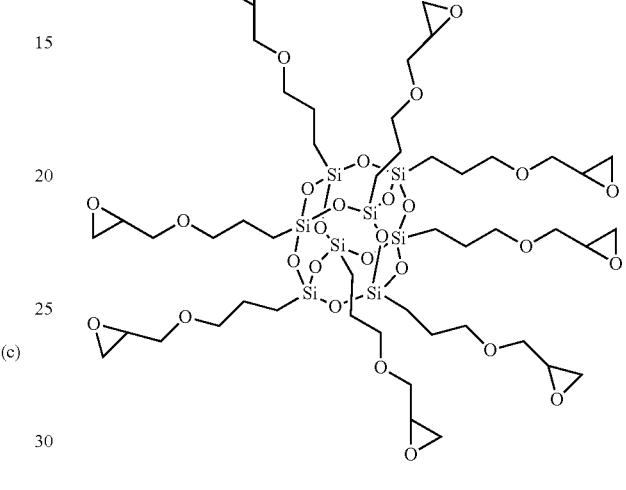

An epoxy POSS may also be a modified epoxy POSS, that includes a controlled radical polymerization (CRP) agent and/or another functional group of interest incorporated into the resin or core or cage structure as one or more of the functional group $R_1$ through $R_8$ or $R_{10}$ or $R_{12}$.

In other of the examples of the POSS-based resin disclosed herein, each of $R_1$ through $R_8$ or $R_{10}$ or $R_{12}$ comprises any non-epoxy group, such as an acrylate, methacrylate, ethylene glycol, or a short polyethylene glycol chain (up to 50 repeat units). Any non-epoxy POSS monomer that can be polymerized radically may be used. An example is a methacryl POSS cage mixture having the following structure:

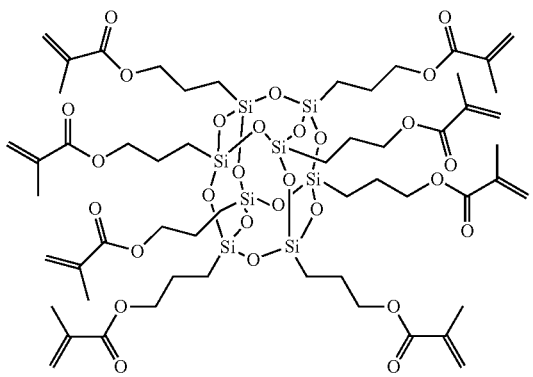

Another example is a PEG-POSS cage mixture having the following structure:

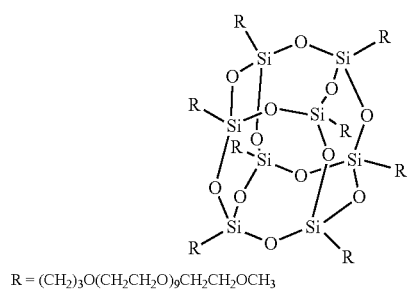

R = (CH$_2$)$_3$O(CH$_2$CH$_2$O)$_9$CH$_2$CH$_2$OCH$_3$

In the PEG-POSS example, the end methyl group (CH$_3$) of the R group may be replaced with X, where X is an acryl group, a methacryl group, or another suitable end group.

Other resins 54 may also be used. Examples include (non-POSS) epoxy resins, poly(ethylene glycol) resins, polyether resins (which may be ring opened epoxies), acrylic resins, acrylate resins, methacrylate resins, and combinations thereof. As examples, a resin including epoxy and acrylate monomers may be used, or a resin including epoxy and ethylene monomers may be used.

Another example of a suitable resin 54 is an amorphous fluoropolymer. An example of a commercially available amorphous (non-crystalline) fluoropolymer is CYTOP® from Bellex).

As shown in FIG. 11B, the resin 54 is deposited on the support 52. In an example, deposition of the resin 54 involves chemical vapor deposition, dip coating, dunk coating, spin coating, spray coating, puddle dispensing, ultrasonic spray coating, doctor blade coating, aerosol printing, screen printing, microcontact printing, or inkjet printing.

The deposited resin 54 is then patterned, using any of the patterning techniques mentioned herein. In the example shown in FIG. 11B, nanoimprint lithography is used to pattern the resin 54. After the resin 54 is deposited, it may be soft baked to remove excess solvent. A nanoimprint lithography mold or working stamp 56 is pressed against the layer of resin 54 to create an imprint on the resin 54. In other words, the resin 54 is indented or perforated by the protrusions of the working stamp 56. The resin 54 may be then be cured with the working stamp 56 in place. Curing may be accomplished by exposure to actinic radiation, such as visible light radiation or ultraviolet (UV) radiation, or to radiation of a wavelength ranging from about 240 nm and 380 nm when a photoresist is used; or by exposure to heat when a thermal-curable resist is used. Curing may promote polymerization and/or cross-linking. As an example, curing may include multiple stages, including a softbake (e.g., to drive off solvent(s)) and a hardbake. The softbake may take place at a lower temperature, ranging from about 50° C. to about 150° C. The duration of the hardbake may last from about 5 seconds to about 10 minutes at a temperature ranging from about 100° C. to about 300° C. Examples of devices that can be used for softbaking and/or hardbaking include a hot plate, oven, etc.

After curing, the working stamp 56 is released. This creates topographic features, i.e., the depressions 28A and 28B or 28C, in the resin 54. As shown in FIG. 11C, the resin 54 having the depressions 28A and 28B defined therein is referred to as the patterned resin 54'. As shown in FIG. 11D, the resin 54 having the depressions 28C defined therein is referred to as the patterned resin 54". The patterned resin 54', 54" may be subject to further hard baking to complete the cure and to lock in the imprinted topography. In some examples, the hard baking may be performed at a temperature ranging from about 60° C. to about 300° C.

The depressions 28A and 28B shown in FIG. 11C have different sizes. In this example, "different sizes" means that some of the depressions 28B have smaller opening dimensions than some other of the depressions 28A. In this example, the "opening dimension" refers to the area occupied by each depression opening on the patterned resin 54' and/or the diameter of each depression opening on the patterned resin 54'. In the example shown in FIG. 11C, the area and diameter of the opening of each of the depressions 28B is smaller than the area and diameter of the opening of each of the depressions 28A. The area and diameter of the opening of the larger depressions 28A depend upon the particle size (e.g., diameter) of the beads 50 to be introduced thereto. The area and diameter of the opening of the smaller depressions 28B are smaller than the particle size of the beads 50. These opening dimensions enable the beads 50 to self-assemble into the depressions 28A and not the depressions 28B by size exclusion.

The depressions 28C shown in FIG. 11D include two portions 34, 34' that are interconnected, but which have different sizes. In this example, "different sizes" means that the portion 34' of each of the depressions 28C has smaller opening dimensions than the portion 34. Also in this example, the "opening dimension" refers to the area occupied by each portion opening on the patterned resin 54" and/or the diameter of each portion opening on the patterned resin 54". In the example shown in FIG. 11D, the area and diameter of the opening of each of the portions 34' is smaller than the area and diameter of the opening of each of the portions 34. The area and diameter of the opening of the larger portions 34 depend upon the particle size (e.g., diameter) of the beads 50 to be introduced thereto. The area and diameter of the opening of the smaller portions 34' are smaller than the particle size of the beads 50. These opening dimensions enable the beads 50 to self-assemble into the portions 34 and not the portions 34' by size exclusion.

Examples of the area for each depression opening or portion opening on a surface can be at least about $1 \times 10^{-3}$ μm$^2$, at least about $1 \times 10^{-2}$ μm$^2$, at least about 0.1 μm$^2$, at least about 1 μm$^2$, at least about 10 μm$^2$, at least about 100 μm$^2$, or more. Alternatively or additionally, the area can be at most about $1 \times 10^3$ μm$^2$, at most about 100 μm$^2$, at most about 10 μm$^2$, at most about 1 μm$^2$, at most about 0.1 μm$^2$, at most about $1 \times 10^{-2}$ μm$^2$, or less. In some instances, the diameter of each depression 28A, 28B or portion 34, 34' can be at least about 50 nm, at least about 0.1 μm, at least about 0.5 μm, at least about 1 μm, at least about 10 μm, at least about 100 μm, or more. Alternatively or additionally, the diameter can be at most about $1 \times 10^3$ μm, at most about 100 μm, at most about 10 μm, at most about 1 μm, at most about 0.5 μm, at most about 0.1 μm, or less (e.g., about 50 nm). The area and diameter of each depression opening or portion opening can be greater than, less than or between the values specified above. Any desirable areas and diameters may be used, as long as the area and diameter of the openings of depressions 28A are larger than the area and diameter of the openings of depressions 28B, or as long as the area and diameter of the openings of portions 34 of depressions 28C are larger than the area and diameter of the openings of portions 34' of depressions 28C.

Many different layouts of the depressions 28A and 28B or 28C may be envisaged, including regular, repeating, and non-regular patterns. In an example, the depressions 28A and 28B or 28C are disposed in a hexagonal grid for close packing and improved density. Other layouts may include, for example, rectilinear (i.e., rectangular) layouts, triangular layouts, and so forth, as long as the depression 28A or the portion 34 can receive a functionalized bead 50 (e.g., cores structure 49 with region 16 formed thereon, as shown, e.g., in FIG. 13C, 14, etc.). In some examples, the layout or pattern can be an x-y format of depressions 28A and 28B or 28C that are in rows and columns. In some other examples, the layout or pattern can be a repeating arrangement of depressions 28A and 28B or 28C and/or interstitial regions 30. In still other examples, the layout or pattern can be a random arrangement of depressions 28A and 28B or 28C and/or interstitial regions 30. The pattern may include stripes, swirls, lines, triangles, rectangles, circles, arcs, checks, plaids, diagonals, arrows, squares, and/or cross-hatches.

It is to be understood that the layout or pattern of the depressions 28A and 28B or 28C may be characterized with respect to the density and/or the average pitch as described herein.

Still further, the depressions 28A and 28B or 28C may have any suitable depth.

Figure 12:
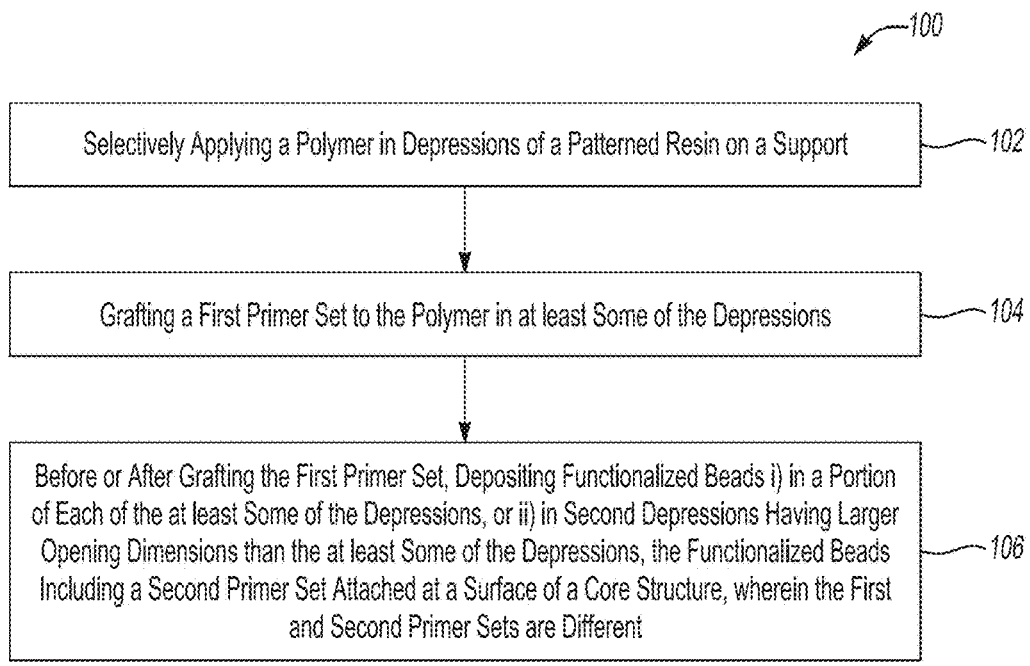
FIG. 12 is a flow diagram illustrating an example of a method disclosed herein.

An example of a method 100 for making an example of the flow cell using the patterned resin 54' shown in FIG. 11C or the patterned resin 54" shown in FIG. 11D is depicted in FIG. 12. As shown in FIG. 12, the method 100 includes selectively applying a polymer 32 in depressions 28A, 28B or 28C of a patterned resin 54' or 54" on a support 52 (reference numeral 102); grafting a first primer set 12A, 12B, 12C, 12D to the polymer 32 in at least some of the depressions 28A, 28B or 28C (reference numeral 104); and before or after grafting the first primer set 12A, 12B, 12C, 12D, depositing functionalized beads 50 i) in a portion of each of the at least some of the depressions 28C, or ii) in second depressions 28A having larger opening dimensions than the at least some of the depressions 28B, the functionalized beads 50 including a second primer set 12A', 12B', 12C', 12D', attached at a surface of a core structure 49, wherein the first and second primer sets 12A, 12A' or 12B, 12B', or 12C, 12C', or 12D, 12D' are different. Different examples of this method 100 involving the depressions 28A, 28B will be described further in reference to FIGS. 13A through 13D and 14 and FIGS. 15A through 15D and 16. Different examples of this method 100 involving the depressions 28C will be described further in reference to FIGS. 17A through 17D and 18 and FIGS. 19A through 19D and 20.

Figures 13A, 13B:
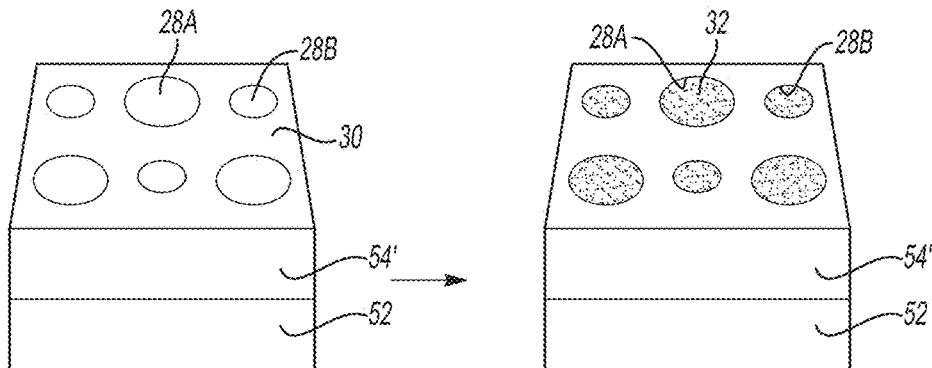
FIGS. 13A through 13D are schematic perspective views which together depict an example of the method disclosed herein using the patterned substrate of FIG. 11C.

FIG. 13A depicts the patterned resin 54' including larger depressions 28A and smaller depressions 28B. The depth of the depressions 16A and 16B is omitted for clarity.

FIG. 13B depicts the selective application of the polymer 32 into each of the depressions 28A and 28B. The selective application of the polymer 32 may involve multiple processes, including activation of the interstitial regions 30 and the exposed surfaces in the depressions 28A, 28B, depositing the polymer 32 on the activated interstitial regions 30 and in the depressions 28A, 288, and removing the polymer 32 from the interstitial regions 30.

In some examples, activation involves silanizing the surface, including the interstitial regions 30 of the patterned resin 54' and the regions of the support 52 that are exposed in the depressions 28A, 28B. Silanization may be accomplished using any silane or silane derivative. The selection of the silane or silane derivative may depend, in part, upon the polymer 32 that is to be formed, as it may be desirable to form a covalent bond between the silane or silane derivative and the polymer 32. The method used to attach the silane or silane derivative may vary depending upon the silane or silane derivative that is being used. Several examples are set forth herein.

Examples of suitable silanization methods include vapor deposition (e.g., a YES method), spin coating, or other deposition methods.

In an example utilizing the YES CVD oven, the support 52 having the patterned resin 54' thereon is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative (e.g., liquid norbornene silane) may be deposited inside a glass vial and placed inside a glass vacuum desiccator with the support 52 having the patterned resin 54' thereon. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivatives, such as those silane or silane derivative including a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo [3.3.1]non-1-ene, bicyclo[4.3.1]dec-1 (9)-ene, bicyclo [4.2.1]non-1(8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl]trimethoxysilane. As other examples, these methods may be used when the silane or silane derivative includes a cycloalkyne unsaturated moiety, such as cyclooctyne, a cyclooctyne derivative, or bicyclononynes (e.g., bicyclo[6.1.0]non-4-yne or derivatives thereof, bicyclo [6.1.0]non-2-yne, or bicyclo[6.1.0]non-3-yne). These cycloalkynes can be substituted with any of the R groups described herein.

The attachment of the silane or silane derivative forms an activated surface, both on the interstitial regions 30 and in the depressions 28A, 28B.

The polymer layer 32 may then be applied as described herein. As examples, the polymer (e.g., PAZAM) may be deposited using spin coating, or dipping or dip coating, or flow of the functionalized molecule under positive or negative pressure, or another suitable technique. The polymer deposited to form the polymer layer 32 may be present in a mixture. In an example, the mixture includes PAZAM in water or in an ethanol and water mixture.

After being coated, the mixture including the polymer may also be exposed to a curing process to form the polymer layer 32 across the activated interstitial regions 30 of the patterned resin 54' and in the depressions 28A, 28B. In an example, curing may take place at a temperature ranging from room temperature (e.g., about 25° C.) to about 95° C. for a time ranging from about 1 millisecond to about several days. In another example, the time may range from 10 seconds to at least 24 hours. In still another example, the time may range from about 5 minutes to about 2 hours.

The attachment of the polymer layer 32 to the activated (in this example silanized) surfaces may be through covalent bonding. Covalent linking is helpful for maintaining at least the first primer set 12A, 12B, 12C, 12D in the depressions 28B throughout the lifetime of the ultimately formed flow cell during a variety of uses. The following are some examples of reactions that can take place between the activated (e.g., silanized) surfaces and the polymer layer 32.

When the silane or silane derivative includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; undergo a cycloaddition reaction with a hydrazone group attached to PAZAM; undergo a photo-click reaction with a tetrazole group attached to PAZAM; or undergo a cycloaddition with a nitrile oxide group attached to PAZAM.

When the silane or silane derivative includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative includes a bicyclononyne as the unsaturated moiety, the bicyclononyne can undergo similar SPAAC alkyne cycloaddition with azides or nitrile oxides attached to PAZAM due to the strain in the bicyclic ring system.

In other examples, plasma ashing rather than silanization may be used to activate the interstitial regions 30 and the exposed surfaces of the support 52 in the depressions 28A, 28B. After plasma ashing, the mixture containing the polymer may be directly spin coated (or otherwise deposited) on the plasma ashed surfaces and then cured to form the polymer layer 32. In this example, plasma ashing may generate surface-activating agent(s) (e.g., hydroxyl (C—OH or Si—OH) and/or carboxyl groups) that can adhere the polymer to the interstitial regions 30 and the exposed surfaces of the support 52 in the depressions 28A, 28B. In these examples, the polymer 26 is selected so that it reacts with the surface groups generated by plasma ashing.

Whether activation takes place via silanization or plasma ashing, polishing may then be performed in order to remove the polymer layer 32 from the activated interstitial regions 30. Polishing may be performed as described herein. In some examples, polishing may or may not also remove the silane or silane derivative adjacent to the interstitial regions 30. When these silanized portions are completely removed, it is to be understood that the underlying patterned resin 54' is exposed.

Figures 13C, 13D:
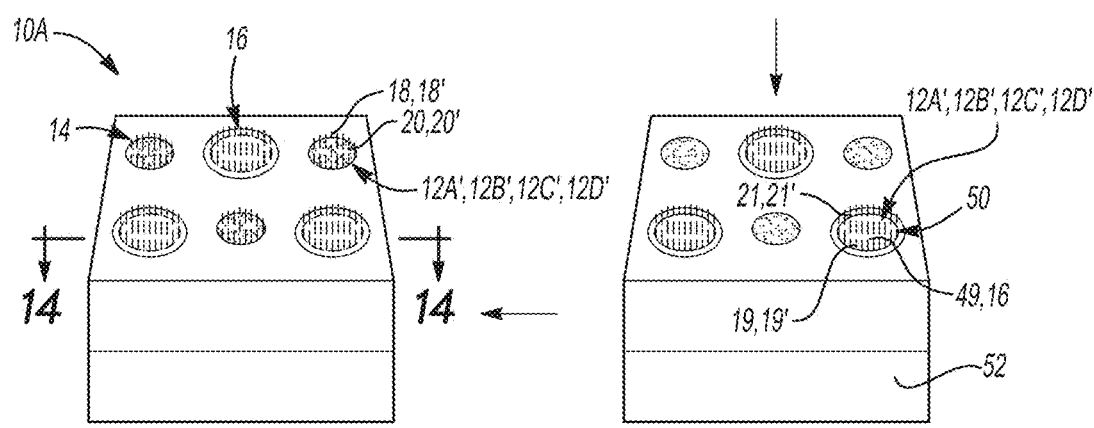

As shown in FIG. 13C, in this example of the method 100, functionalized beads 50 are deposited into the depressions 28A. Each functionalized bead 50 includes a core structure 49 and the second primer set 12A', 12B', 12C', 12D' attached at a surface of the core structure 49. The second primer set 12A', 12B', 12C', 12D' is different than the first primer set 12A, 12B, 12C, 12D as described herein. Any examples of the primer sets 12A, 12A' or 12B, 12B', or 12C, 12C', or 12D, 12D' may be used.

The core structure 49 may be any of the examples mentioned herein for the bead/core structure. In an example, the core structure 49 of the functionalized bead 50 is selected from the group consisting of silicon dioxide, a superparamagnetic material, polystyrene, and an acrylate. The core structure 49 may have reactive groups on its surface for covalent coupling to the second primer set 12A', 12B', 12C', 12D'. Examples of such reactive groups include a carboxylic acid, a primary aliphatic amine, an aromatic amine, an aromatic chloromethyl (e.g., vinyl benzyl chloride), an amide, a hydrazide, an aldehyde, a hydroxyl, a thiol, and an epoxy. These reactive group(s) may be inherently present at the surface of the core structure 49, or may be incorporated on the surface of the core structure 49 through any suitable functionalization technique (e.g., chemical reaction, coating the core structure 49 with a reactive group-containing polymer, etc.). The core structure 49 with its inherent reactive group(s) or its added reactive group(s) or coating defines the region 16.

In the examples disclosed herein that utilize the bead 50, one primer set 12A, 12B, 12C, 12D or 12A', 12B', 12C', 12D' could be functionalized with a phosphate blocking group at the 3' end which would inhibit any extension from occurring post seeding. Once the first extension occurs (with the other primer set 12A', 128', 12C', 12D' or 12A, 12B, 12C, 12D), the phosphate group would then be removed along with any strands seeded to the phosphate blocked primer set 12A, 12B, 12C, 12D or 12A', 128', 12C', 12D' and amplification between the two primer groups 12A, 12B, 12C, 12D and 12A', 12B', 12C', 12D' could then proceed. This method would help to reduce polyclonality rates since only one primer set 12A, 12B, 12C, 12D or 12A', 128', 12C', 12D' would be initially extendable.

While not shown in FIGS. 13A through 13D, prior to depositing the functionalized beads 50, the method 100 may include forming the functionalized beads 50 by attaching the second primer set 12A', 12B', 12C', 12D' to the core structure 49. Functionalization may take place using any suitable technique, including reacting an azido (e.g., succinimidyl (NHS) ester) terminated primer with a hydrazine on the surface of the core structure 49, or reacting an alkyne terminated primer with an azide on the surface of the core structure, or reacting an amino terminated primer to an activated carboxylate group or NHS ester on the surface of the core structure 49, or a thiol terminated primer with an alkylating reactant (e.g., iodoacetamine or maleimide), a phosphoramidite terminated primer with a thioether, or a biotin-modified primer with streptavidin on the surface of the core structure 49. Some nucleic acid primers 19, 19', 21, 21' can be captured onto silica beads in the presence of a chaotropic agent (KI, NI, or NaSCN). As one specific example, a dibenzocyclooctyne (DBCO, which includes an alkyne) terminated primer may be used for copper free click grafting.

The functionalized beads 50 may be deposited onto the patterned resin 54' using any suitable technique. As one example, the functionalized beads 50 may be mixed in a liquid carrier (e.g., water), which can be loaded onto the surface of the patterned resin 54'. In another example, the functionalized beads 50 may be forcefully embedded into the depressions 28A by shaking the beads 50 with 50 μm to 150 μm steel beads in a shaker that also includes the support 52 having the patterned resin 54' thereon. Because of the size of the functionalized beads 50 and the size of the depressions 28A and 28B, size exclusion will prevent the functionalized beads 50 from entering the smaller depressions 28B and will enable one functionalized bead 50 to self-assemble into one depression 28A. The functionalized beads 50 may be physically entrapped in the respective depressions 28A. The functionalized beads 50 may alternatively be chemically attached in the respective depressions 28A, e.g., via streptavidin/biotin linkers.

As shown in FIG. 13D, the depressions 28B may then be functionalized with the first primer set 12A, 12B, 12C, 12D. The primers 18, 18' and 20, 20' may be any of the examples disclosed herein, and includes a functional group that can attach to a reactive group of the polymer layer 32. Because the polymer layer 32 in the depressions 28A is covered with the functionalized beads 50, the polymer layer 32 in the depressions 28A is not exposed, and thus its reactive groups are not available for reaction with the first primer set 12A, 12B, 12C, 12D.

The primers 18, 18' and 20, 20' may be any of the examples set forth herein, and are different from one another and different from primers 19, 19' and 21, 21'. For example, if primers 21, 19 include P5 and P7U primers, then primers 20, 18 may include the P5U and P7 primers. In this example, the first primer set 12A includes an un-cleavable first primer 18 (e.g., P7) and a cleavable (e.g., uracil-modified) second primer (e.g., P5U); and the second primer set 12A' includes a cleavable (e.g., uracil-modified) first primer 19 (e.g., P7U) and an un-cleavable second primer 21 (e.g., P5). As discussed herein, the chemistry of the primer sets 12A, 12A' or 12B, 12B' or 12C, 12C' or 12D, 12D' is orthogonal, which allows for amplification across both primer populations (sets 12A, 12A' or 128, 12B' or 12C, 12C' or 12D, 12D'), and cleavage of some of the generated template strands (e.g., 42, 46), leaving the same (forward or reverse) template strands 40 or 44 in a particular region 14 or 16. This enables distinguishable read 1 and read 2 signals to be obtained simultaneously.

A grafting process may be performed to graft the primers 18, 18' and 20, 20' to the polymer layer 32 in the depressions 28B. In an example, grafting may be accomplished by flow through deposition (e.g., using a temporarily bound lid), dunk coating, spray coating, puddle dispensing, or by another suitable method that will attach the primer(s) 18, 18' and 20, 20' to the polymer layer 32 in the depressions 28B. Each of these example techniques may utilize a primer solution or mixture, which may include the primer(s), water, a buffer, and a catalyst.

Dunk coating may be used because the functionalized beads 50, in this example, are functionalized prior to being introduced into the depressions 28A and thus are not reactive with the dunk chemistry. Dunk coating may involve submerging the support 52 as shown in FIG. 13C (with patterned resin 54' thereon and functionalized beads 50 in depressions 28A) into a series of temperature controlled baths. The baths may also be flow controlled and/or covered with a nitrogen blanket. The baths may include the primer solution or mixture. Throughout the various baths, the primer(s) 18, 18' and 20, 20' attach to reactive group(s) of the polymer layer 32. In an example, the support 52 will be introduced into a first bath including the primer solution or mixture where a reaction takes place to attach the primer(s) 18, 18' and 20, 20', and then moved to additional baths for washing. Movement from bath to bath may involve a robotic arm or may be performed manually. A drying system may also be used in dunk coating.

Spray coating may be accomplished by spraying the primer solution or mixture directly onto the support 52 as shown in FIG. 13C (with patterned resin 54' thereon and functionalized beads 50 in depressions 28A). The spray coated wafer may be incubated for a time ranging from about 4 minutes to about 60 minutes at a temperature ranging from about 0° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the support 52 as shown in FIG. 13C (with patterned resin 54' thereon and functionalized beads 50 in depressions 28A). The applied primer solution or mixture may be applied to or spread across the entire surface, including on the functionalized beads 50 and the interstitial regions 30. The primer coated substrate may be incubated for a time ranging from about 2 minutes to about 60 minutes at a temperature ranging from about 0° C. to about 80° C. After incubation, the primer solution or mixture may be diluted and removed using, for example, the spin coater.

With any of the grafting methods, the primers 18, 18' and 20, 20' react with reactive groups of the exposed polymer layer 32 in the depressions 28B and have no affinity for the functionalized beads 50 or the interstitial regions 30 of the patterned resin 54'. As such, the primers 18, 18' and 20, 20' selectively graft to the polymer layer 32 in the depressions 28B.

Figure 14:
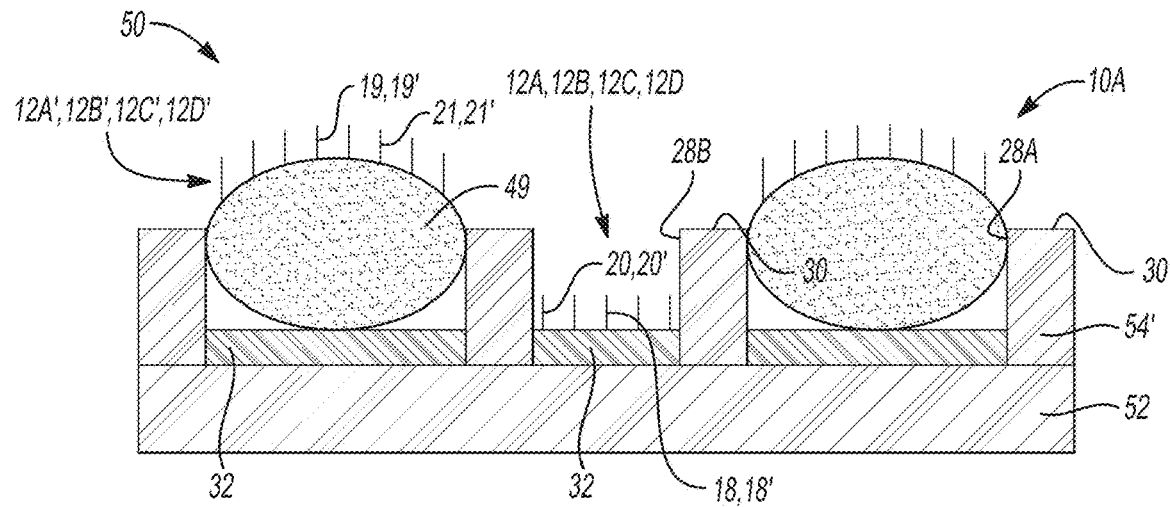
FIG. 14 is a cross-sectional view taken along line 4-4 of FIG. 13D.

FIG. 14 is a cross-sectional view of the portion of the flow cell 10A depicted in FIG. 13D. The flow cell 10A includes the support 52; the patterned resin 54' on the support 52, the patterned resin 54' including first depressions 28B and second depressions 28A separated by interstitial regions 30, the first depressions 28B having smaller opening dimensions than the second depressions 28A; the first primer set 12A, 12B, 12C, or 12D (including primers 18, 18' and 20, 20') attached in at least some of the first depressions 28B; and the functionalized bead 50 respectively positioned in at least some of the second depressions 28A, the functionalized bead 50 including a second primer set 12A', 12B', 12C', or 12D' (including primers 19, 19' and 21, 21') attached at a surface of a core structure 49, wherein the second primer set 12A', 12B', 12C', or 12D' is different than the first primer set 12A, 12B, 12C, or 12D. In the example shown in FIGS. 13D and 14, the polymer layer 32 is present in the first depressions 28B and in the second depressions 28A, and the first primer set 12A, 12B, 12C, or 12D is attached to the polymer layer 32 in the at least some of the first depressions 28B. Moreover, in the example shown in FIGS. 13D and 14, the functionalized beads 50 are positioned on the polymer layer 32 in at least some of the second depressions 28A.

Figures 15A, 15B:
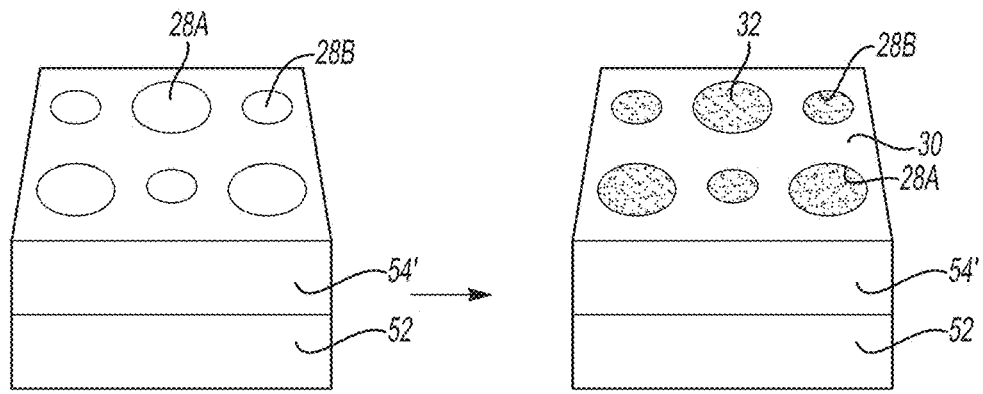
FIGS. 15A through 15D are schematic perspective views which together depict another example of the method disclosed herein using the patterned substrate of FIG. 11C.

Referring now to FIGS. 15A through 15D, another example of the method 100 involving the depressions 28A, 28B is shown. FIG. 15A depicts the patterned resin 54' including larger depressions 28A and smaller depressions 28B. The depth of the depressions 28A and 28B is omitted for clarity.

FIG. 15B depicts the polymer layer 32 in each of the depressions 28A and 28B. The polymer layer 32 may be selectively applied as described herein, which may include activating the interstitial regions 30 and the exposed surfaces in the depressions 28A, 28B, depositing the polymer layer 32 on the activated interstitial regions 30 and in the depressions 28A, 28B, and removing the polymer layer 32 from the interstitial regions 30.

Figures 15C, 15D:
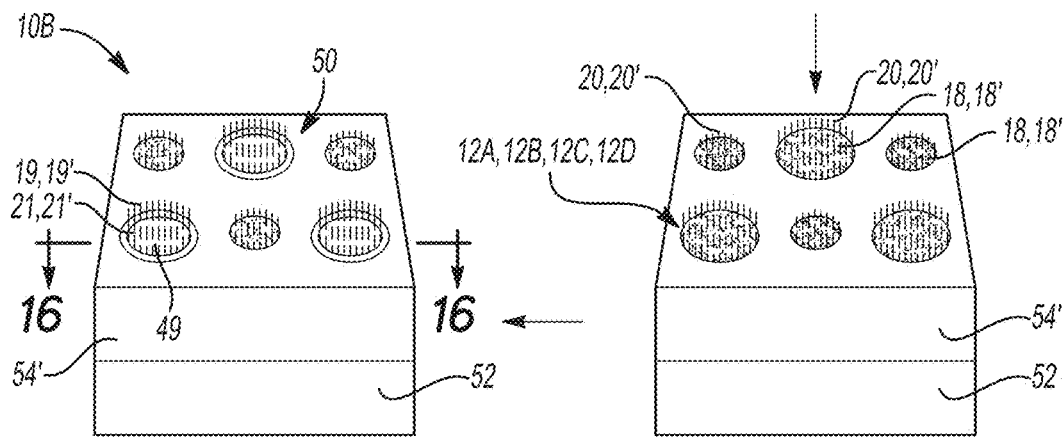

In this example, as shown in FIG. 15C, the primer set 12A, 12B, 12C, 12D (including primers 18, 18' and 20, 20') is then grafted to the polymer layer 32 in each of the depressions 28A, 28B. Because the functionalized beads 50 have not been introduced, the polymer layer 32 in each of the depressions 28A, 28B is exposed, and thus its reactive groups are available for reaction with the first primer set

12A, 12B, 12C, 12D. Grafting may be accomplished using any of the techniques described in reference to FIG. 13D. Since the polymer layer 32 is exposed in each of the depressions 28A, 28B, the primers 18, 18' and 20, 20' can be grafted into each of the depressions 28A, 28B.

As shown in FIG. 15D, the functionalized beads 50 may then be introduced into the depressions 28A (having the polymer layer 32 and primer set 12A, 12B, 12C, 12D therein). The functionalized beads 50 may be deposited onto the patterned resin 54' using any suitable technique. Because of the size of the functionalized beads 50 and the size of the depressions 28A and 28B, size exclusion will prevent the functionalized beads 50 from entering the smaller depressions 28B and will enable one functionalized bead 50 to self-assemble into one depression 28A. In this example, the functionalized beads 50 may be physically entrapped in the respective depressions 28A. Alternatively in this example, the functionalized beads 50 may be chemically attached in the respective depressions 28A, e.g., via streptavidin/biotin linkers.

Figure 16:
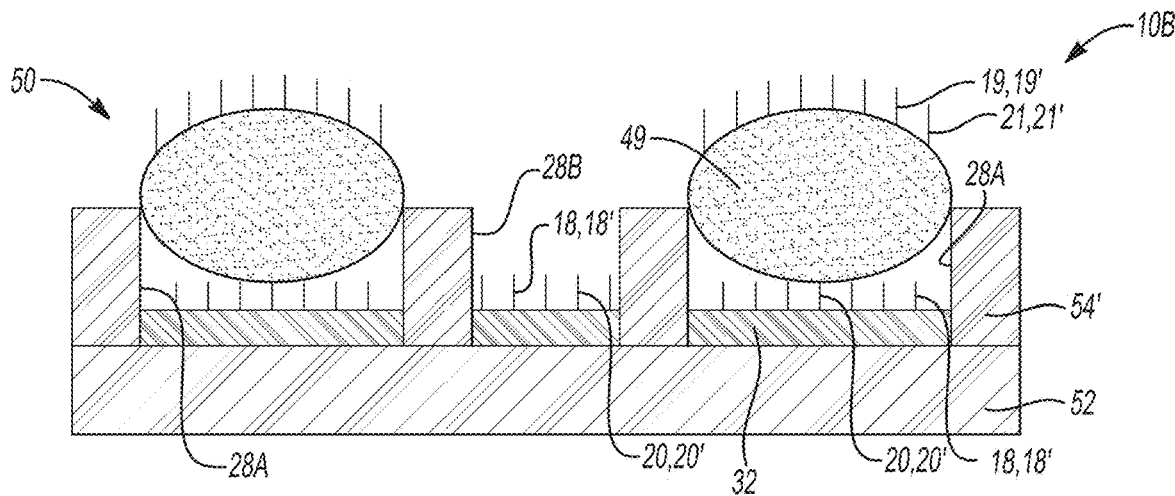
FIG. 16 is a cross-sectional view taken along line 6-6 of FIG. 15D.

FIG. 16 is a cross-sectional view of the portion of the flow cell 10B depicted in FIG. 15D. The flow cell 10B includes the support 52; the patterned resin 54' on the support 52, the patterned resin 54' including first depressions 28B and second depressions 28A separated by interstitial regions 30, the first depressions 28B having smaller opening dimensions than the second depressions 28A; the first primer set 12A, 12B, 12C, 12D (including primers 18, 18' and 20, 20') attached in at least some of the first depressions 28B; and the functionalized bead 50 respectively positioned in at least some of the second depressions 28A, the functionalized bead 50 including a second primer set 12A', 12B', 12C', 12D' (including primers 19, 19' and 21, 21') attached at a surface of a core structure 49, wherein the second primer set 12A', 12B', 12C', 12D' is different than the first primer set 12A, 12B, 12C, 12D. In the example shown in FIGS. 15D and 16, the polymer layer 32 is present in the first depressions 28B and in the second depressions 28A, and the first primer set 12A, 12B, 12C, 12D is attached to the polymer layer 32 in the first depressions 28B and in the second depressions 28A. In this example then, the functionalized bead 50 is positioned on the first primer set 12A, 12B, 12C, 12D (including primers 18, 18' and 20, 20') in the at least some of the second depressions 28A.

Referring now to FIGS. 17A through 17D, an example of the method 100 involving the depressions 28C is shown.

Figure 17A:
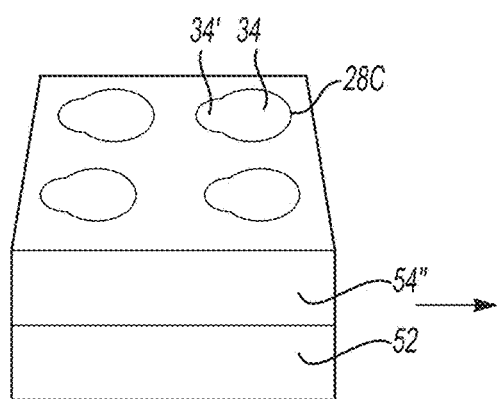
FIGS. 17A through 17D are schematic perspective views which together depict an example of the method disclosed herein using the patterned substrate of FIG. 11D.

FIG. 17A depicts the patterned resin 54'' including depressions 28C. Each of the depressions 28C includes a larger portion 34 and a smaller portion 34'. The depth of the depressions 28C (as shown in FIG. 11D) is omitted for clarity.

Figure 17B:
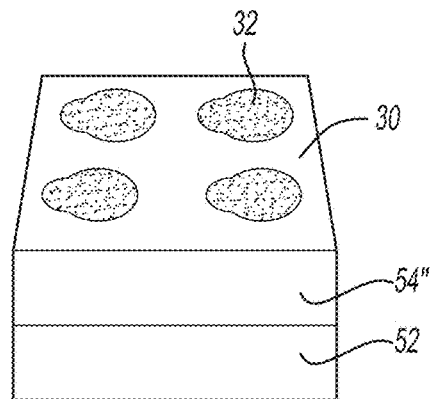

FIG. 17B depicts the polymer layer 32 in each of the depressions 28C. As shown in FIG. 17B, both the larger portion 34 and the smaller portion 34' of each depression 28C has the polymer layer 32 applied thereto. The polymer layer 32 may be selectively applied as described herein, which, in an example, may include activating the interstitial regions 30 and the exposed surfaces in the depressions 28C, depositing the polymer layer 32 on the activated interstitial regions 30 and in the depressions 28C, and removing the polymer layer 32 from the interstitial regions 30.

Figure 17D:
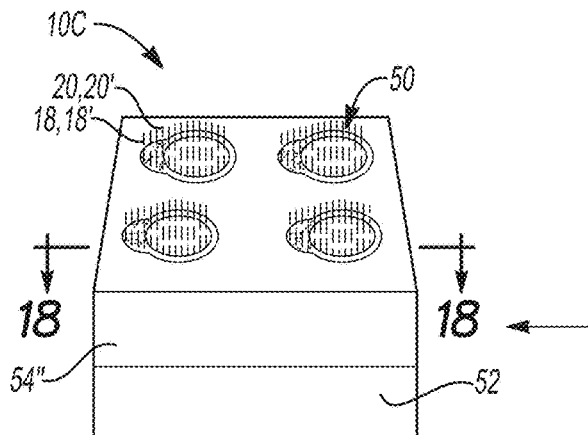
Figure 17C:
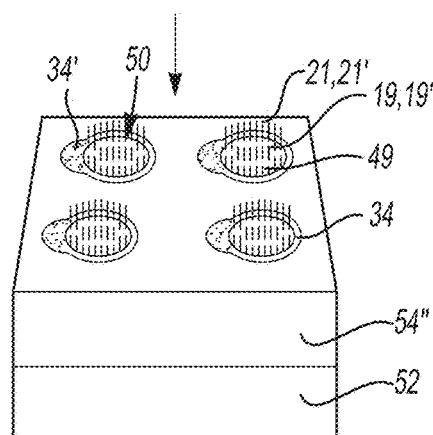

As shown in FIG. 17C, in this example of the method 100, functionalized beads 50 are deposited into the larger portions 34 of the depressions 28C. Any of the functionalized beads 50 described herein may be used in this example.

The functionalized beads 50 (including primers 19, 19' and 21, 21') may be deposited onto the patterned resin 54'' using any suitable technique, such as those described herein. Because of the size of the functionalized beads 50 and the size of the portions 34 and 34', size exclusion will prevent the functionalized beads 50 from entering the smaller portions 34' and will enable one functionalized bead 50 to self-assemble into one larger portion 34 of each depression 28C. In this example, the functionalized beads 50 may be physically entrapped in the respective larger portions 34 or may be chemically attached in the respective larger portions 34, e.g., via streptavidin/biotin linkers.

As shown in FIG. 17D, the smaller portions 34' of the depressions 28C may then be functionalized with the first primer set 12A, 12B, 12C, 12D. Any examples of the primers 18, 18' and 20, 20' described herein may be used, as long as they are selected to be different from and orthogonal to the primers 19, 19' and 21, 21' of the functionalized beads 5. In this example, the polymer layer 32 in the larger portions 34 of the depressions 28C is covered with the functionalized beads 50, and thus the polymer layer 32 in the larger portions 34 of the depressions 28C is not exposed. As such, the polymer reactive groups are not available for reaction with the first primer set 12A, 12B, 12C, 12D. The polymer reactive groups in the smaller portions 34' remain exposed, and thus are available for reaction with the first primer set 12A, 12B, 12C, 12D. Grafting of the primers 18, 18' and 20, 20' to the polymer layer 32 in the smaller portions 34' may be accomplished using any of the techniques described in reference to FIG. 13D.

FIG. 18 is a cross-sectional view of the portion of the flow cell 10C depicted in FIG. 17D. The flow cell 10C includes the support 52; the patterned resin 54'' on the support 52, the patterned resin 54'' including depressions 28C separated by interstitial regions 30; the first primer set 12A, 12B, 12C, 12D (including primers 18, 18' and 20, 20') attached to at least some of the depressions 28C; and the functionalized bead 50 positioned in the at least some of the depressions 28C so that at least some primers 18, 18' and 20, 20' of the first primer set 12A, 12B, 12C, 12D are exposed, the functionalized bead 50 including the second primer set 12A', 12B', 12C', 12D' attached at a surface of the core structure 49, wherein the second primer set 12A', 12B', 12C', 12D' is different than the first primer set 12A, 12B, 12C, 12D. In the example shown in FIGS. 17D and 18, each of the depressions 28C includes a first portion 34 with a first opening dimension that is larger than or equal to a diameter of the functionalized bead 50, and a second portion 34' with a second opening dimension that is smaller than the diameter of the functionalized bead 50; and the functionalized bead 50 is positioned in the first portion 34 of each of the at least some of the depressions 28C. Also in the example shown in FIGS. 17D and 18, the polymer layer 32 is present in the depressions 28C, and the first primer set 12A, 12B, 12C, 12D is attached to a portion of the polymer layer 32 unoccupied by the functionalized bead 50 (i.e., to the portion of the polymer layer 32 in the smaller portion 34' of the depression 28C).

Referring now to FIGS. 19A through 19D, another example of the method 100 involving the depressions 28C is shown. Each of the depressions 28C includes a larger portion 34 and a smaller portion 34'. The depth of the depressions 28C (as shown in FIG. 11D) is omitted for clarity.

FIG. 19B depicts the polymer layer 32 in each of the depressions 28C. As shown in FIG. 19B, both the larger portion 34 and the smaller portion 34' of each depression 28C has the polymer layer 32 applied thereto. The polymer layer 32 may be selectively applied as described herein, which, in this example, may include activating the interstitial regions 30 and the exposed surfaces in the depressions 28C, depositing the polymer layer 32 on the activated interstitial regions 30 and in the depressions 28C, and removing the polymer layer 32 from the interstitial regions 30.

In this example, as shown in FIG. 19C, the primer set 12A, 12B, 12C, 12D (including primers 18, 18' and 20, 20') is then grafted to the polymer layer 32 in each of the depressions 28C. Because the functionalized beads 50 have not been introduced, the polymer layer 32 in each portion 34, 34' of the depressions 28C is exposed, and thus its reactive groups are available for reaction with the first primer set 12A, 12B, 12C, 12D. Grafting may be accomplished using any of the techniques described in reference to FIG. 13D. Since the polymer layer 32 is exposed in each portion 34, 34' of the depressions 28C, the primers 18, 18' and 20, 20' can be grafted into each of the each portion 34, 34'.

As shown in FIG. 19D, the functionalized beads 50 may then be introduced into the larger portions 34 of the depressions 28C (having the polymer layer 32 and primer set 12A, 12B, 12C, 12D therein). The functionalized beads 50 may be deposited onto the patterned resin 54" using any suitable technique. Because of the size of the functionalized beads 50 and the size of the portions 34 and 34', size exclusion will prevent the functionalized beads 50 from entering the smaller portions 34' and will enable one functionalized bead 50 to self-assemble into one larger portion 34. In this example, the functionalized beads 50 may be physically entrapped in the respective larger portions 34, or may be chemically attached in the respective larger portions 34, e.g., via streptavidin/biotin linkers.

Figure 20:
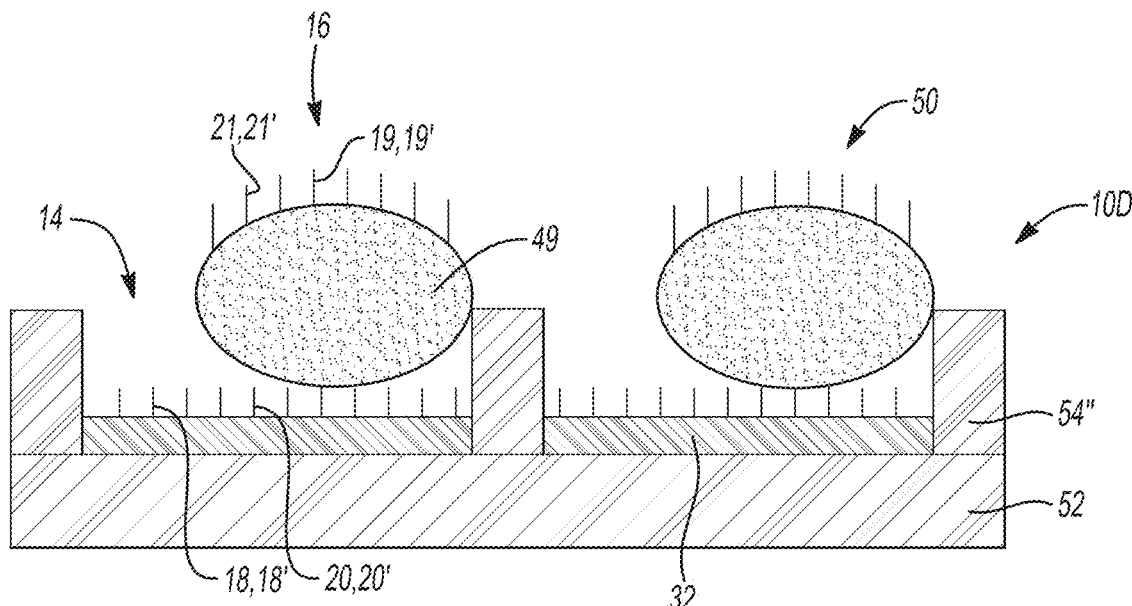
FIG. 20 is a cross-sectional view taken along line 10-10 of FIG. 19D.

FIG. 20 is a cross-sectional view of the portion of the flow cell 10D depicted in FIG. 19D. The flow cell 10D includes the support 52; the patterned resin 54" on the support 52, the patterned resin 54" including depressions 28C separated by interstitial regions 30; the first primer set 12A, 12B, 12C, 12D (including primers 18, 18' and 20, 20') attached to at least some of the depressions 28C; and the functionalized bead 50 positioned in the at least some of the depressions 28C so that at least some primers 18, 18' and 20, 20' of the first primer set 12A, 12B, 12C, 12D are exposed, the functionalized bead 50 including the second primer set 12A', 128', 12C', 12D' attached at a surface of the core structure 49, wherein the second primer set 12A', 128', 12C', 12D' is different than the first primer set 12A, 12B, 12C, 12D. In the example shown in FIGS. 19D and 20, each of the depressions 28C includes a first portion 34 with a first opening dimension that is larger than or equal to a diameter of the functionalized bead 50, and a second portion 34' with a second opening dimension that is smaller than the diameter of the functionalized bead 50; and the functionalized bead 50 is positioned in the first portion 34 of each of the at least some of the depressions 28C. Also in the example shown in FIGS. 19D and 20, the polymer layer 32 is present in the depressions 28C, the first primer set 12A, 12B, 12C, 12D is attached to the polymer layer 32 in the depressions 28C, and the functionalized bead 50 is positioned on some of the primers 18, 18' and 20, 20' of the first primer set 12A, 12B, 12C, 12D (i.e., on the primers 18, 18' and 20, 20' attached to the polymer layer 32 in the larger portion 34 of the depression 28C).

The example flow cells 10A, 10B, 10C, 10D are shown without a lid bonded thereto. While not shown, the flow cells 10A, 10B, 10C, 10D may have the lid bonded to at least a portion of the interstitial region 30 as described. In some examples, the lid may be bonded after the flow cell 10A, 10B, 10C, 10D is formed.

The flow cells 10A, 10B, 10C, 10D may be used in a variety of sequencing approaches or technologies, including techniques often referred to as sequencing-by-synthesis (SBS), cyclic-array sequencing, sequencing-by-ligation, pyrosequencing, and so forth. In one specific example, flow cells 10A, 10B, 10C, 10D may be exposed to the template fluid/mix, and amplification may be performed as described herein to generate the un-cleavable first template strand 40, the cleavable first template strand 46, the un-cleavable second template strand 44, the cleavable second template strand 42. Cleavage may be performed, and then the simultaneously paired-end sequencing method disclosed herein may be performed.

With any of the techniques used with the flow cells 10A, 10B, 10C, 10D, since the primer sets 12A, 12A' or 12B, 12B' or 12C, 12C', or 12D, 12D' are present in the depressions 28A or 28B or portions 34 or 34' of depression 28C and not on the interstitial regions 30, amplification and sequencing will be confined to the depressions 28A and 28B or 28C.

Block-copolymer Based Flow Cell

Some examples of the flow cell disclosed herein include the block copolymer, which is used with the multi-layered substrate including a patterned resin. These examples are described in reference to FIG. 21 through FIG. 25B.

In these examples, the patterned resin (e.g., 54') can be fabricated using a "top down" approach, such as nanoimprint lithography. Top down approaches can generate an array of depressions 28 with a high density, a low pitch, and small nanofeatures. When combined with the directed self-assembly of the block copolymer, which is a "bottom up" approach, even smaller features (having sub-lithographic size domains) may be formed within the depressions 28. Small features may be desirable because a higher cluster density may be obtained. Higher cluster density means that more bases can be read from a given unit area, which increases the genetic yield from the patterned flow cell. Moreover, the non-grafted regions (e.g., interstitial regions 30) surround the small features, which enable greater accessibility to primers grafted to the block copolymer. As such, utilization of the primers may increase.

In these examples, the block copolymer is self-assembled in the depressions 28 of the patterned resin, and not to interstitial regions 30 between the depressions 28. As such, additional processing for removal of material from the interstitial regions 30 is not involved.

These examples of the flow cell include a support 52; a patterned resin on the support 52, the patterned resin including depressions 28 separated by interstitial regions 30; a block copolymer on the patterned resin in the depressions 28, each block of the block copolymer having a block-specific functional group that is different from the block-specific functional group of each other block of the block copolymer; and a primer attached to the block-specific functional group of at least one of the blocks. In some examples, the primers include un-cleavable primers 18, 18' and 21, 21' attached to one block of the block-copolymer, and the flow cell may be used in paired-end sequencing techniques that involve sequentially sequencing forward template strands and then reverse template strands that are attached to the one block. In other examples, the respective primer sets 12A, 12A', or 12B, 12B', or 12C, 12C', or 12D, 12D' disclosed herein are attached to different blocks of the block-copolymer. In this example, one block includes primers 18, 18' and 20, 20' and another block includes primers 19, 19' and 21, 21'. This example of the flow cell may be used in the simultaneous paired-end sequencing techniques disclosed herein.

Examples of portions of the flow cells are shown in FIGS. 22E and 23, and will be described further herein.

Figure 21:
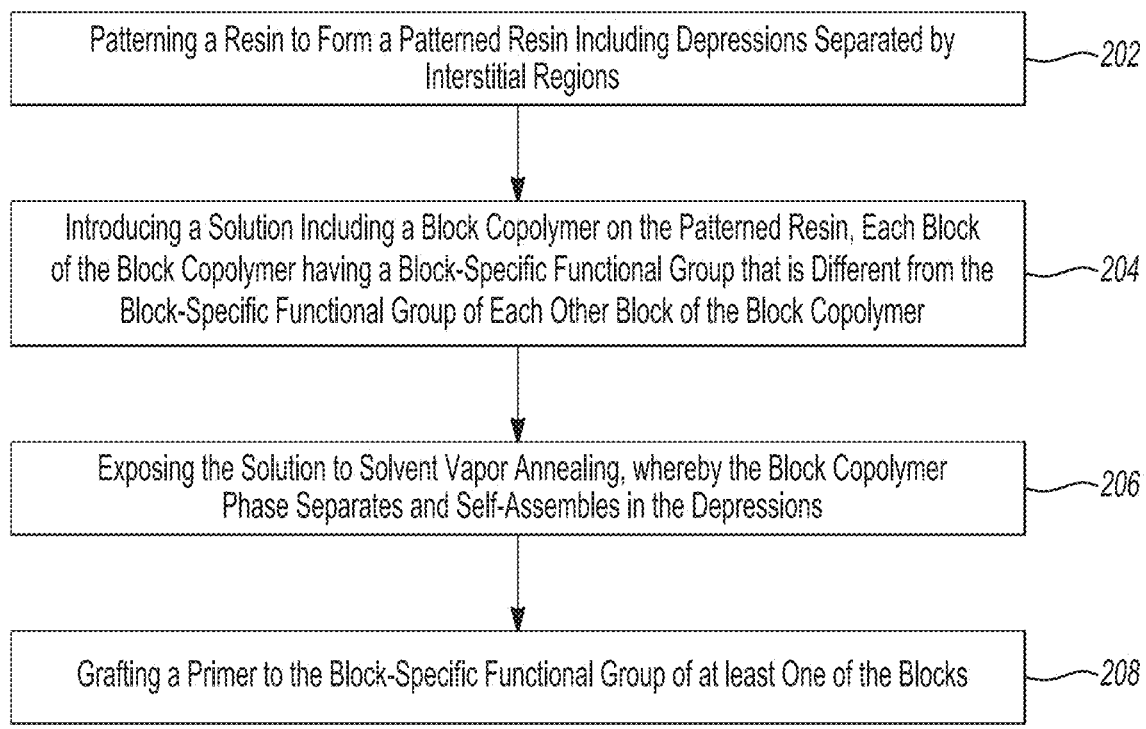
FIG. 21 is a flow diagram illustrating another example of a method disclosed herein.

An example of a method 200 for making an example of the flow cell is shown in FIG. 21. As shown in FIG. 21, the method 100 includes patterning a resin to form a patterned resin including depressions 28 separated by interstitial regions 30 (reference numeral 202); introducing a solution including a block copolymer on the patterned resin, each block of the block copolymer having a block-specific functional group that is different from the block-specific functional group of each other block of the block copolymer (reference numeral 204); exposing the solution to solvent vapor annealing, whereby the block copolymer phase separates and self-assembles in the depressions 28 (reference numeral 206); and grafting a primer to the block-specific functional group of at least one of the blocks (reference numeral 208). This method 200 will be described further in reference to FIGS. 22A through 22E.

FIG. 22A depicts the support 52, and FIG. 22B depicts a resin 54A deposited on the support 52. Any examples of the support 52 described herein may be used. With the block copolymer, the resin 54A is capable of having depressions 28 (FIG. 22C) defined therein and is also capable of acting as a guiding template for the subsequently deposited block copolymer 58 ("BCP" between FIGS. 22C and 22D). As such, any resin 54A that can be patterned using photolithography, nanoimprint lithography, stamping techniques, embossing techniques, molding techniques, microetching techniques, printing techniques, etc. may be used. Moreover, the resin 54A, after being patterned (i.e., patterned resin 54A'), should have a surface energy that is within the same range of the block copolymer 58 that is to be deposited thereon. In an example, the resin 54A/patterned resin 54A' and the block copolymer 58 each have a surface energy within a range of from about 25 mN/m to about 50 mM/m.

Some examples of resins 54A that can be patterned and act as guiding templates are selected from the group consisting of a polyhedral oligomeric silsesquioxane resin (POSS)-based resin, an epoxy resin, a poly(ethylene glycol) resin, a polyether resin, an acrylic resin, an acrylate resin, a methacrylate resin, and combinations thereof. While several examples have been provided, it is believed that any resin that can be radical cured may be used. Any of the resins 54 disclosed herein may be used for the resin 54A.

As shown between FIG. 22A and FIG. 22B, the resin 54A is deposited on the support 52. In an example of the method 200, deposition of the resin 44 involves chemical vapor deposition, dip coating, dunk coating, spin coating, spray coating, puddle dispensing, ultrasonic spray coating, doctor blade coating, aerosol printing, screen printing, microcontact printing, or inkjet printing.

The deposited resin 54 is then patterned, using any of the patterning techniques mentioned herein. In the example shown in and between FIG. 22A and FIG. 22B, nanoimprint lithography is used to pattern the resin 54. After the resin 54 is deposited, it may be soft baked to remove excess solvent. A nanoimprint lithography mold or working stamp 56 is pressed against the layer of resin 54 to create an imprint on the resin 54. In other words, the resin 54 is indented or perforated by the protrusions of the working stamp 56. The resin 54 may be then be cured with the working stamp 56 in place. Curing may be accomplished by exposure to actinic radiation, such as visible light radiation or ultraviolet (UV) radiation, or to radiation of a wavelength ranging from about 240 nm and 380 nm when a photoresist is used; or by exposure to heat when a thermal-curable resist is used. Curing may promote polymerization and/or cross-linking. As an example, curing may include multiple stages, including a softbake (e.g., to drive off solvent(s)) and a hardbake. The softbake may take place at a lower temperature, ranging from about 50° C. to about 150° C. The duration of the hardbake may last from about 5 seconds to about 10 minutes at a temperature ranging from about 100° C. to about 300° C. Examples of devices that can be used for softbaking and/or hardbaking include a hot plate, oven, etc.

After curing, the working stamp 56 is released. This creates topographic features, i.e., the depressions 16, in the resin 54. As shown in FIG. 22C, the resin 54 having the depressions 28 defined therein is referred to as the patterned resin 54'. The patterned resin 54' may be subject to further hard baking to complete the cure and to lock in the imprinted topography. In some examples, the hard baking may be performed at a temperature ranging from about 60° C. to about 300° C.

As shown in FIG. 22C, the patterned resin 54' includes the depressions 28 defined therein, and interstitial regions 30 separating adjacent depressions 28. In the examples disclosed herein, the depressions 28 become functionalized with the block copolymer (BCP) 58 and primers 18, 21 (FIG. 22F), while portions of the interstitial regions 20 may be used for bonding but will not have the block copolymer 58 or the primer(s) 18, 21.

As shown in FIG. 22C, the patterned resin 54' may then be exposed to processes to form the phase separated block copolymer 58 (including blocks 58A and 58B) in the depressions 28. As shown between FIG. 22C and FIG. 22D, a solution of the block copolymer 58 is deposited on the patterned resin 54', where each block 58A, 58B of the block copolymer 58 has a block-specific functional group that is different from the block-specific functional group of each other block 58B, 58A of the block copolymer 58. Various examples of the block copolymer 58 will now be described.

The block copolymer 58 is a heteropolymer made up of at least two different monomers. In one example, block copolymer 58 includes a first block 58A including a monomer having a primer-grafting functional group as its block-specific functional group, and a second block 58B including a monomer that is to adjust an interaction parameter to drive phase separation of the first and second blocks. In this example, the monomer of the second block 58B may also include a block-specific functional group that can react with (and thus attach to) the patterned resin 54'. The block-specific functional group that can react with (and thus attach to) the patterned resin 54' is referred to herein as the resin-attaching functional group. It is to be understood that the designations first and second do not indicate any particular order in the block copolymer, and that any block may include a primer-grafting functional group or a functional group to adjust an interaction parameter. For an example, the first block 58A may include a monomer having a block-specific functional group that is able to graft a primer (e.g., 18, 21) and that is able to adjust an interaction parameter to drive phase separation of the first and second blocks, and the second block 58B may include a monomer having the resin-attaching functional group. For another example, the first block 58A may include a monomer having a block-specific functional group that able to graft a primer (e.g., 18, 21) and attach to the resin 54', and that the second block 58B may include a monomer that is able to adjust an interaction parameter to drive phase separation of the first and second blocks.

In any examples of the block copolymer 58 disclosed herein, the primer-grafting functional group is selected from the group consisting of azide/azido, optionally substituted amino, optionally substituted alkenyl, aldehyde, optionally substituted hydrazone, optionally substituted hydrazine, carboxyl, hydroxy, optionally substituted tetrazole, optionally substituted tetrazine, nitrile oxide, nitrone, thiol, and combinations thereof. When multiple primer-grafting functional groups are included in a single block, different primers may be attached to the single block. When different primer-grafting functional groups are included in different blocks, different primers may be attached to the different blocks.

The primer-grafting functional group may be capable of reacting with a functional group attached to the 5' end of the primer. For example, a bicyclo[6.1.0] non-4-yne (BCN) terminated primer may be captured by an azide primer-grafting functional group of the block copolymer 58 via strain-promoted catalyst free click chemistry. For another example, an alkyne terminated primer may be captured by an azide primer-grafting functional group of the block copolymer 58 via copper catalyzed click chemistry. For still another example, a norbornene terminated primer may undergo a catalyst-free ring strain promoted click reaction with a tetrazine primer-grafting functional group of the block copolymer 58.

In an example, the primer-grafting functional group is an azido group attached to an acrylamide monomer. An example of this monomer is azido acetamido pentyl acrylamide. In another example, the primer-grafting functional group is an azido group attached to a benzene-containing monomer. Two examples of this monomer include benzyl azide or an azide functionalized styrene

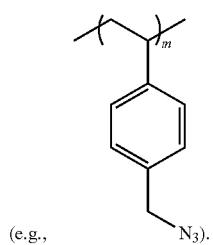

(e.g., )

In any examples of the block copolymer 58 disclosed herein, the resin-attaching functional group is selected from the group consisting of an amino group, an alcohol group, an aryl group, and a charged group. Suitable anionic charged groups include sulfates or carboxylic acids. Suitable cationic charged groups include ammonium, guanidinium, or imidazolium. In other examples, the resin-attaching functional group may a trifluoromethyl group (—CF$_3$). In still another example of the block copolymer 18 disclosed herein, the monomer including the resin-attaching functional group may be a siloxane monomer, such as SiO(CH$_3$)$_2$.

In an example, the resin-attaching functional group is an amino group attached to an acrylamide monomer. An example of this monomer is

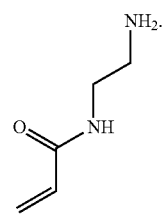

In this example, the ethyl bridge (between the nitrogens) may be replaced with a propyl bridge or any other bridge length that does not interfere with the desired function of the monomer. In an example, the bridge length may be up to 16 carbon atoms. In another example, the resin-attaching functional group is an aryl group of a styrene monomer. Other resin attaching groups (for covalent attachment) depend on how the resin 14 is functionalized. For example, if the resin includes epoxy groups, an amine or alcohol may be a suitable resin-attaching functional group.

Some examples of the block copolymer 58 include the primer-grafting functional group and the resin-attaching functional group. These groups may depend, respectively and in part, upon the primer (e.g., 18, 21 or 18, 20 or 18', 20' or 19, 21 or 19', 21') to be grafted and upon the patterned resin 54' that is to attach to the block copolymer 58. The following are some examples of block copolymers 58 that include both the primer-grafting functional group and the resin-attaching functional group.

In an example where the patterned resin 54' is an epoxy POSS, the block copolymer 58 includes a first block 58A including an acrylamide monomer having an amino group as its block-specific functional group, and a second block 58B including an azido acetamido pentyl acrylamide monomer having an azido group as its block-specific functional group. In this example, the first block 58A includes the resin-attaching functional group and the second block 58B includes the primer-grafting functional group, although the second block 58B may also function as a resin-attaching functional group. A specific example of this block copolymer 18 is:

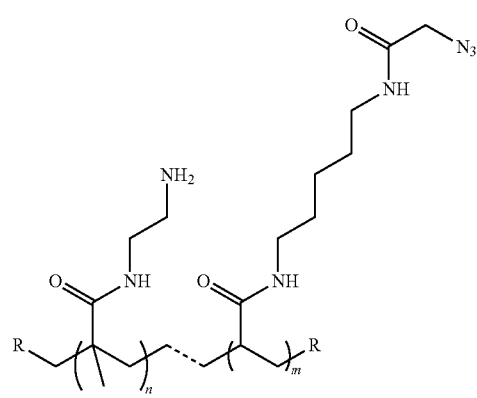

wherein R is hydrogen or a polymer initiating species end group, n ranges from 1 to 10,000, and m ranges from 1 to 10,000. Examples of the polymer initiating species end group include a reversible addition-fragmentation chain transfer (RAFT) end group, an atom transfer radical polymerization (ATRP) end group, a nitroxide-mediated radical polymerization (NMP) end group, a tetramethylethylenediamine (TEMED) end group, or a free-radical polymerization (FRP) end group. In another example, n and m independently range from about 1 to about 1,000.

In another example where the patterned resin 54' is an epoxy POSS, the block copolymer 58 includes a first block 58A including a styrene monomer having an aryl group as its block-specific functional group, and a second block 58B including an azide functionalized styrene having an azido as its block-specific functional group. In this example, the first block 58A includes the resin-attaching functional group and the second block 58B includes the primer-grafting functional group, although the second block 58B may also function as a resin-attaching functional group. A specific example of this block copolymer 58 is:

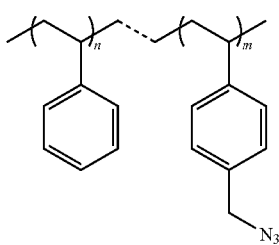

wherein n ranges from 1 to 10,000, and m ranges from 1 to 10,000. In another example, n and m independently range from about 1 to about 1,000.

In still another example where the patterned resin 54' is an epoxy POSS, the block copolymer 58 includes a first block 58A including an azide functionalized styrene having an azido as its block-specific functional group, and a second block 58B including a siloxane monomer having the siloxane as its block-specific functional group. In this example, the first block 58A includes the primer-grafting functional group, although the first block 58A may also function as a resin-attaching functional group, and the second block 58B includes the resin-attaching functional group. A specific example of this block copolymer 58 is:

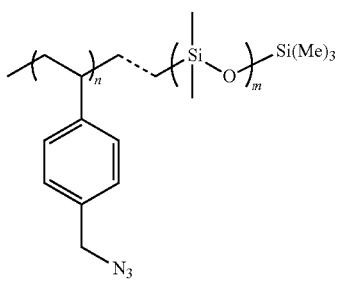

wherein n ranges from 1 to 10,000, and m ranges from 1 to 10,000. In another example, n and m independently range from about 1 to about 1,000.

In an example where the patterned resin 54' is an amorphous fluoropolymer (such as CYTOP®), the block copolymer 58 includes a first block 58A including a monomer having a trifluoromethyl group as its block-specific functional group, and a second block 58B including a monomer having a primer-grafting and resin-grafting functional group as its block-specific functional group. In one example of this block copolymer 58, the second block 58B includes the azido acetamido pentyl acrylamide monomer and the first block 58A (which, in this example, may be a surface energy altering functional group) may be a fluorinated acrylate or a fluorinated acrylamide. Specific examples of this block copolymer 18 have the structure:

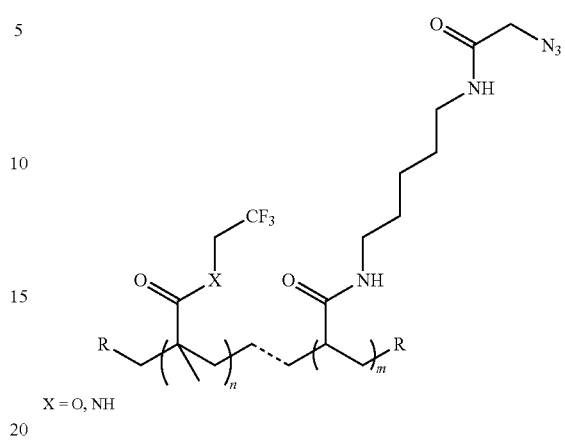

X = O, NH wherein n ranges from 1 to 10,000, and m ranges from 1 to 10,000. In another example, n and m independently range from about 1 to about 1,000. In another example of this block copolymer 58 (which is suitable for use with an amorphous fluoropolymer), the second block 58B includes azide functionalized styrene and the first block 58A (in this example the surface energy altering functional group) may be trifluoroethyl acrylate. A specific example of this block copolymer 58 has the structure:

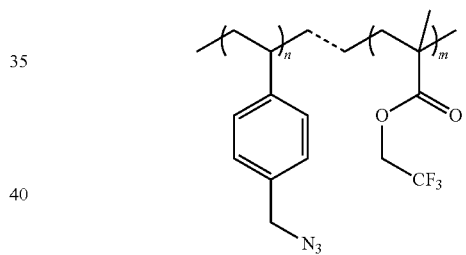

wherein n ranges from 1 to 10,000, and m ranges from 1 to 10,000. In another example, n and m independently range from about 1 to about 1,000.

It is to be further understood that the block copolymers 58 disclosed herein may also include one or more other monomers that do not interfere with the respective functions of the blocks 58A and/or 58B (e.g., primer grafting, resin attaching, phase separating, etc.). The additional monomer(s) (and specifically the block-specific functional group of the additional monomer(s)) of the additional block(s) may be selected to affect/alter a surface free energy of the block copolymer 58, to affect the stability of the block copolymer 58, to attach another primer, and/or to attach an enzyme. Examples of monomers that can affect/alter the surface free energy include a trifluoromethyl group of an acrylate monomer (e.g., trifluoroethyl acrylate or trifluoroethyl methacrylate) or of trifluoroethyl acrylamide. Examples of monomers that can attach an enzyme may include the following block-specific functional groups: thiols, amines, or alcohols, which can react with N-hydroxysuccinimide (NHS)-functionalized enzymes. It is to be understood that other functional groups may be used to attach enzymes or other biomolecules. As such, some examples of the block copolymer 58 are terpolymers, which will be discussed in further detail in reference to FIG. 24A and FIG. 24B.

As mentioned above, in the method 200, a solution of the block copolymer 58 is introduced on the patterned resin 54' (as shown between FIGS. 22C and 22D). The solution may be a dilute solution (e.g., ranging from about 0.01 wt % to about 10 wt %) of the block copolymer 58 in a suitable solvent, such as toluene. The block copolymer 58 solution may be deposited using any suitable technique, such as spin coating, etc.

For the block copolymer 58 to self-assemble and undergo microphase separation on the topologically patterned support (e.g., patterned resin 54'), the solution including the block copolymer is to have a high Huggins interaction parameter with the underlying patterned resin 54'. In an example, the solution of the block copolymer 58 has a Flory-Huggins interaction parameter ranging from about 0.04 to about 0.30. In another example, the solution of the block copolymer 58 has a Flory-Huggins interaction parameter of about 0.26.

The as-deposited block copolymer 58 on the patterned resin 54' is then exposed to solvent annealing. The solvent vapor, temperature, and time used in solvent annealing may depend upon the block copolymer 58 used, and, in particular, on the conditions at which the block copolymer 58 self-assembles into the depressions 28 and microphase separates into the respective blocks 58A and 58B. In an example, the solvent vapor is toluene, the temperature is room temperature (e.g., from about 14° C. to about 25° C.), and the time is about 3 hours. It is to be understood that the solvent selection, annealing time, and annealing temperature depend on the block copolymer. Some suitable solvents may be toluene, heptane, higher alkanes and mixtures thereof. The time and temperature may influence the morphology in the depressions 28, and thus may be controlled. As example, annealing time may range from 1 minute to 180 minutes, or even longer, for example, from about 3 hours to about 48 hours; and the annealing temperature may range from 18° C. to about 250° C.

Figure 23A:
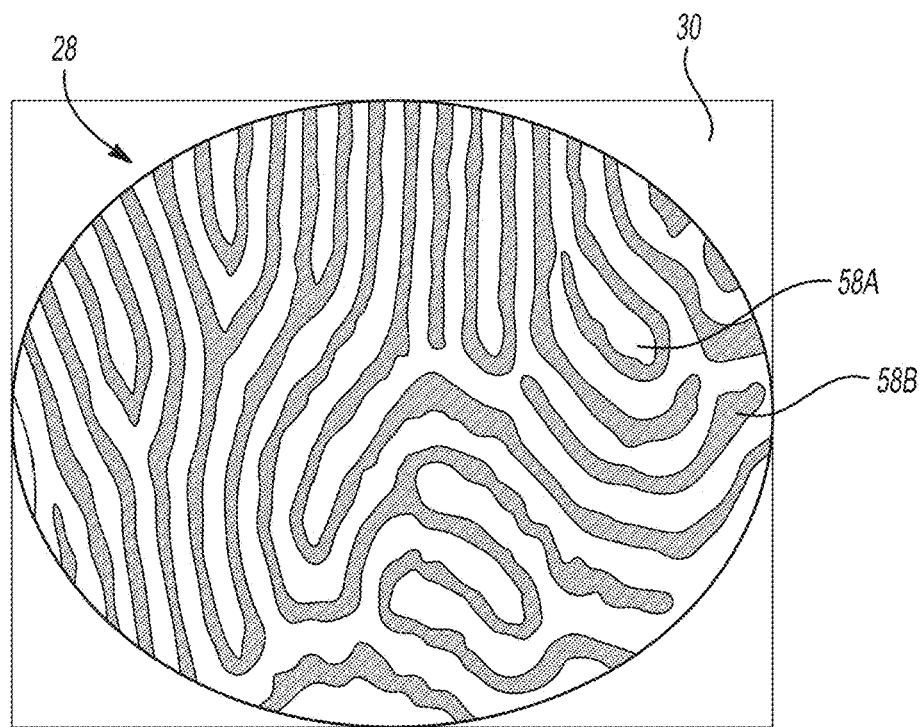
FIGS. 23A and 23B are schematic, top views of examples of depressions and surrounding interstitial regions, where different examples of block copolymers are self-assembled and phase separated in the depressions, where each figure shows a different pattern of the blocks.
Figure 23B:
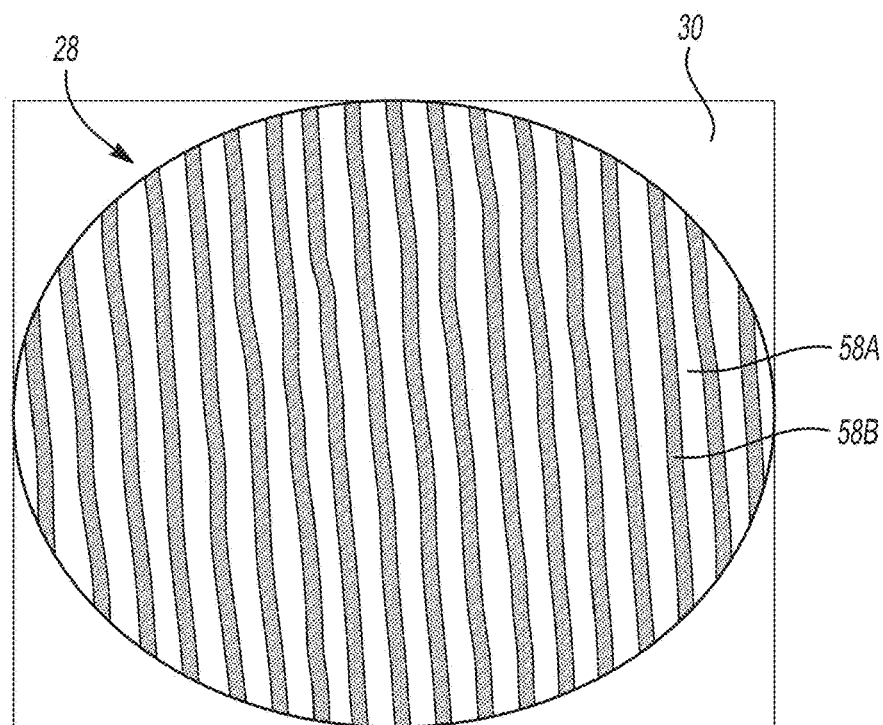

As a result of solvent annealing, the block copolymer 58 self-assembles into the depressions 16 (and thus is not present on the interstitial regions 30) and also phase separates into segregated domains, or blocks 58A, 58B. In FIG. 2D, the segregated blocks 58A, 58B have a circular or spiral pattern, although the pattern may depend upon the block copolymer 58 used. Other examples of the pattern of the block copolymer 58 are shown, for example, in FIGS. 23A and 23B. FIG. 23A is a top view of a depression 28 and some of the surrounding interstitial region 30, where the block copolymer 58 in the depression 28 phase separates into blocks 58A and 58B that exhibit a fingerprint pattern. FIG. 23B is a top view of a depression 28 and some of the surrounding interstitial region 30, where the block copolymer 58 in the depression 28 phase separates into blocks 58A and 58B that exhibit a line pattern. The blocks 58A, 58B have sub-lithographic size domains.

During solvent annealing the block 58A or 58B including the resin-attaching functional group may react with the patterned resin 54', and thus may attach to the patterned resin 54'.

While not shown, in some examples of the method 200, the patterned resin 54', including the phase separated and self-assembled block copolymer 58A, 58B in the depressions 28 is exposed to an additional curing process. Curing may be performed as previously described.

As shown between FIGS. 22D and 22E, a grafting process is performed in order to graft primers (18, 21 or 18', 21' for sequential paired-end sequencing) or (18, 20 or 18', 20' and 19, 21 or 19', 21' for simultaneous paired-end sequencing) to any primer-grafting functional groups of the block(s) 58A and/or 58(B) in the depression(s) 28.

In an example, grafting may be accomplished by flow through deposition (e.g., using a temporarily bound lid), dunk coating, spray coating, puddle dispensing, or by another suitable method that will attach the primer(s) (18, 21 or 18', 21' for sequential paired-end sequencing) or (18, 20 or 18', 20' and 19, 21 or 19', 21' for simultaneous paired-end sequencing) to the primer-grafting functional groups of the block(s) 58A and/or 58B. In an example of simultaneous paired-end sequencing, primers 18, 20 or 18', 20' may be grafted to one block 58A and primers 19, 21 or 19', 21' may be grafted to the other block 58B. Each of these example techniques may be performed as described herein and may utilize a primer solution or mixture, which may include the primer(s), water, a buffer, and a catalyst.

It is to be understood that primer(s) (un-cleavable primers 18, 21 or 18', 21' for sequential paired-end sequencing) or (un-cleavable/cleavable primer pairs 18, 20 or 18', 20' and 19, 21 or 19', 21' for simultaneous paired-end sequencing) will attach to the block(s) 58A and/or 58(B) that include the primer-grafting functional groups. In the example shown in FIGS. 22E and 22F, the primer(s) 18, 21 are attached to the block 58B and not to the block 58A. In this example, block 58A may have contributed the interaction parameter to drive phase separation of the first and second blocks 58A, 58B, and may also be attached to the patterned resin 54' through a resin-attaching functional group.

Figure 24:
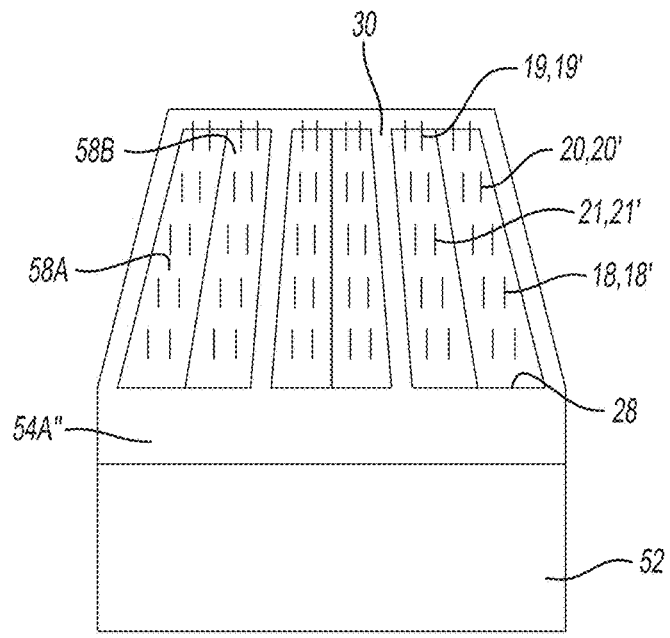
FIG. 24 depicts a schematic perspective view of an example of a flow cell disclosed herein.

Referring now to FIG. 24, another example is depicted with the block copolymer 58 phase separated into two blocks 58A and 58B. In this example, two different primer sets, one including primers 18, 18' and 20, 20' and the other including primers 19, 19' and 21, 21' are attached to the respective blocks 58A, 58B. This example enables simultaneous paired end reads during sequencing as described herein. In this example, each of the respective blocks 58A, 58B includes primer-grafting functional groups that can attach the respective primer sets.

Figure 25A:
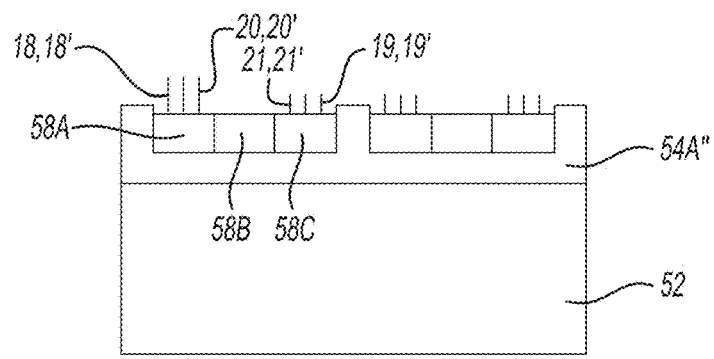
FIGS. 25A and 25B are schematic cross-sectional views depicting different examples of the flow cells disclosed herein which include triblock copolymers.

As mentioned above, some of the block copolymers 58 are terpolymers, where each block includes a different block-specific functional group. In one example, the block copolymer 58 is a terpolymer including a first block, a second block, and a third block; where the block-specific functional group of the first block is attached to the patterned resin (i.e., is the resin-attaching functional group); the block-specific functional group of the second block is attached to primer(s) (i.e., is the primer-grafting functional group); and the block-specific functional group of the third block is attached to i) another primer(s) that is different than the primer(s) attached to the block-specific functional group of the second block or ii) to an enzyme (e.g., NEXTERA™ transposomes). An example of the phase separated terpolymer is shown in FIG. 25A. In this example, the segregated terpolymer includes blocks 58A, 58B, 58C, where 58A includes the primer-grafting functional group, 58B includes the resin-attaching functional group and/or affects a surface free energy of the block copolymer and/or affects stability of the block copolymer, and 58C includes a different primer-grafting functional group or an enzyme attaching functional group. As depicted, block 58A attaches the first primer set 12A, 12B, 12C, 12D, including primers 18, 18' and 20, 20', and block 58C attaches the second primer set 12A', 12B', 12C', 12D', including primers 19, 19' and 21, 21'. In this example, block 58A serves as region 14 and block 58C serves as region 16. In another example, the regions 14, 16 may be blocks (e.g., 58A and 58B or 58B and 58C) that are directly adjacent to one another.

Figure 25B:
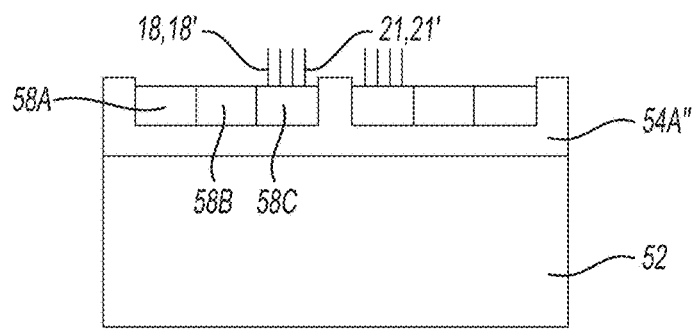

In another example, the block copolymer 58 is a terpolymer including a first block, a second block, and a third block; where the block-specific functional group of the first block is attached to the patterned resin 54' (i.e., is the resin-attaching functional group); the block-specific functional group of the second block is attached to the primer(s) (i.e., is the primer-grafting functional group); and the block-specific functional group of the third block affects a surface free energy of the block copolymer or affects stability of the block copolymer. An example of the phase separated terpolymer is shown in FIG. 25B. In this example, the segregated terpolymer includes blocks 58A, 58B, 58C, where 58A includes the resin-attaching functional group, 58B affects the surface free energy of the block copolymer or affects stability of the block copolymer, and 58C includes a primer-grafting functional group. In this example, un-cleavable primers 18, 21 are attached, and thus this example may be particularly suitable for sequential paired-end sequencing.

Figure 38A:
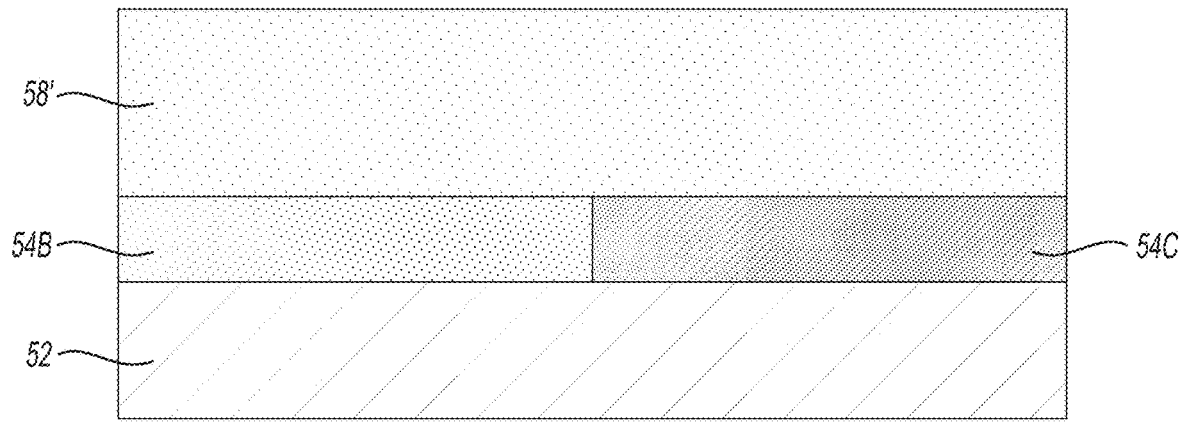
FIGS. 38A and 38B are schematic views which together illustrate an example method involving another example of a block copolymer.
Figure 38B:
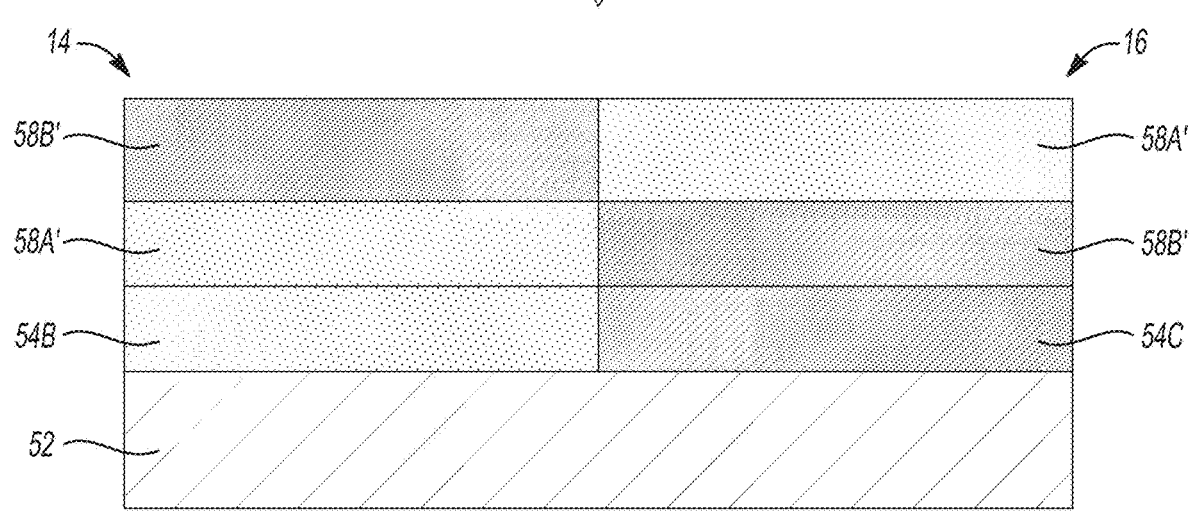

FIG. 38A and FIG. 38B together depict another example method involving a block copolymer 58'. In this example, the block copolymer 58' is a lamellar block copolymer. A lamellar block copolymer will self-assemble so that the different blocks 58A' and 58B' are layered one on top of the other so that they are parallel to the underlying materials 54B, 54C, and support 52. Examples of lamellar block copolymers include copolymers including heterocyclic azide units. The materials 54B, 54C may be different examples of the resin 54A described herein, silanes, or silanized resins, and may be selected to guide the self-assembly of the block copolymer 58'. Under controlled conditions, the block copolymer 58' self-assembles into specific domains/blocks 58A' and 58B' that are layered on the underlying materials 54B, 54C. In the example shown in FIGS. 38A and 38B, as a result of annealing, the domains/blocks 58A' and 58B' self-assemble so that block 58'B is exposed at the surface at one area (overlying material 54B) and so that the other block 58A' is exposed at the surface at another area (overlying material 54C). The block 58B' may include primer-attaching functional groups that can attach the first primer set 12A, 12B, 12C, 12D, including primers 18, 18' and 20, 20'; and the block 58A' may include different primer-attaching functional groups that can attach the second primer set 12A', 12B', 12C', 12D', including primers 19, 19' and 21, 21'. In this example, block 58B' serves as region 14 and block 58A' serves as region 16.

The flow cells including the block copolymer 58, 58' may be used in a variety of sequencing approaches or technologies, including techniques often referred to as sequencing-by-synthesis (SBS), cyclic-array sequencing, sequencing-by-ligation, pyrosequencing, and so forth. In some of these examples, since the phase separated blocks 58A, 58B, 58C and attached primer(s) (un-cleavable primers 18, 21 or 18', 21' for sequential paired-end sequencing) or (un-cleavable/cleavable primer pairs 18, 20 or 18', 20' and 19, 21 or 19', 21' for simultaneous paired-end sequencing) are present in the depressions 28 and not on the interstitial regions 30, amplification will be confined to the depressions 28.

As one example, a sequencing by synthesis (SBS) reaction may be run on a system such as the HISEQ™, HISEQX™, MISEQ™, MISEQDX™, MINISEQ™ NOVASEQ™, NEXTSEQDX™, NEXTSEQ™, or any other sequencer systems from Illumina (San Diego, CA). In SBS, extension of a sequencing primer along a nucleic acid template (e.g., the sequencing template) is monitored to determine the sequence of nucleotides in the template. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the sequencing primer (thereby extending the primer) in a template dependent fashion such that detection of the order and type of nucleotides added to the sequencing primer can be used to determine the sequence of the template.

For example, to initiate a first SBS cycle, one or more labeled nucleotides, DNA polymerase, etc., may be delivered into/through the flow channel, etc. that houses an array of forward or reverse strands attached to un-cleavable primers 18, 21 or 18', 21' (for sequential paired-end sequencing), or both forward and reverse strands attached to the un-cleavable/cleavable primer pairs 18, 20 or 18', 20' (for simultaneous paired-end sequencing), where sequencing primer extension causes a labeled nucleotide to be incorporated, can be detected through an imaging event. During an imaging event, an illumination system (not shown) may provide an excitation light to the functionalized depressions.

In these example, the nucleotides can further include a reversible termination property that terminates further primer extension once a nucleotide has been added, and a deblocking agent can be used to continue sequencing. Wash(es) may take place between the various fluid delivery steps. The SBS cycle can then be repeated n times to extend the sequencing primer by n nucleotides, thereby detecting a sequence of length n.

While SBS has been described in detail, it is to be understood that the flow cells described herein may be utilized with other sequencing protocol, for genotyping, or in other chemical and/or biological applications.

To further illustrate the present disclosure, examples are given herein. It is to be understood that these examples are provided for illustrative purposes and are not to be construed as limiting the scope of the present disclosure.

Examples

Example 1

Figure 39A:
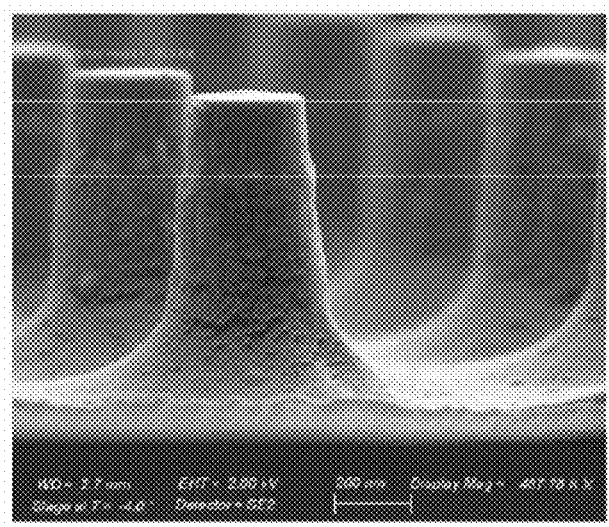
FIG. 39A is a scanning electron microscopy (SEM) image of a flow cell substrate having 50 μm diameter depressions separated by interstitial regions, with a pre-grafted polymer layer deposited thereon.
Figure 39B:
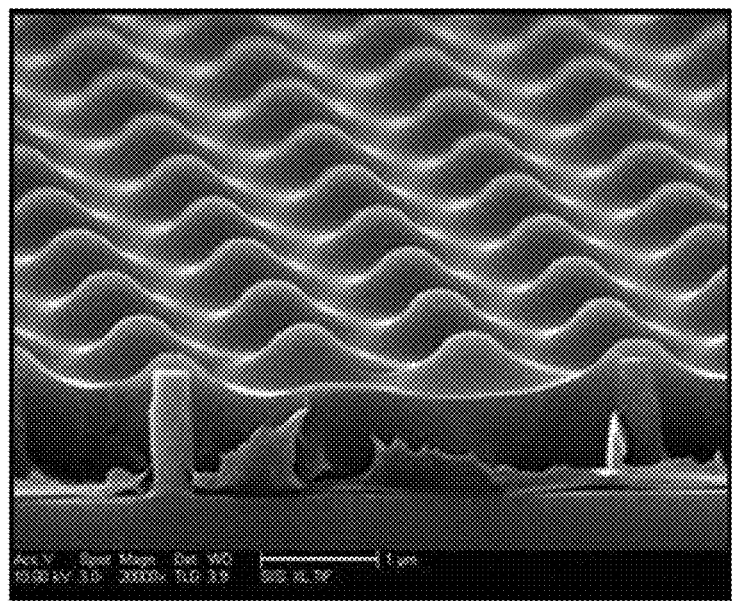
FIG. 39B is a SEM image of the flow cell substrate of FIG. 39A with a protection layer deposited on the pre-grafted polymer layer.
Figure 39C:
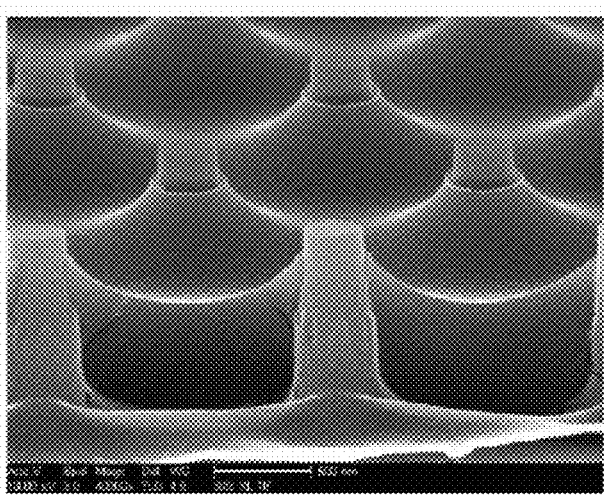
FIG. 39C is a SEM image of the flow cell substrate of FIG. 39B after etching to remove the protection layer from the interstitial regions.

PAZAM with pre-grafted P7 and P5U primers was deposited on a flow cell substrate having pillar-like features that were about 400 nm tall and about 350 nm in diameter. A scanning electron micrograph (SEM) image of a portion of the deposited pre-grafted PAZAM layer is shown in FIG. 39A. A lift-off resist was deposited on this first grafted PAZAM layer to form an example of the protection layer described herein. A SEM image of a portion of the deposited protection layer is shown in FIG. 39B. Etching was then performed to remove the protection layer and the first grafted PAZAM layer from the tops of the pillar-like features. A SEM image of a portion of the substrate after etching is shown in FIG. 39C. PAZAM was deposited on the tops of the pillar-like features and on the remaining protection layer to form a second PAZAM layer. The second PAZAM layer was grafted with P5 and P7U primers.

A lift-off process was used to remove the protection layer and any of the second grafted PAZAM layer from the first grafted PAZAM layer.

Library fragments from the same genome (from the Human genome) were introduced to the flow cell. The library fragments included a portion that was complementary to the P5 of P7 primer sequences, along with index sequences, and read 1 and read 2 sequences. The library fragments were seeded and clustering was performed using bridge amplification. Simultaneous paired-end sequencing was then performed.

At the border area between the pillar-like features and neighboring regions, it was found that about 34% of all the reads were paired.

Figure 40A:
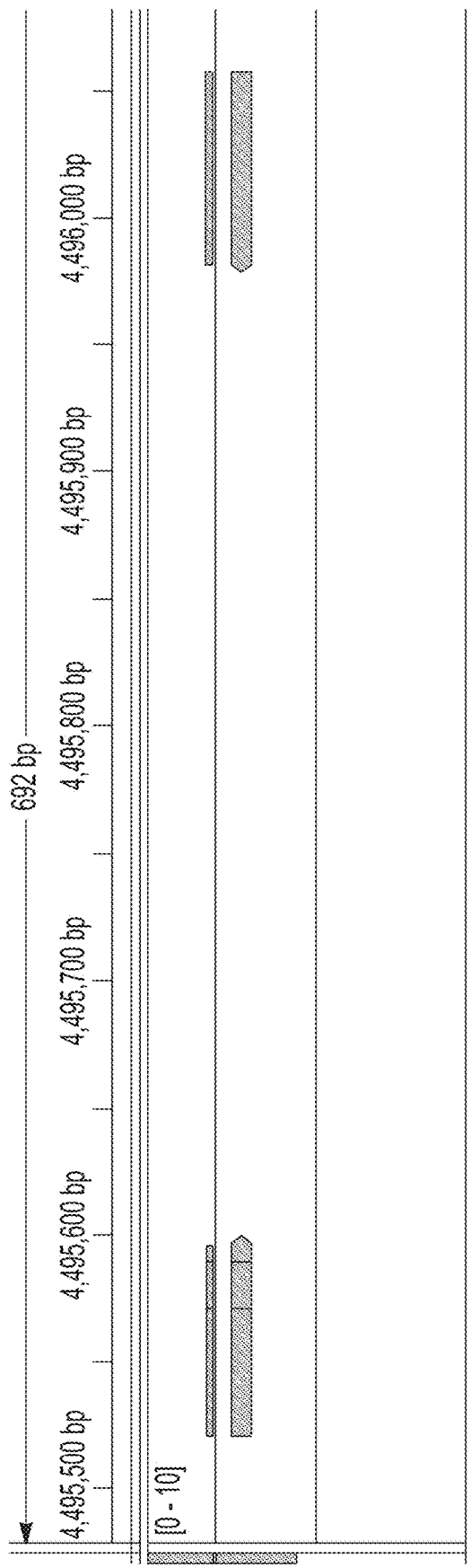
FIGS. 40A and 40B depict the data analysis for a simultaneous paired end read (FIG. 40A) and a sequential paired end read (FIG. 40B)

The reads were extracted from a single location and were aligned to the genome. FIG. 40A illustrates two R1 reads (R1 and R1') that are imputed to be simultaneous paired-end reads.

Figure 40B:
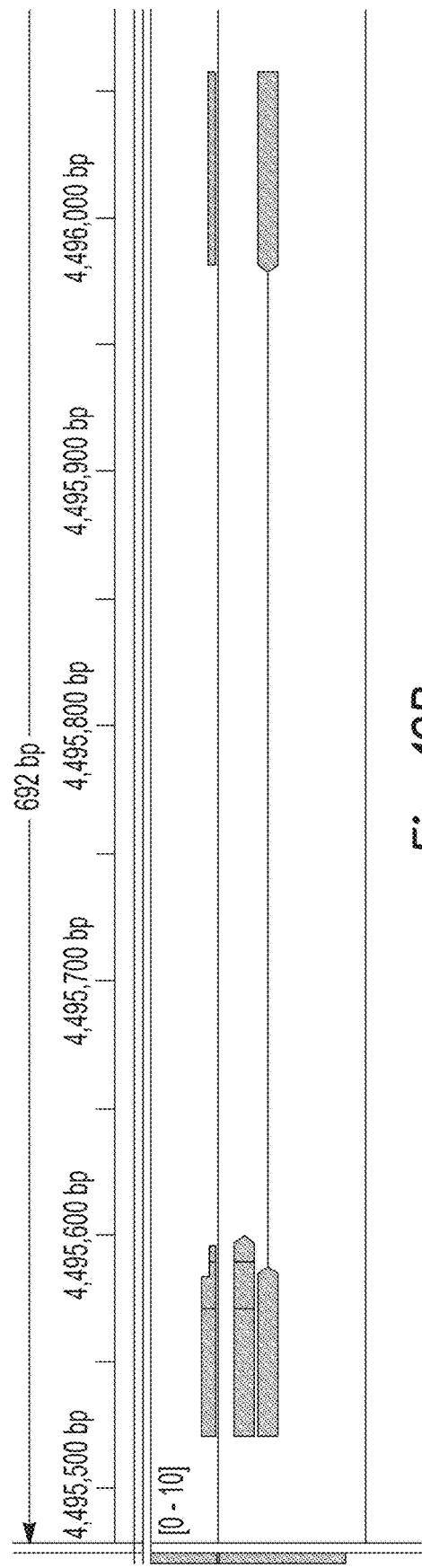

The flow cell was also processed through a sequential paired-end synthesis (forward strands sequenced and removed followed by reverse strand sequencing). FIG. 40B illustrates the results from FIG. 40A with the second read (R2) from the sequential paired end synthesis flipped to show that it indeed matches the simultaneous paired-end read pair. The clipped portion in R2 may be due to quality drop, whereas the R1 read is a higher quality, unclipped read. These results demonstrate that the methods disclosed herein can produce equivalent information to the standard paired-end sequencing (FIG. 40B) using simultaneously generated pairs (FIG. 40A).

Still further, the insert size distributions of the library fragments were roughly equivalent for data based on simultaneous paired-end sequencing and standard (sequential) paired end sequencing. These results further demonstrate that the methods disclosed herein, using simultaneously generated pairs, can produce equivalent information to the standard paired-end sequencing.

Example 2

PAZAM was deposited on a planar flow cell substrate and grafted with P7 and P5U primers. A protection layer (Shipley 1813 photoresist) was deposited on top of this first grafted PAZAM layer. UV light was used through a photomask to expose defined portions of the protection layer, which were then developed away in solvent, leaving behind 50 µm circular pads of the protective layer. Air plasma was used to etch away the exposed portions of the first grafted PAZAM layer in the interstitial regions, while the portions under the protective pads remained intact. A second layer of PAZAM was then deposited on the interstitial regions and on the remaining protection layer. This second deposited PAZAM was then grafted with P5 and P7U primers.

A lift-off process was used to remove the protection layer and any of the second grafted PAZAM layer from the first grafted PAZAM layer.

Library fragments from the same genome (from the Human genome) were introduced to the flow cell. The library fragments included a portion that was complementary to the P5 of P7 primer sequences, along with index sequences, and read 1 and read 2 sequences. The library fragments were seeded and clustering was performed using bridge amplification. Simultaneous paired-end sequencing was then performed.

At the border area between the first grafted and second grafted PAZAMs, it was found that about 2.2% of all the reads were paired. This meant that two reads were within 2 µm of each other and were within 2 kb of each other in the genome.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if such values or sub-ranges were explicitly recited. For example, a range of about 400 nm to about 1 µm (1000 nm), should be interpreted to include not only the explicitly recited limits of about 400 nm to about 1 µm, but also to include individual values, such as about 708 nm, about 945.5 nm, etc., and sub-ranges, such as from about 425 nm to about 825 nm, from about 550 nm to about 940 nm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A method, comprising:

patterning a resin to form a patterned resin including depressions separated by interstitial regions;

introducing a solution including a block copolymer on the patterned resin, each block of the block copolymer having a block-specific functional group that is different from the block-specific functional group of each other block of the block copolymer;

exposing the solution to solvent vapor annealing, whereby the block copolymer phase separates and self-assembles in the depressions; and grafting a primer to the block-specific functional group of at least one of the blocks.

2. The method as defined in claim 1, wherein patterning the resin involves nano-imprint lithography.

3. The method as defined in claim 1, wherein the solution including the block copolymer has a Flory-Huggins interaction parameter ranging from about 0.04 to about 0.30.

4. The method as defined in claim 1, wherein prior to grafting, the method further comprises exposing the patterned resin, including the phase separated and self-assembled block copolymer in the depressions, to a curing process.

5. The method as defined in claim 1, wherein the patterned resin is selected from the group consisting of a polyhedral oligomeric silsesquioxane resin (POSS)-based resin, an epoxy resin, a poly(ethylene glycol) resin, a polyether resin, an acrylic resin, an acrylate resin, a methacrylate resin, and combinations thereof.

6. The method as defined in claim 1, wherein:

the patterned resin is an epoxy polyhedral oligomeric silsesquioxane resin (POSS)-based resin; and the block copolymer includes:

a first block including an acrylamide monomer having an amino group as its block-specific functional group; and a second block including an azido acetamido pentyl acrylamide monomer having an azido group as its block-specific functional group.

7. The method as defined in claim 6, wherein:

the patterned resin is an epoxy polyhedral oligomeric silsesquioxane resin (POSS)-based resin; and the block copolymer is:

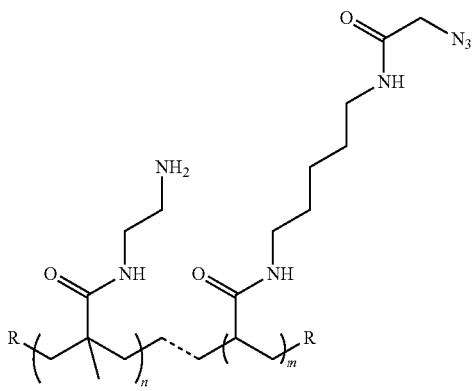

wherein R is hydrogen or a polymer initiating species end group, n ranges from 1 to 10,000, and m ranges from 1 to 10,000.

8. The method as defined in claim 1, wherein:

the patterned resin is an epoxy polyhedral oligomeric silsesquioxane resin (POSS)-based resin; and the block copolymer is:

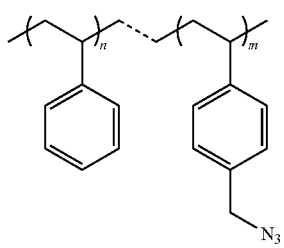

wherein n ranges from 1 to 10,000, and m ranges from 1 to 10,000.

9. The method as defined in claim 1, wherein:

the patterned resin is an epoxy polyhedral oligomeric silsesquioxane resin (POSS)-based resin; and the block copolymer is:

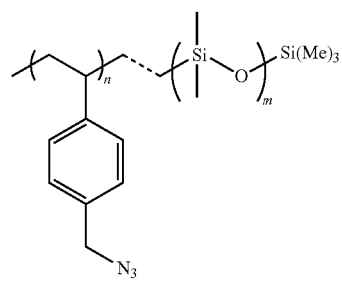

wherein n ranges from 1 to 10,000, and m ranges from 1 to 10,000; in another example, n and m independently range from about 1 to about 1,000.

10. The method as defined in claim 1, wherein:
the patterned resin is an amorphous fluoropolymer; and
the block copolymer includes:
  a first block including a monomer having a trifluoromethyl group as its block-specific functional group; and
  a second block including a monomer having a primer-grafting functional group as its block-specific functional group.

11. The method as defined in claim 1, wherein:
the block copolymer includes:
  a first block including a monomer having a primer-grafting functional group as its block-specific functional group; and
  a second block including a monomer to adjust an interaction parameter to drive phase separation of the first and second blocks;
the primer-grafting functional group is an azido group; and
the block-specific functional group of the monomer of the second block is selected from the group consisting of an amino group, an alcohol group, an aryl group, and a charged group.

12. The method as defined in claim 1, wherein the block copolymer is a terpolymer including a first block, a second block, and a third block, the block-specific functional group of the first block is attached to the patterned resin, the block-specific functional group of the second block is attached to the primer, and the block-specific functional group of the third block is attached to an other primer that is different than the primer, or to an enzyme.

13. The method as defined in claim 1, wherein the block copolymer is a terpolymer including a first block, a second block, and a third block, the block-specific functional group of the first block is attached to the patterned resin, the block-specific functional group of the second block is attached to the primer, and the block-specific functional group of the third block affects a surface free energy of the block copolymer or affects stability of the block copolymer.

14. The method as defined in claim 1, wherein the depressions are selected from the group consisting of wells and trenches.

15. The method as defined in claim 1, wherein the patterned resin and the block copolymer each have a surface free energy within a range of from about 25 mN/m to about 50 mN/m.

* * * * *

SEQUENCE LISTING

```
Sequence total quantity: 2
SEQ ID NO: 1            moltype = DNA  length = 20
FEATURE                 Location/Qualifiers
source                  1..20
                        mol_type = other DNA
                        organism = synthetic construct
SEQUENCE: 1
aatgatacgg cgaccaccga                                                     20

SEQ ID NO: 2            moltype = DNA  length = 21
```

| FEATURE | Location/Qualifiers |
|---|---|
| source | 1..21<br>mol_type = other DNA<br>organism = synthetic construct |– 
SEQUENCE: 2
caagcagaag acggcatacg a                                           21